(12) United States Patent
Coulstock et al.

(10) Patent No.: US 8,679,496 B2
(45) Date of Patent: Mar. 25, 2014

(54) ANTI-SERUM ALBUMIN SINGLE VARIABLE DOMAINS

(75) Inventors: Edward Coulstock, Cambridge (GB); Elena De Angelis, Cambridge (GB); Haiqun Liu, Cambridge (GB); Oliver Schon, Cambridge (GB)

(73) Assignee: Glaxo Group Limited (GB)

( * ) Notice: Subject to any disclaimer, the term of this patent is extended or adjusted under 35 U.S.C. 154(b) by 0 days.

(21) Appl. No.: 13/384,316

(22) PCT Filed: Jul. 14, 2010

(86) PCT No.: PCT/EP2010/060112
§ 371 (c)(1),
(2), (4) Date: Jan. 16, 2012

(87) PCT Pub. No.: WO2011/006915
PCT Pub. Date: Jan. 20, 2011

(65) Prior Publication Data
US 2012/0114647 A1      May 10, 2012

Related U.S. Application Data

(60) Provisional application No. 61/226,028, filed on Jul. 16, 2009, provisional application No. 61/307,554, filed on Feb. 24, 2010.

(51) Int. Cl.
*A61K 39/395*          (2006.01)

(52) U.S. Cl.
USPC ......... 424/133.1; 424/139.1; 424/141.1; 424/145.1; 530/387.3; 530/388.1; 530/388.25

(58) Field of Classification Search
None
See application file for complete search history.

(56) References Cited

U.S. PATENT DOCUMENTS

2009/0297524 A1 * 12/2009 Grant et al. ............... 424/139.1

FOREIGN PATENT DOCUMENTS

| WO | WO 2006030220 A1 * | 3/2006 |
| WO | WO 2007063311 A2 * | 6/2007 |
| WO | WO 2008/096158 A2 | 8/2008 |

OTHER PUBLICATIONS

Janeway et al., Immunobiology, $3^{rd}$ edition , 1997, Garland Publishing Inc., pp. 3:1-3:11.*
Rudikoff et al., Proc Natl Acad Sci U S A. Mar. 1982;79(6):1979-83.*
Jespers et al., Nat Biotechnol. Sep. 22, 2004;(9):1161-5. Epub Aug. 8, 2004.*
Holt et al., Trends Biotechnol. Nov. 21, 2003;(11):484-90.*

* cited by examiner

*Primary Examiner* — Michael Szperka
(74) *Attorney, Agent, or Firm* — Jason C. Fedon; William T. Han

(57) ABSTRACT

The invention relates to improved anti-serum albumin immunoglobulin single variable domains, as well as ligands and drug conjugates comprising such variable domains, compositions, nucleic acids, vectors and hosts.

2 Claims, No Drawings

SEQUENCE LISTING

```
<160> NUMBER OF SEQ ID NOS: 200

<210> SEQ ID NO 1
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 1
gaggtgcagc tgttggagtc tggggggaggc ttggtacagc ctggggggtc cctgcgtctc      60
tcctgtgcag cctccggatt caccttgggg ggtatgtga tgggttgggt ccgccaggct     120
ccagggaagg gtctagagtg gtctcagct attaataggt ttggttcgtc tacatactac     180
gcagactccg tgaagggccg gttcaccatc tcccgcgaca attccaagaa cacgctgtat     240
ctgcaaatga acagcctgcg tgccgaggac accgcggtat attactgtgc gaaaggtagt     300
ttgcggcatt ttgactactg gggtcaggga accctggtca ccgtctcgag c               351

<210> SEQ ID NO 2
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 2
gaggtgcagc tgttggagtc tggggggaggc ttggtacagc ctggggggtc cctgcgtctc      60
tcctgtgcag cctccggatt caccttttggt aattatgcga tggcgtgggt ccgccaggct     120
ccagggaagg gtctagagtg gtctcatcg attgatatgg ttggtattaa gacatactac     180
gcagactccg tgaagggccg gttcaccatc tcccgcgaca attccaagaa cacgctgtat     240
ctgcaaatga acagcctgcg tgccgaggac accgcggtat attactgtgc gaaaggtttt     300
cgtatttttg actactgggg tcagggaacc ctggtcaccg tctcgagc                   348

<210> SEQ ID NO 3
<211> LENGTH: 361
<212> TYPE: DNA
<213> ORGANISM: Artificial Sequence
<220> FEATURE:
```

<223> OTHER INFORMATION: Derived from a Human germline sequence

<400> SEQUENCE: 3

```
gaggtgcagc tgttggagtc tgggggaggc ttggtacagc ctggggggtc cctgcgtctc      60
tcctgtgcag cctccggatt cacctttaag gattatgata tgacttgggt ccgccaggct     120
ccagggaagg gtctagagtg ggtctcaatg atttcttcgt cgggtctttg gacatactac     180
gcagactccg tgaagggccg gttcaccatc tcccgcgaca attccaagaa cacgctgtat     240
ctgcaaatga acagcctgcg tgccgaggac accgcggtat attactgtgc gaaaggtttt     300
aggctgtttc ctcggacttt tgactactgg ggtcagggaa ccctggtcac cgtctcgagc     360
g                                                                    361
```

<210> SEQ ID NO 4
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 4

```
gaggtgcagc tgttggagtc tgggggaggc ttggtacagc ctggggggtc cctgcgtctc      60
tcctgtgcag cctccggatt caccttttcg ctgtatagga tggtgtgggt ccgccaggct     120
ccagggaagg gtctagagtg ggtctcaatg atttctcagt ttggtaatca gacatactac     180
gcagactccg tgaagggccg gttcaccatc tcccgcgaca attccaagaa cacgctgtat     240
ctgcaaatga acagcctgcg tgccgaggac accgcggtat attactgtgc gaaagttagg     300
tcttgggatc agactggtgg tcgtcgtact tttgactact ggggtcaggg aaccctggtc     360
accgtctcga gc                                                        372
```

<210> SEQ ID NO 5
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 5

```
gaggtgcagc tgttggagtc tgggggaggc ttggtacagc ctggggggtc cctgcgtctc      60
tcctgtgcag cctccggatt caccttaat cattatacga tggggtgggt ccgccaggct     120
ccagggaagg gtctagagtg ggtctcattg attcatccga gtggtacggt gacatactac     180
gcagactccg tgaagggccg gttcaccatc tcccgcgaca attccaagaa cacgctgtat     240
ctgcaaatga acagcctgcg tgccgaggac accgcggtat attactgtgc gaaatggagt     300
tcgagggcgt ttgactactg ggtcaggga accctggtca ccgtctcgag c               351
```

<210> SEQ ID NO 6
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 6

```
gaggtgcagc tgttggagtc tgggggaggc ttggtacagc ctggggggtc cctgcgtctc      60
tcctgtgcag cctccggatt caccttgat aataatgcga tggggtgggt ccgccaggct     120
ccagggaagg gtctagagtg ggtctcaact attagtgcga atggtaatgc gacatactac     180
```

```
gcagactccg tgaagggccg gttcaccatc tcccgcgaca attccaagga cacgctgtat    240
ctgcaaatga acagcctgcg tgccgaggac accgcggtat attactgtgc gaaagggttt    300
cgtcggtttg actactgggg tcagggaacc ctggtcaccg tctcgagc                 348
```

<210> SEQ ID NO 7
<211> LENGTH: 355
<212> TYPE: DNA
<213> ORGANISM: Artificial Sequence
<220> FEATURE:
<223> OTHER INFORMATION: Derived from a Human germline sequence

<400> SEQUENCE: 7

```
gaggtgcagc tgttggagtc tgggggaggc ttggtacagc ctggggggtc cctgcgtctc     60
tcctgtacag cctccggatt cacctttagg cattatcgta tggttgggt ccgccaggct    120 ccagggaagg gtctagagtg ggtctcatgg attcgtccgg atggtacgtt tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatcttat    300
atgggtgata ggtttgacta ctggggtcag ggaaccctgg tcaccgtctc gagcg         355
```

<210> SEQ ID NO 8
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 8

```
gaggtgcagc tgttggagtc tgggggaggc ttggtacagc ctggggggtc cctgcgtctc     60
tcctgtgcag cctccggatt cacctttggt aattatccga tgacgtgggt ccgccaggct    120
ccagggaagg gtctggagtg ggtctcaact attagttatg gtggtcttgc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaatggcg    300
attaatggtg ttaggcctag gcggtttgac tactggggtc agggaaccct ggtcaccgtc    360
tcgagc                                                              366
```

<210> SEQ ID NO 9
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 9

```
gaggtgcagc tgttggagtc tgggggaggc ttggtacagc ctggggggtc cctgcgtctc     60
tcctgtgcag cctccggatt cacctttatg gcgtatcaga tggcttgggt ccgccaggct    120
ccagggaagg gtctagagtg ggtctcaact attcatcaga cgggttttc tacatactac    180 gcagactccg tgaagggccg gttcaccatc tcccgcgaca attccaagaa cacgctgtat    240
ctgcaaatga acagcctgcg tgccgaggat accgcggtat attactgtgc gaaagtgcgt    300
tctatgcgtc cttataagtt tgactactgg ggtcagggaa ccctggtcac cgtctcgagc    360
```

<210> SEQ ID NO 10
<211> LENGTH: 348
<212> TYPE: DNA
<213> ORGANISM: Artificial Sequence
<220> FEATURE:

<223> OTHER INFORMATION: Derived from a Human germline sequence

<400> SEQUENCE: 10

| gaggtgcagc tgttggagtc tgggggaggc ttggtacagc ctgggggtc cctgcgtctc | 60 |
| tcctgtgcag cctccggatt cacctttggt gataaggcaa tggggtgggt ccgccaggct | 120 |
| ccagggaagg gtctagagtg ggtctcaacg attagtgctc ctggtaaccg tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaaggtttt | 300 |
| cggaattttg actactgggg tcagggaacc ctggtcaccg tctcgagc | 348 |

<210> SEQ ID NO 11
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 11

| gaggtgcagc tgttggagtc tgggggaggc ttggtacagc ctgggggtc cctgcgtctc | 60 |
| tcctgtgcag cctccggatt cacctttgat gggatgcgta tggttgggt ccgccaggct | 120 |
| ccagggaagg gtctagagtg ggtctcagct attgaggtga atggtcagca tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaaatggct | 300 |
| catcctcagt cggggtggc ttttgactac tggggtcagg gaaccctggt caccgtctcg | 360 |
| agc | 363 |

<210> SEQ ID NO 12
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 12

| gaggtgcagc tgttggagtc tgggggaggc ttggtacagc ctgggggtc cctgcgtctc | 60 |
| tcctgtgcag cctccggatt cacctttacg cctgatgcta tggcgtgggt ccgccaggct | 120 |
| ccagggaagg gtctagagtg ggtctcatcg attggtgtga atggttctcc gacatactac | 180 |
| gcagactccg tgaagggccg gttcaccatc tcccgcgaca attccaggaa cacgctgtat | 240 |
| ctgcaaatga acagcctgcg tgccgaggac accgcggtat attactgtgc gaaaatggct | 300 |
| catcctcagt cggggtggc ttttgactac tggggtcagg gaaccctggt caccgtctcg | 360 |
| agc | 363 |

<210> SEQ ID NO 13
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 13

| gaggtgcagc tgttggagtc tgggggaggc ttggtacagc ctgggggtc cctgcgtctc | 60 |
| tcctgtgcag cctccggatt caccttttat cagtcggata tgtcttgggt ccgccaggct | 120 |
| ccagggaaag gtctagagtg ggtctcatct atttcttctc aggtcgttc tacatactac | 180 |

```
gcagactccg tgaagggccg gttcaccatc tcccgcgaca attccaagaa cacgctgtat    240
ctgcaaatga acagcctgcg tgccgaggac accgcggtat attactgtgc gaaaatggct    300
catcctcagt cggggtggc ttttgactac tggggtcagg gaaccctggt caccgtctcg    360
agc                                                                 363

<210> SEQ ID NO 14
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 14
gaggtgcagc tgttggagtc tgggggaggc ttggtacagc ctgggggtc cctgcgtctc     60 tcctgtacag cctccggatt cacctttgcg gcgagggata tgagttgggt ccgccaggct   120
ccagggaagg gtctggagtg ggtctcaagt atttctgctc aggtgctca tacatactac    180 gcagactccg tgaagggccg gttcaccatc tcccgcgacg attccaagaa cacgctgtat    240
ctgcaaatga acagcctgcg tgccgaggat accgcggtat attactgtgc gaaacctcgg    300
catcctcagg gggggttac ttttgactac tggggtcagg gaaccctggt caccgtctcg    360
agc                                                                 363

<210> SEQ ID NO 15
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 15
gaggtgcagc tgttggagtc tgggggaggc ttggtacagc ctgggggtc cctgcgtctc     60 tcctgtgcag cctccggatt cacctttgat aatggggata tggtttgggt ccgccaggct   120
ccagggaagg gtctagagtg ggtctcaggg attgcgcata atggtcgtaa tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaaatttg    300
ggtcagggtt ttgactactg gggtcaggga accctggtca ccgtctcgag c             351

<210> SEQ ID NO 16
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 16
gaggtgcagc tgttggagtc tgggggaggc ttggtacagc ctgggggtc cctgcgtctc     60 acctgtgcag cctccggatt caccttgaat ggtacgtcga tggggtgggt ccgccaggct   120
ccagggaagg atctagagtg ggtctcatct attatgcctg tggttctca tacatactac    180 gcagactccg tgaagggccg gttcaccatc tcccgcgaca attccaagaa cacgctgtat    240
ctgcaaatga acagcctgcg tgccgaggac accgcggtat attactgtgc gaaaatggct    300
catcctcagt cggggtggc ttttgactac tggggtcagg gaaccctggt caccgtctcg    360
agc                                                                 363

<210> SEQ ID NO 17
```

```
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 17
gaggtgcagc tgttggagtc tgggggaggc ttggtacagc ctgggggtc  cctgcgtctc      60 tcctgtgcag cctccggatt cacctttgat catgcgccta tgaagtgggc  ccgccaggct    120
ccagggaagg gtctagagtg ggtctcatat attgggtcgg cgggtaatat  gacatactac    180
gcagactccg tgaagggccg gttcaccatc tcccgcgaca attccaagaa  cacgctgtat    240
ctgcaaatga acagcctgcg tgccgaggac accgcggtat attactgtgc  gaaagatgag    300
gggccgtttg actactgggg tcagggaacc ctggtcaccg tctcgagc                  348

<210> SEQ ID NO 18
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 18
gaggtgcagc tgttggagtc tgggggaggc ttggtacagc ctgggggtc  cctgcgtctc      60 tcctgtacag cctccggatt cacctttgat gggatggata tgagttgggt  ccgccaggct    120
ccagggaagg gtctagagtg ggtctcaagt atttctacga ctggtgggac  tacatactac    180
gcagactccg tgaagggccg gttcaccatc tcccgcgaca attccaagaa  cacgctgtat    240
ctgcaaatga acagcctgcg tgccgaggac accgcggtat attactgtgc  gaaacctcgg    300
catcctcagg gggggttac ttttgactac tggggtcagg gaaccctggt  caccgtctcg     360
agc                                                                   363

<210> SEQ ID NO 19
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 19
gaggtgcagc tgttggagtc tgggggaggc ttggtacagc ctgggggtc  cctgcgtctc      60 tcctgtgcag cctccggatt cacctttgag gcggagacga tggcttgggt  ccgccaggct    120
ccagggaagg gtctagagtg ggtctcaact attcattcgg agggttctcg  gacatactac    180
gcagactccg tgaagggccg gttcaccatc tcccgcgaca attccaagaa  cacgctgtat    240
ctgcaaatga acagcctgcg tgccgaggac accgcggtat attactgtgc  gaaacctcgg    300
catcctcagg gggggttac ttttgactac tggggtcagg gaaccctggt  caccgtctcg     360
agc                                                                   363

<210> SEQ ID NO 20
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 20
gaggtgcagc tgttggagtc tgggggaggc ttggtacagc ctgggggtc  cctgcgtctc      60
```

```
tcctgtgcag cctccggatt cacctttagt actggggaga tggcttgggt ccgccaggct        120
ccagggaagg gtctagagtg gtctcatct attagttcga gtggtgctac gacatactac         180
gcagactccg tgaagggccg gttcaccatc tcccgcgaca attccaagaa cacgctgtat        240
ctgcaaatga acagcctgcg tgccgaggac accgcggtat attactgtgc gaaacctcgg        300
catcctcagg ggggggttac ttttgactac tggggtcagg gaaccctggt caccgtctcg        360
agc                                                                      363

<210> SEQ ID NO 21
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 21
gaggtgcagc tgttggagtc tgggggaggc ttggtacagc ctggggggtc cctgcgtctc         60
tcctgtgcag cctccggatt cacctttcct agtgctgata tggtttgggt ccgccaggct        120
ccagggaagg gtctagagtg gtctcacgt atttcgcctg agggtaatca tacatactac         180
gcagactccg tgaagggtcg gttcaccatc tcccgcgaca attccaagaa cacgctgtat        240
ctgcaaatga acagcctgcg tgccgaggat accgcggtat attactgtgc ggaacggcct        300
ccttcggatt atgtttcttt tgactactgg ggtcagggaa ccctggtcac cgtctcgagc        360

<210> SEQ ID NO 22
<211> LENGTH: 357
<212> TYPE: DNA
<213> ORGANISM: Artificial Sequence
<220> FEATURE:
<223> OTHER INFORMATION: Derived from a Human germline sequence

<400> SEQUENCE: 22
gaggtgcagc tgttggagtc tgggggaggc ttggtacagc ctggggggtc cctgcgtctc         60
tcctgtgcag cctccggatt cacctttgcg aatgcgacta tgtcgtgggt ccgccaggct        120
ccagggaagg gtctagagtg gtctcagat attgatcagg tgggtcatgc tacatactac         180
gcagactccg tgaagggccg gttcaccatc tcccgcgaca attccaagaa cacgctgtat        240
ctgcaaatga acagcctgcg tgccgaggac accgcggtat attactgtgc gaaatattcg        300
tggcatccgg atctgtttga ctactggggt caggaaccc tggtcaccgt ctcgagc            357

<210> SEQ ID NO 23
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 23
gaggtgcggc tgttggagtc tgggggaggc ttggtacagc ctggggggtc cctgcgtctc         60
tcctgtgcag cctccggatt cacctttaag gattatggga tgaattgggt ccgccaggct        120
ccagggaagg gtctagagtg gtctcacgg attagtagga atggtactgt tacatactac         180
gcagactccg tgaagggccg gttcaccatc tcccgcgaca actccaagaa cacgctgtat        240
ctgcaaatga acagcctgcg tgccgaggac accgcggtat attactgtgc gaaattggct        300
gctccggttc gtcagaaggg gatggatttt gactactggg gtcagggaac cctggtcacc        360
gtctcgagc                                                                369
```

<210> SEQ ID NO 24
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 24

```
gaggtgcagc tgttggagtc tggggaggc ttggtacagc ctggggggtc cctgcgtctc      60
tcctgtgcag cctccggatt cacctttgag tggtataata tgtcgtgggt ccgccaggct    120
ccagggaagg atctggagtg gtctcatcg atttctcatg atggttggaa tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagggatg    300
attggttttg actactgggg tcagggaacc ctggtcaccg tctcgagc                 348
```

<210> SEQ ID NO 25
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 25

```
gaggtgcagc tgttggagtc tggggaggc ttggtacagc ctggggggtc cctgcgtctc      60
tcctgtgcag cctccggatt cacctttgat atttatacga tgcattgggt ccgccaggct    120
ccagggaagg gtctagagtg gtctcaact attgttccgc agggtactcc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatctaag    300
cgtaggtttc ttaagaggtt tgactactgg ggtcagggaa ccctggtcac cgtctcgagc    360
```

<210> SEQ ID NO 26
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 26

```
gaggtgcagc tgttggagtc tggggaggc ttggtacagc ctggggggtc cctgcgtctc      60
tcctgtgcag cctccggatt cacctttgct aggtatgata tgcagtgggt ccgccaggct    120
ccagggaagg gtctagagtg gtctcatcg attaagagta atggtatgaa gacatactac    180
gcagactccg tgaagggccg gttcaccatc tcccgcgaca attccaagaa cacgctgtat    240
ctgcaaatga acagcctgcg tgccgaggac accgcggtat attactgtgc gaaagctagt    300
atgtggacgt ttgactactg ggtcaggga accctggtca ccgtctcgaa c              351
```

<210> SEQ ID NO 27
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 27

```
gaggtgcagc tgttggagtc tggggaggc ttggtacagc ctggggggtc cctgcgtctc      60
tcctgtgcag cctccggatt cacctttatg ttgtatcata tgggttgggt ccgccaggct    120
```

```
ccagggaagg gtctagagtg ggtctcagct attaccgggg ggggttatcc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaactgggg    300
cttcggggtg tgctgtggcg gaggaggttt gactactggg gtcagggaac cctggtcacc    360
gtctcgagc                                                            369

<210> SEQ ID NO 28
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 28
gaggtgcagc tgttggagtc tgggggaggc ttggtacagc ctgggggggtc cctgcgtctc     60 tcctgtgcag cctccggatt cacctttggt gcttattcta tgatgtgggt ccgccaggct    120
ccagggaagg gtctagagtg ggtctcacgg attagtagga atggtactgt tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaattagg    300
tggaatactg ctcaggtgcc tgtgtttgac tactggggtc agggaactct ggtcaccgtc    360
tcgagc                                                               366

<210> SEQ ID NO 29
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 29
gaggtgcagc tgttggagtc tgggggaggc ttggtacagc ctgggggggtc cctgcgtctc     60 tcctgtgcag cctccggatt cacctttggt ccgtattgga tggcttgggt ccgccaggct    120
ccagggaagg gtctagagtg ggtctcaacg attacgcctt cgggtcgtgg gacatactac    180
gcagactccg tgaagggccg gttcaccatc tcccgcgaca attccaagaa cacgctgtat    240
ctgcaaatga acagcctgcg tgccgaggat accgcggtat attactgtgc gaaagggcgt    300
cctcgtgttg gtttgtggag gtcggggttt gactactggg gtcagggaac cctggtcacc    360
gtctcgagc                                                            369

<210> SEQ ID NO 30
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 30
gaggtgcagc tgttggagtc tgggggaggc ttggtacagc ctgggggggtc cctgcgtctc     60 tcctgtgcag cctccggatt cacctttggg cagtatgcta tgcagtgggt ccgccaggct    120
ccagggaagg gtctagagtg ggtctcatct attaatatta ctggttctac tacatactac    180
gcagactccg tgaagggccg gttcaccatc tcccgcgaca attccaagaa cacgctgtat    240
ctgcagatga acagcctgcg tgccgaggac accgcggtat attactgtgc gaaaggttttt    300 aggtctttttg actactgggg tcagggaacc ctggtcaccg tctcgagc                348
```

<210> SEQ ID NO 31
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 31

```
gaggtgcagc tgttggagtc tgggggaggc ttggtacagc ctgggggtc cctgcgtctc      60 tcctgtgcag cctccggatt cacctttgct ggttatacga tgtcgtgggt ccgccaggct     120
ccagggaagg gtctagagtg gtctcaacg atttcgggtt ttggttggac tacatactac     180
gcagactccg tgaagggccg gttcaccatc tcccgcgaca attccaagaa cacgctgtat     240
ctgcaaatga acagcctgcg tgccgaggat accgcggtat attactgtgc gaaaaggctg     300
gggatgcgtt ttgactactg gggtcaggga accctggtca ccgtctcgag c              351
```

<210> SEQ ID NO 32
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 32

```
gaggtgcagc tgttggagtc tgggggaggc ttggtacagc ctgggggtc cctgcgtctc      60 tcctgtgcag cctccggatt cacctttggt ccgtattcga tggggtgggt ccgccaggct     120
ccagggaagg gtctagagtg gtctcatttt attcattctg atggtcgtca tacatactac     180
gcagactccg tgaagggccg gttcaccatc tcccgcgaca attccaagaa cacgctgtat     240
ctgcaaatga acagcctgcg tgccgaggac accgcggtat attactgtgc gaaaagacg      300 ccttataggt ttgactactg gggtcaggga accctggtca ccgtctcgag c              351
```

<210> SEQ ID NO 33
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 33

```
gaggtgcagc tgttggagtc tgggggaggc ttggtacagc ctgggggtc cctgcgtctc      60 tcctgtgcag cctccggatt cacctttggg cagtatgcta tgcagtgggt ccgccaggct     120
ccagggaagg gtctagagtg gtctcatct attaatatta ctggttctac tacatactac     180
gcagactccg tgaagggccg gttcaccatc tcccgcgaca attccaagaa cacgctgtat     240
ctgcagatga acagcctgcg tgccgaggac accgcggtat attactgtgc gaaaggtttt    300
aggtcttttg actactgggg tcagggaacc ctggtcaccg tctcgagc                  348
```

<210> SEQ ID NO 34
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 34

```
gaggtgcagc tgttggagtc tgggggaggc ttggtacagc ctgggggtc cctgcgtctc      60 tcctgtgcag cctccggatt caccttttagg cggtatgcga tgtcttgggt ccgccaggct    120
```

```
ccagggaagg gtctagagtg ggtctcaacg atttcgcctt atggtcctgt tacatactac      180
gcagactccg tgaagggccg gttcaccatc tcccgcgaca attccaagaa cacgctgtat      240
ctgcaaatga atagcctgcg tgccgaggac accgcggtat attactgtgc gaaagcttat      300
tatggtgggt ttgactactg gggtcaggga accctggtca ccgtctcgag c               351
```

<210> SEQ ID NO 35
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 35

```
gaggtgcagc tgttggagtc tgggggaggc ttggtacagc ctgggggtc cctgcgtctc       60 tcctgtgcag cctccggatt cacctttgat gcttatgcta tgggttgggt ccgccaggct     120
ccagggaagg gtctagagtg ggtctcaaag attgattctc tggttggag acatactac       180 gcagactccg tgaagggccg gttcaccatc tcccgcgaca attccaagaa cacgctgtat     240
ctgcaaatga acagcctgcg tgccgaggac accgcggtat attactgtgc gaaatcggct    300
cggatgcgtt ctcggcattt tgactactgg ggtcagggaa ccctggtcac cgtctcgagc    360
```

<210> SEQ ID NO 36
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 36

```
gaggtgcagc tgttggagtc tgggggaggc ttggtacagc ctgggggtc cctgcgtctc       60 tcctgtgcag cctccggatt cacctttaag gattatggga tgaattgggt ccgccaggct    120
ccagggaagg gtctagagtg ggtctcacgg attagtagga atggtactgt tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaattagg    300
tggaatactg ctcaggtgcc tgtgtttgac tactggggtc agggaactct ggtcaccgtc    360
tcgagc                                                                366
```

<210> SEQ ID NO 37
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 37

```
gaggtgcagc tgttggagtc tgggggaggc ttggtacagc ctgggggtc cctgcgtctc       60 tcctgtgcaa cctccggatt cacctttccg tcttatacga tgggttgggt ccgccaggct    120
ccagggaagg gtctagagtg ggtctcacgt atttctcgta ctgggaatta tacatactac    180
gcagactccg tgaagggccg gttcaccatc tcccgcgaca attccaagaa cacgctgtat    240
ctgcaaatga acagcctgcg tgccgaggat accgcggtat attactgtgc gaaacctatg    300
tataataggg ggtcttcgta ttttgactac tggggtcagg gaaccctggt caccgtctcg    360
agc                                                                    363
```

<210> SEQ ID NO 38

```
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 38
gaggtgcagc tgttggagtc tgggggaggc ttggtacagc ctgggggtc cctgcgtctc        60 tcctgtgcag cctccggatt cacctttccg cagtatcaga tgtcgtgggt ccgccaggct      120
ccagggaagg gtctagagtg ggtctcatcg atttcgccta cgggtattca gacatactac      180
gcagactccg tgaagggccg gttcaccatc tcccgcgaca attccaagaa cacgctgtat      240
ctgcaaatga acagcctgcg tgccgaggac accgcggtat attactgtgc gaaaaggctt      300
attgggatgc cgtatgttga ggatactttt gactactggg gtcagggaac cctggtcacc      360
gtctcgagc                                                              369

<210> SEQ ID NO 39
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 39
gaggtgcagc tgttggagtc tgggggaggc ttggtacagc ctgggggtc cctgcgtctc        60 tcctgtgcag cctccggatt cacctttatg gagtatgaga tggagtgggt ccgccaggct      120
ccagggaagg gtctagagtg ggtctcaggt attactaatt ctggttctgg gacatactac      180
gcagactccg tgaagggccg gttcaccatc tcccgcgaca actccaagaa cacgctgtat      240
ctgcaaatga acagcctgcg tgccgaggac accgcggtat attactgtgc gataatgcag      300
catcctcagg cgactggggg gagggttggg tttgactact ggggtcaggg aaccctggtc      360
accgtctcga gc                                                          372

<210> SEQ ID NO 40
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 40
gaggtgcagc tgttggagtc tgggggaggc ttggtacagc ctgggggtc cctgcgtctc        60 tcctgtgcag cctccggatt cacctttccg aggtatacta tgaagtgggt ccgccaggct      120
ccagggaagg gtctagagtg ggtctcatcg attgatagga cgggtcgtaa gacatactac      180
gcagactccg tgaagggccg gttcaccatc tcccgcgaca attccaagaa cacgctgtat      240
ctgcaaatga acagcctgcg tgccgaggat accgcggtat attactgtgc gaaagagtcg      300
ttggtttcgt ttgactactg gggtcaggga accctggtca ccgtctcgag c               351

<210> SEQ ID NO 41
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 41
gaggtgcagc tgttggagtc tgggggaggc ttggtacagc ctgggggtc cctgcgtctc        60
```

```
tcctgtgcag cctccggatt cacctttggt ggttatacga tgccttgggt ccgccaggct    120
ccagggaagg gtctagagtg ggtctcaact atttctcgtg atggtaatta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatatt    300
ggtatgggtt ttgactacgg ggggcgggga accctggtca ccgtctcgag c             351
```

<210> SEQ ID NO 42
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 42

```
gaggtgcagc tgttggagtc tgggggaggc ttggtacagc ctggggggtc cctgcgtctc     60
tcctgtgcag cctccggatt cacctttgag atttatgcga tgcattgggt ccgccaggct    120
ccagggaagg gtctagagtg ggtctcaacg attagttcgg gtggtaaggg gacatactac    180
gcagactccg tgaagggccg gttcaccatc tcccgcgaca attccaagaa cacgctgtat    240
ctgcaaatga acagcctgcg tgccgaggac accgcggtat attactgtgc gaaatcgcgt    300
actatgtatt ttcgtgttag ggaggctttt gactactggg gtcagggaac cctggtcacc    360
gtctcgagc                                                            369
```

<210> SEQ ID NO 43
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 43

```
gaggtgcagc tgttggagtc tgggggaggc ttggtacagc ctggggggtc cctgcgtctc     60
tcctgtgcag cctccggatt cacctttcgt gcttatagga tgatgtgggt ccgccaggct    120
ccagggaagg gtctggagtg ggtctcatct attgatcctg atggtgcggt tacatactac    180
gcagactccg tgaagggccg gttcaccatc tcccgcgaca attccaagaa cacgctgtat    240
ctgcaaatga acagcctgcg tgccgaggac accgcggtat attactgtgc ggaacatttt    300
gatcttgcga tgccgaatcc gaatgcgaag tttgactact ggggtcaggg aaccctggtc    360
accgtctcga gc                                                        372
```

<210> SEQ ID NO 44
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 44

```
gaggtgcagc tgttggagtc tgggggaggc ttggtacagc ctggggggtc cctgcgcctc     60
tcctgtgcag cctccggatt caccttttct cgttatcaga tgtcttgggt ccgccaggct    120
ccagggaagg gtctggagtg ggtctcatct attaagtcga atggttcttc gacatactac    180
gcagactccg tgaagggccg gttcaccatc tcccgcgaca attccaagaa cacgctgtat    240
ctgcaaatga acagcctgcg tgccgaggac accgcggtat attactgtgc gaaacctagt    300
cggcagagtt ttcagtatcc gagttttgac tactggggtc agggaaccct ggtcaccgtc    360
``` tcgagc                                                              366

<210> SEQ ID NO 45
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 45
gaggtgcagc tgttggagtc tgggggaggc ttggtacagc ctggggggtc cctgcgtctc    60
tcctgtgcag cctccggatt cacctttggg cgttataaga tgggttgggt ccgccaggct   120
ccagggaagg gtctagagtg ggtctcatct atttcgccta cgggttcgtc tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaactggg   300
tatgttatgg ttgagcattt tgactactgg ggtcagggaa ccctggtcac cgtctcgagc   360

<210> SEQ ID NO 46
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 46
gaggtgcagc tgttggagtc tgggggaggc ttggtacagc ctggggggtc cctgcgtctc    60
tcctgtgcag cctccggatt cacctttagt gattatccga tgaagtgggt ccgccaggct   120
ccagggaagg gtctggagtg ggtctcaact attaattctt cgggtacgat tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaccgttg   300
ttgccgtttg actactgggg tcagggaacc ctggtcaccg tctcgagc                348

<210> SEQ ID NO 47
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 47
gaggtgcagc tgttggagtc tgggggaggc ttggtacagc ctggggggtc cctgcgtctc    60
tcctgtgcag cctccggatt cacctttgct aggtatagga tgtgttgggt ccgccaggct   120
ccagggaagg gtctagagtg ggtctcatgt attcgggatc cgggttttcc gacatactac   180
gcagactccg tgaagggccg gttcaccatc tcccgcgaca attccaagaa cacgctgtat   240
ctgcaaatga acagcctgcg tgccgaggac accgcggtat attactgtgc gaatgttcg    300 ccgtcttcta cgcagtgtac ggggcttttt gactactggg gtcagggaac cctggtcacc   360
gtctcgagc                                                           369

<210> SEQ ID NO 48
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 48

```
gaggtgcagc tgttggagtc tggggagggc ttggtacagc ctgggggggtc cctgcgtctc    60 tcctgtgcag cctccggatt cacctttagg ttttatggga tggcgtgggt ccgccaggct   120
ccagggaagg gtctagagtg ggtctcactt attgatcctc ctggtggggc gacatactac   180
gcagactccg tgaagggccg gttcaccatc tcccgcgaca attccaagaa cacgctgtat   240
ctgcaaatga acagcctgcg tgccgaggac accgcggtat attactgtgc gaaaatggag   300
aggcggcatc ttaagagtgg tcataagggg tttgactact ggggtcaggg aaccctggtc   360
accgtctcga gc                                                       372

<210> SEQ ID NO 49
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 49
gaggtgcagc tgttggagtc tggggaggc ttggtacagc ctgggggggtc cctgcgtctc    60 tcctgtgcag cctccggatt cacctttacg gagtatgata tgatgtgggt ccgccaggct   120
ccagggaagg gtctagagtg ggtctcatct attagtcata ggggtgagaa gacatactac   180
gcagactccg tgaagggccg gttcaccatc tcccgcgaca attccaagaa cacgctgtat   240
ctgcaaatga acagcctgcg tgccgaggac accgcggtat attactgtgc gaaagataag   300
cgttatcggg ggtctcagca ttattttgac tactggggtc agggaaccct ggtcaccgtc   360
tcgagc                                                              366

<210> SEQ ID NO 50
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 50
gaggtgcagc tgttggagtc tggggaggc ttggtacagc ctgggggggtc cctgcgtctc    60 tcctgtgcag cctccggatt cacctttcgg agttatgata tgggttgggc ccgccaggct   120
ccagggaagg gtctagagtg ggtctcaact attgggtcga atggtgctaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaacttatg   300
ggtatgtttg actactgggg tcagggaacc ctggtcaccg tctcgagc                348

<210> SEQ ID NO 51
<211> LENGTH: 354
<212> TYPE: DNA
<213> ORGANISM: Artificial Sequence
<220> FEATURE:
<223> OTHER INFORMATION: Derived from a Human germline sequence

<400> SEQUENCE: 51
gaggtgcagc tgttggagtc tggggaggc ttggtacagc ctgggggggtc cctgcgtctc    60 tcctgtgcag cctccggatt cacctttgag cgttattcta tgaggtgggt ccgccaggct   120
ccagggaagg gtctagagtg ggtctcaacg attggttcga cgggtaagtg gacatactac   180
gcagactccg tgaagggccg gttcaccatc tcccgcgaca attccaagaa cacgctgtat   240
ctgcaaatga acagcctgcg tgccgaggac accgcggtat attactgtgc gaaagggcgt   300
```

```
gggttggttt cttttgacta ctggggtcag ggaaccctgg tcaccgtctc gagc         354
```

<210> SEQ ID NO 52
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 52

```
gaggtgcagc tgttggagtc tgggggaggc ttggtacagc ctgggggtc cctgcgtctc     60
tcctgtgcag cctccggatt cacctttagg cgttattcga tgtcttgggt ccgccaggct   120
ccagggaagg gtctagagtg gtctcatct attgatcggt ctggtaggat gacatactac   180
gcagactccg tgaagggccg gttcaccatc tcccgcgaca attccaagaa cacgctgtat  240
ctgcaaatga acagcctgcg tgccgaggac accgcggtat attactgtgc gaaatctcgg  300
ctgtcttcga cgggttctga gggtcataat tttgactact ggggtcaggg aaccctggtc  360
accgtctcga gc                                                      372
```

<210> SEQ ID NO 53
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 53

```
gaggtgcagc tgttggagtc tgggggaggc ttggtacagc ctgggggtc cctgcgtctc     60
tcctgtgcag cctccggatt cacctttaag tggtatccga tgaagtgggt ccgccaggct  120
ccagggaagg gtctagagtg gtctcaact attgcttatg atggtgttca gacatactac  180
gcagactccg tgaagggccg gttcaccatc tcccgcgaca attccaagaa cacgctgtat  240
ctgcaaatga acagcctgcg tgccgaggac accgcggtat attactgtgc gaaattgggt  300
ccgactagtc gtgtgtttgc tgctactgat tttgactact ggggtcaggg aaccctggtc  360
accgtctcga gc                                                      372
```

<210> SEQ ID NO 54
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 54

```
gaggtgcagc tgttggagtc tgggggaggc ttggtacagc ctgggggtc cctgcgtctc     60
tcctgtgcag cctccggatt cacctttccg aattatgcga tgaagtgggg ccgccaggct  120
ccagggaagg gtctagagtg gtctcaact attgatacga gtggtagtac tacatactac  180
gcagactccg tgaagggccg gttcaccatc tcccgcgaca attccaagaa cacgctgtat  240
ctgcaaatga acagcctgcg tgccgaggac accgcggtat attactgtgc gaaacttact  300
catcctatgg cgccgcgtcc ggcttttgac tactggggtc agggaaccct ggtcaccgtc  360
tcgagc                                                              366
```

<210> SEQ ID NO 55
<211> LENGTH: 366
<212> TYPE: DNA
<213> ORGANISM: Artificial Sequence
<220> FEATURE:

<223> OTHER INFORMATION: Derived from a Human germline sequence

<400> SEQUENCE: 55

```
gaggtgcagc tgttggagtc tggggggaggc ttggtacagc ctgggggggtc cctgcgtctc    60
tcctgtgcag cctccggatt cacctttgat cttacgaga tggagtgggt ccgccaggct     120
ccagggaagg gtctggagtg ggtctcatcg attgggcctt ggggtactcc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatttcg     300
catcctcagg cgatgtatca tacgtttgac tactggggtc agggaaccct ggtcaccgtc    360
tcgagc                                                               366
```

<210> SEQ ID NO 56
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 56

```
gaggtgcagc tgttggagtc tggggggaggc ttggtacagc ctgggggggtc cctgcgtctc    60
tcctgtgcag cctccggatt cacctttgcg catcaggata tgacgtgggt ccgccaggct    120
ccagggaagg gtctagagtg gtctcagat attgatcatt cgggttcgta tacatactac     180
gcagactccg tgaagggccg gttcaccatc tcccgcgaca attccaagaa cacgctgtat    240
ctgcaaatga acagcctgcg tgccgaggac accgcggtat attactgtgc gaaatggtgg    300
catccgcagg gggggacttt tgactactgg ggtcagggaa ccctggtcac cgtctcgagc    360
```

<210> SEQ ID NO 57
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 57

```
gaggtgcagc tgttggagtc tggggggaggc ttggtacagc ctgggggggtc cctgcgtctc    60
tcctgtgcag cctccggatt cacctttggt tctaaggata tgtcgtgggt ccgccaggct    120
ccagggaagg gtctagagtg gtctcaacg attggggcga atggtaaggc tacatactac    180
gcagactccg tgaagggccg gttcaccatc tcccgcgaca attccaagaa cacgctgtat    240
ctgcaaatga acagcctgcg tgccgaggac accgcggtat attactgtgc ggaagcgggt    300
catcctcagg cgccgtcttt taagagtttt gactactggg gtcagggaac cctggtcacc    360
gtctcgagc                                                            369
```

<210> SEQ ID NO 58
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 58

```
gaggtgcagc tgttggagtc tggggggaggc ttggtacagc ctgggggggtc cctgcgtctc    60
tcctgtgcag cctccggatt cacctttctg aatgcggaga tgagttgggt ccgccaggct    120
ccagggaagg gtctagagtg gtctcaact attgatcggg atggtgctaa tacatactac    180
```

```
gcagactccg tgaagggccg gttcaccatc tcccgcgaca attccaagaa cacgctgtat      240
ctgcaaatga acagcctgcg tgccgaggac accgcggtat attactgtgc gaaacttcct      300
ccgccgatgt cgccgaagaa gtttgactac tggggtcagg gaaccctggt caccgtctcg      360
agc                                                                    363

<210> SEQ ID NO 59
<211> LENGTH: 357
<212> TYPE: DNA
<213> ORGANISM: Artificial Sequence
<220> FEATURE:
<223> OTHER INFORMATION: Derived from a Human germline sequence

<400> SEQUENCE: 59
gaggtgcagc tgttggagtc tgggggaggc ttggtacagc ctgggggtc cctgcgtctc        60 tcctgtgcag cctccggatt cacctttgag agggagggta tgatgtgggt ccgccaggct      120
ccagggaagg gtctagagtg ggtttcaact attgatcgta tgggtaggta tacatactac      180
gcagactccg tgaagggccg gttcaccatc tcccgcgaca attccaagaa cacgctgtat      240
ctgcaaatga acagcctgcg tgccgaggac accgcggtat attactgtgc gaaagggat       300 tcgcatccta tggggtttga ctaccggggt cagggaaccc tggtcaccgt ctcgagc         357

<210> SEQ ID NO 60
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 60
gaggtgcagc tgttggagtc tgggggaggc ttggtacagc ctgggggtc cctgcgtctc        60 tcctgtgcag cctccgggtt cacctttgag aatgagaaga tgagttgggt ccgccaggct      120
ccagggaagg gtctagagtg ggtctcatcg attggtccta cgggtagtgg tacatactac      180
gcagactccg tgaagggccg gttcaccatc tcccgcgaca attccaagaa cacgctgtat      240
ctgcaaatga acagcctgcg tgccgaggac accgcggtat attactgtgc gaaaactcct     300
catccgcagg tttctagttt tgactactgg ggtcagggaa ccctggtcac cgtctcgagc      360

<210> SEQ ID NO 61
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 61
gaggtgcagc tgttggagtc tgggggaggc ttggtacagc ctgggggtc cctgcgtctc        60 tcctgtgcag cctccggatt cacctttgag attgatcata tgggtgggt ccgccaggct       120 ccagggaagg gtctagagtg ggtctcagag attgcgcctt cgggtgatcg tacatactac      180
gcagactccg tgaagggccg gttcaccatc tcccgcgaca attccaagaa cacgctgtat      240
ctgcaaatga acagcctgcg tgccgaggat accgcggtat attactgtgc gaaagtgatt     300
tgtcagaatc agtgtctgtt tgactactgg ggtcagggaa ccctggtcac cgtctcgagc      360

<210> SEQ ID NO 62
<211> LENGTH: 360
<212> TYPE: DNA
<213> ORGANISM: Artificial Sequence
<220> FEATURE:
```

<223> OTHER INFORMATION: Derived from a Human germline sequence

<400> SEQUENCE: 62

```
gaggtgcagc tgttggagtc tgggggaggc ttggtacagc ctgggggtc cctgcgtctc      60
tcctgtgcag cctccggatt cacctttagg gattctgaga tgtcgtgggt ccgccaggct    120
ccagggaagg gtctagagtg ggtctcattt attacttctg atggtcggga tacatactac    180
gcagactccg tgaagggccg gttcaccatc tcccgcgaca attccaagaa cacgctgtat    240
ctgcaaatga acagcctgcg tgccgaggac accgcggtat attactgtgc gaaacctagt    300
ctgcctcatg ttacggcttt tgactactgg ggtcagggaa ccctggtcac cgtctcgagc    360
```

<210> SEQ ID NO 63
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 63

```
gaggtgcagc tgttggagtc tgggggaggc ttggtacagc ctgggggtc cctgcgtctc      60
tcctgtgcag cctccggatt cacctttgag gatgagacga tgagttgggc ccgccaggct    120
ccagggaagg gtctagagtg ggtctcatcg attgggatg ctggtatgcc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaggggag    300
ccgatttatg ttcatacgac tcattttgac tactggggtc agggaaccct ggtcaccgtc    360
tcgagc                                                              366
```

<210> SEQ ID NO 64
<211> LENGTH: 357
<212> TYPE: DNA
<213> ORGANISM: Artificial Sequence
<220> FEATURE:
<223> OTHER INFORMATION: Derived from a Human germline sequence

<400> SEQUENCE: 64

```
gaggtgcagc tgttggagtc tgggggaggc ttggtacagc ctgggggtc cctgcgtctc      60
tcctgtgcag cctccggatt cacctttccg catggtaaga tggggtgggt ccgccaggct    120
ccagggaagg gtctagagtg ggtctcatgg attgctgggt ctggtgatat gacatactac    180
gcagactccg tgaagggccg gttcaccatc tcccgcgaca attccaagaa cacgctgtat    240
ctgcaaatga acagcctgcg tgccgaggac accgcggtat attactgtgc gaaattgggt    300
catcctcagc ggggttttga ctactggggt cagggaaccc tggtcaccgt ctcgagc      357
```

<210> SEQ ID NO 65
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 65

```
gaggtgcagc tgttggagtc tgggggaggc ttggtacagc ctgggggtc cctgcgtctc      60
tcctgtgcag cctccggatt cacctttggg acttctgata tgtcgtgggt ccgccaggcc    120
ccagggaagg gtctagagtg ggtctcaact attgattctg ggggtagttt tacatactac    180
gcagactccg tgaagggccg gttcaccatc tcccgcgaca attccaagaa cacgctgtat    240
```

```
ctgcaaatga acagcctgcg tgccgaggac accgcggtat attactgtgc gaaacctcgg    300
catcctcagg gggggttac ttttgactac tggggtcagg gaaccctggt caccgtctcg    360
agc                                                                   363
```

<210> SEQ ID NO 66
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 66

```
gaggtgcagc tgttggagtc tgggggaggc ttggtacagc ctgggggtc cctgcgtctc     60 tcctgtgcag cctccggatt cacctttgag catgttccta tggcttgggt ccgccaggct   120
ccagggaagg gtctagagtg gtctcacgg attagtgagc agggtagtaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagtgcag   300
catcctatgt ctccgcatga gtttgactac tggggtcagg gaaccctggt caccgtctcg   360
agc                                                                   363
```

<210> SEQ ID NO 67
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 67

```
gaggtgcagc tgttggagtc tgggggaggc ttggtacagc ctgggggtc cctgcgtctc     60 tcctgtgcag cctccggatt cacctttgag cagggtatga gtcgtgggt ccgccaggct   120 ccagggaagg gtctagagtg gtctcatcg attaatcctg gtggtcagtt tacatactac   180
gcagactccg tgaagggccg gttcaccatc tcccgcgaca attccaggaa cacgctgtat   240
ctgcaaatga acagcctgcg tgccgaggac accgcggtat attactgtgc ggaagatctg   300
gggccgggtt ttgactactg gggtcaggga accctggtca ccgtctcgag c             351
```

<210> SEQ ID NO 68
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 68

```
gaggtgcagc tgttggagtc tgggggaggc ttggtacagc ctgggggtc cctgcgtctc     60 tcctgtgcag cctccggatt cacctttgag cgttggccta tgtcttgggt ccgccaggct   120
ccagggaagg gtctagagtg gtctcaact attgataggt ctggtaatac tacatactac   180
gcagactccg tgaagggccg gttcaccatc tcccgcgaca attccaagaa cacgctgtat   240
ctgcaaatga acagcctgcg tgccgaggat accgcggtat attactgtgc gaaagttttg   300
catcctcagg cggggtctgc ttttgactac tggggtcagg gaaccctggt caccgtctcg   360
agc                                                                   363
```

<210> SEQ ID NO 69
<211> LENGTH: 363
<212> TYPE: DNA

<213> ORGANISM: Artificial Sequence
<220> FEATURE:
<223> OTHER INFORMATION: Derived from a Human germline sequence

<400> SEQUENCE: 69

```
gaggtgcagc tgttggagtc tgggggaggc tcggtacagc ctgggggtc  cctgcgtctc    60
tcctgtgcag cctccggatt cacctttggg ggtagtgata tgggttgggt ccgccaggct   120
ccagggaagg gtctagagtg ggtctcatat attgataatc agggttataa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaatataag   300
cttctgggtc cgtctactga gtttgactac tggggtcagg gaaccctggt caccgtctcg   360
agc                                                                 363
```

<210> SEQ ID NO 70
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 70

```
gaggtgcagc tgttggagtc aggggaggc ttggtacagc ctgggggtc  cctgcgtctc     60
tcctgtgcag cctccggatt cacctttagt agtgatgtta tgtcttgggt ccgccaggct   120
ccagggaagg gtctagagtg ggtctcaagt attacgaggt cgggtatgca gacatactac   180
gcagactccg tgaagggccg gttcaccatc tcccgcgaca attccaagaa cacgctgtat   240
ctgcaaatga acagcctgcg tgccgaggac accgcggtat attactgtgc gaaatatgcg   300
catcctcagt cggctgttga gtttgactac tggggtcagg gaaccctggt caccgtctcg   360
agc                                                                 363
```

<210> SEQ ID NO 71
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 71

```
gaggtgcagc tgttggagtc tgggggaggc ttggtacagc ctgggggtc  cctgcgtctc    60
tcctgtgcag cctccggatt cacctttcgt aatgagccga tgagttgggt cgccaggct   120
ccagtgaagg gtctagagtg ggtctcaact atttcgcctg atggtagtgg gacatactac   180
gcagactccg tgaagggccg gttcaccatc tcccgcgaca attccaagaa cacgctgtat   240
ctgcaaatga acagcctgcg tgccgaggac accgcggtat attactgtgc gaaacatggt   300
catcctcagg gggctcgttt tgactactgg ggtcagggaa ccctggtcac cgtctcgagc   360
```

<210> SEQ ID NO 72
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 72

```
gaggtgcagc tgttggagtc tgggggaggc ttggtacagc ctgggggtc  cctgcgtctc    60
tcctgtgcag cctccggatt cacctttttg aatagtgaga tgtcgtgggt ccgccaggct   120
```

```
ccagggaagg gtctggagtg ggtctcaact attgggtatg cgggtactcc tacatactac      180
gcagactccg tgaagggccg gttcaccatc tcccgcgaca attccaagaa cacgctgtat      240
ctgcaaatga acagcctgcg tgccgaggac accgcggtat attactgtgc gaaacctcgg      300
catcctcagg gggggttac ttttgactac tggggtcagg gaaccctggt caccgtctcg      360
agc                                                                    363
```

<210> SEQ ID NO 73
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 73

```
gaggtgcagc tgttggagtc tgggggaggc ttggtacagc ctgggggggtc cctgcgtctc      60 tcctgtgcag cctccggatt cacctttgct cgggggccta tgtcttgggt ccgccaggct     120
ccagggaagg gtctagagtg gtctcaact attacgaatg atggtacgtc tacatactac      180
gcagactccg tgaagggccg gttcaccatc tcccgcgaca attccaagaa cacgctgtat      240
ctgcaaatga acagcctgcg tgccgaggac accgcggtat attactgtgc ggaaccgcct     300
catagtggta ggcctatgtt tgactactgg ggtcagggaa ccctggtcac cgtctcgagc     360
```

<210> SEQ ID NO 74
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 74

```
gaggtgcagc tgttggagtc tgggggaggc ttggtacagc ctgggggggtc cctgcgtctc      60 tcctgtgcag cctccggatt cacctttcag cggactgcta tgtcttgggt ccgccaggct     120
ccagggaagg gtcttgagtg gtctctcatct attgaggctt cgggtcggta tacatactac    180
gcagactccg tgaagggccg gttcaccatc tcccgcgaca attccaagaa cacgctgtat      240
ctgcaaatga acagcctgcg tgccgaggac accgcggtat attactgtgc gaaacagtcg     300
catcctcaga atggtcgttt tgactactgg ggtcagggaa ccctggtcac cgtctcgagc    360
```

<210> SEQ ID NO 75
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 75

```
gaggtgcagc tgttggagtc tgggggaggc ttggtacagc ctgggggggtc cctgcgtctc      60 tcctgtgcag cctccggatt cacctttgat gcgtcggaga tggcttgggt ccgccaggct     120
ccagggaagg gtctagagtg gtctcaagt attacggttt atggtgatag gacatactac      180
gcagactccg tgaagggccg gttcaccatc tcccgcgaca attccaagaa cacgctgtat      240
ctgcaaatga acagcctgcg tgccgaggac accgcggtat attactgtgc gaaacctcgg      300
catcctcagg gggggttac ttttgactac tggggtcagg gaaccctggt caccgtctcg      360
agc                                                                    363
```

<210> SEQ ID NO 76

```
<211> LENGTH: 357
<212> TYPE: DNA
<213> ORGANISM: Artificial Sequence
<220> FEATURE:
<223> OTHER INFORMATION: Derived from a Human germline sequence

<400> SEQUENCE: 76
gaggtgcagc tgttggagtc tgggggaggc ttggtacagc ctgggggtc cctgcgtctc       60 tcctgtgcag cctccggatt cacctttgat gattcgcata tggcttgggt ccgccaggct     120
ccagggaagg gtctagagtg ggtctcaagg atttcgaggg agggtaaggc gacatactac     180
gcagactccg tgaagggccg gttcaccatc tcccgcgaca attccaagaa cacgctgtat     240
ctgcaaatga acagcctgcg tgccgaggac accgcggtat attactgtgc ggcaccgaat     300
gatcagtcgg cggcttttga ctactgggg cagggaaccc tggtcaccgt ctcgagc        357

<210> SEQ ID NO 77
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 77
gaggtgcagc tgttggagtc tgggggaggc ttggtacagc ctgggggtc cctgcgtctc       60 tcctgtgcag cctccggatt cacctttgat atgagtgaga tgtcgtgggt ccgccaggct     120
ccagggaagg gtctagagtg ggtctcagct attacttcgg atggtagttc tacatactac     180
gcagactccg tgaagggccg gttcaccatc tcccgcgaca attccaagaa cacgctgtat     240
ctgcaaatga acagcctgcg tgccgaggac accgcggtat attactgtgc gaaacctagt     300
ctgcctcatg ttacggcttt tgactactgg ggtcaggaa ccctggtcac cgtctcgagc      360

<210> SEQ ID NO 78
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 78
gaggtgcagc tgttggagtc tgggggaggc ttggtacagc ctgggggtc cctgcgtctc       60 tcctgtgcag cctccggatt cacctttgag aggtctacta tgcattgggt ccgccaggct     120
ccagggaagg gtctagagtg ggtctcagag attgatgctc tgggtacgga tacatactac     180
gcagactccg tgaagggccg gttcaccatc tcccgcgaca attccaagaa cacgctgtat     240
ctgcaaatga acagcctgcg tgccgaggac accgcggtat attactgtgc gaaatcgtct     300
gatcatcctc agaatagttt tgactactgg ggtcaggga ccctggtcac cgtctcgagc     360

<210> SEQ ID NO 79
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 79
gaggtgcagc tgttggagtc tgggggaggc ttggtacagc ctgggggtc cctgcgtctc       60 tcctgtgcag cctccggatt cacctttgag cctcgtgaga tgtattgggc ccgccaggct     120
ccagggaagg gtctagagtg ggtcgcacgg attggttggg atggtcatac gacatactac     180
```

-continued

| | |
|---|---|
| gcagactccg tgaagggccg gttcaccatc tcccgcgaca attccaagaa cacgctgtat | 240 |
| ctgcaaatga acagcctgcg tgccgaggac accgcggtat attactgtgc gaaacagctg | 300 |
| ggtcagtttg actactgggg tcagggaacc ctggtcaccg tctcgagc | 348 |

<210> SEQ ID NO 80
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 80

| | |
|---|---|
| gaggtgcagc tgttggagtc tgggggaggc ttggtacagc ctggggggtc cctgcgtctc | 60 |
| tcctgtgcag cctccggatt cacctttgat gcttatagta tgatgtgggt ccgccaggct | 120 |
| ccagggaagg gtctagagtg ggtctcaact attggtaggt ggggtgagat tacatactac | 180 |
| gcagactccg tgaagggccg gttcaccatc tcccgcgaca attccaagaa cacgctgtat | 240 |
| ctgcaaatga acagcctgcg tgccgaggat accgcggtat attactgtgc gaaacgtcgt | 300 |
| tatattgggc cttatatgct ttcgggtcgt tttgactact ggggtcaggg aaccctggtc | 360 |
| accgtctcga gc | 372 |

<210> SEQ ID NO 81
<211> LENGTH: 372
<212> TYPE: DNA
<213> ORGANISM: Artificial Sequence
<220> FEATURE:
<223> OTHER INFORMATION: Derived from a Human germline sequence

<400> SEQUENCE: 81

| | |
|---|---|
| gaggtgcagc tgttggagtc tgggggaggc ttggtacagc ctggggggtc cctgcgtctc | 60 |
| tcctgtgcag cctccggatt cacctttatg cggtatccta tggtgtgggt ccgccaggct | 120 |
| ccagggaggg gtctagagtg gtctcatct atttctcctg ctggttatgg tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaaggtcat | 300 |
| gagattagtc ggttttctcg ttggtcttct tttgactact ggggtcaggg aaccctggtc | 360 |
| accgtctcga gc | 372 |

<210> SEQ ID NO 82
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 82

| | |
|---|---|
| gaggtgcagc tgttggagtc tggggggggc ttggtacagc ctggggggtc cctgcgtctc | 60 |
| tcctgtgcag cctccggatt cacctttcgg aagtatagga tgtcgtgggt ccgccaggct | 120 |
| ccagggaagg gtctagagtg gtctcatct attgcgagga atggtcgttc tacatactac | 180 |
| gcagactccg tgaagggccg gttcaccatc tcccgcgaca attccaagaa cacgctgtat | 240 |
| ctgcaaatga acagcctgcg tgccgaggac accgcggtat attactgtgc gaaaactacg | 300 |
| tctggttttg actactgggg tcagggaacc ctggtcaccg tctcgagc | 348 |

<210> SEQ ID NO 83
<211> LENGTH: 363
<212> TYPE: DNA

```
<213> ORGANISM: Artificial Sequence
<220> FEATURE:
<223> OTHER INFORMATION: Derived from a Human germline sequence

<400> SEQUENCE: 83
gaggtgcagc tgttggagtc tggggaggc ttggtacagc ctgggggtc cctgcgtctc      60 tcctgtgcag cctccggatt cacctttaat aagaaggaga tgggttgggt ccgccaggct    120
ccagggaagg gtctagagtg ggtctcatct attgatgtga gtggtaatgt tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaatggct    300
catcctcagt cgggggtggc ttttgactac tggggtcagg gaaccctggt caccgtctcg    360
agc                                                                  363

<210> SEQ ID NO 84
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 84
gaggtgcagc tgttggagtc tggggaggc ttggtacagc ctgggggtc cctgcgtctc      60 tcctgtgcag cctccggatt cacctttcgg atgtatgata tggcgtgggt ccgccaggct    120
ccagggaagg gtctaaagtg ggtctcaact attctgtctt ctggtaaggg tacatactac    180
gcagactccg tgaagggccg gttcaccatc tcccgcgaca attccaagaa cacgctgtat    240
ctgcaaatga acagcctgcg tgccgaggac accgcggtat attactgtgc gaaattggct    300
catcctcaga agggtagtat ttttgactac cggggtcagg gaaccctggt caccgtctcg    360
agc                                                                  363

<210> SEQ ID NO 85
<211> LENGTH: 363
<212> TYPE: DNA
<213> ORGANISM: Artificial Sequence
<220> FEATURE:
<223> OTHER INFORMATION: Derived from a Human germline sequence

<400> SEQUENCE: 85
gaggtgcagc tgttggagtc tggggaggc ttggtacagc ctgggggtc cctgcgtctc      60 tcctgtgcag cctccggatt caccttctcat caggtccta tggggtgggt ccgccaggct    120
ccagggaagg gtctagagtg ggtctcatgg attcaggcta cgggtggtgc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagggatg    300
catcctcaga gtggtactct ttttgactac tggggtcagg gaaccctggt caccgtctcg    360
agc                                                                  363

<210> SEQ ID NO 86
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 86
gaggtgcagc tgttggagtc tggggaggc ttggtacagc ctgggggtc cctgcgtctc      60
```

```
tcctgtgcag cctccggatt cacctttgat gttgcggata tggattgggt ccgccaggct    120
ccagggaagg gtctagagtg ggtctcaggg atttcgtcgt cgggtggtta tacatactac    180
gcagactccg tgaagggccg gttcaccatc tcccgcgaca attccaagaa cacgctgtat    240
ctgcaaatga acagcctgcg tgccgaggat accgcggtat attactgtgc gaaaaatttg    300
ggtcagggtt ttgactactg gggtcaggga accctggtca ccgtctcgag c            351
```

<210> SEQ ID NO 87
<211> LENGTH: 357
<212> TYPE: DNA
<213> ORGANISM: Artificial Sequence
<220> FEATURE:
<223> OTHER INFORMATION: Derived from a Human germline sequence

<400> SEQUENCE: 87

```
gaggtgcagc tgttggagtc tgggggaggc ttggtacagc ctggggggtc cctgcgtctc     60
tcctgtgcag cctccggatt cacctttgat acgagtagta tgttgtgggt ccgccaggct    120
ccagggaagg gtctagagtg ggtctcagtt attcatcaga gtggtacgcc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatttccg    300
tttactcatg gtaagtttga ctactggggt caggaaccc tggtcaccgt ctcgagc       357
```

<210> SEQ ID NO 88
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 88

```
gaggtgcagc tgttggagtc tgggggaggc ttggtacagc ctggggggtc cctgcgtctc     60
tcctgtgcag cctccggatt cacctttaat aattatacga tggggtgggt ccgccaggct    120
ccagggaagg gtctagagtg ggtctcattg attcatacga gtggtacggt gacatactac    180
gcagactccg tgaagggccg gttcaccatc tcccgcgaca attccaagaa cacgctgtat    240
ctgcaaatga acagcctgcg tgccgaggac accgcggtat attactgtgc gaaatggagt    300
tcgagggcgt ttgactactg gggtcaggga accctggtca ccgtctcgag c            351
```

<210> SEQ ID NO 89
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 89

```
gaggtgcagc tgttggagtc tgggggaggc ttggtacagc ctggggggtc cctgcgtctc     60
tcctgtgcag cctccggatt cacctttggg aattatagga tgacttgggt ccgccaggct    120
ccagggaagg gtctagagtg ggtctcaact atttctcctt tgggtacgta tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagggcgt    300
tggtcgattt ttgactactg gggtcaggga accctggtca ccgtctcgag c            351
```

<210> SEQ ID NO 90
<211> LENGTH: 351
<212> TYPE: DNA

<213> ORGANISM: Artificial Sequence
<220> FEATURE:
<223> OTHER INFORMATION: Derived from a Human germline sequence

<400> SEQUENCE: 90

```
gaggtgcagc tgttggagtc tgggggaggc ttggtacagc ctggggggtc cctgcgtctc      60
tcctgtgcag cctccggatt cacctttggt agttatccta tgggttgggt ccgccaggct     120
ccagggaagg gtctggagtg gtctcatgg attcgtggga ggggtcttgc tacatactac      180
gcagactccg tgaagggccg gttcaccatc tcccgcgaca attccaagaa cacgctgtat     240
ctgcaaatga acagcctgcg tgccgaggac accgcggtat attactgtgc gaaatatttt     300
catggtaagt ttgactactg ggtcaggga accctggtca ccgtctcgag c               351
```

<210> SEQ ID NO 91
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 91

```
gaggtgcagc tgttggagtc tgggggaggc ttggtacagc ctggggggtc cctgcgtctc      60
tcctgtgcag cctccggatt cacctttagt gcttatgtga tgggttgggt acgccaggct     120
ccagggaagg gtctagagtg gtctcatcg attcggatgc cgggttatct gacatactac      180
gcagactccg tgaagggccg gttcaccatc tcccgcgaca attccaagaa cacgctgtat     240
ctgcaaatga acagcctgcg tgccgaggac accgcggtat attactgtgc gaaacgtact     300
cctttttttg actactgggg tcagggaacc ctggtcaccg tctcgagc                  348
```

<210> SEQ ID NO 92
<211> LENGTH: 369
<212> TYPE: DNA
<213> ORGANISM: Artificial Sequence
<220> FEATURE:
<223> OTHER INFORMATION: Derived from a Human germline sequence

<400> SEQUENCE: 92

```
gaggtgcagc tgttggagtc tgggggaggc ttggtacagc ctggggggtc cctgcgtctc      60
tcctgtgcag cctccggatt cacctttgag cattattcga tgggttgggt ccgccaggct     120
ccagggaagg gtctagagtg gtctcagag attgatccgg atggtattat gacatactac      180
gcagactccg tgaagggccg gttcaccatc tcccgcgaca attccaagaa cacgctgtat     240
ctgcaaatga acagcctgcg tgccgaggac accgcggtat attactgtgc gaaagcgccg     300
ggggttcttg agatgtggat tacgcatttt gactactggg gtcagggaac cctggtcacc    360
gtctcgagc                                                              369
```

<210> SEQ ID NO 93
<211> LENGTH: 360
<212> TYPE: DNA
<213> ORGANISM: Artificial Sequence
<220> FEATURE:
<223> OTHER INFORMATION: Derived from a Human germline sequence

<400> SEQUENCE: 93

```
gaggtgcagc tgttggagtc tgggggaggc ttggtacagc ctggggggtc cctgcgtctc      60
tcctgtgcag cctccggatt cacctttcgt cattatgtga tgggttgggt ccgccaggct     120
ccagggaagg gtctagagtg gtctcagct atttctgcgc atggtaatcg gacatactac      180
```

```
gcagactccg tgaagggccg gttcaccatc tcccgcgaca attccaagaa cacgctgtat      240
ctgcaaatga acagcctgcg tgccgaggac accgcggtat attactgtgc gaaatcttat      300
agccttgctc tgactccttt tgactactgg ggtcagggaa ccctggtcac cgtctcgagc      360
```

```
<210> SEQ ID NO 94
<211> LENGTH: 366
<212> TYPE: DNA
<213> ORGANISM: Artificial Sequence
<220> FEATURE:
<223> OTHER INFORMATION: Derived from a Human germline sequence

<400> SEQUENCE: 94
```

```
gaggtgcagc tgttggagtc tgggggaggc ttggtacagc ctggggggtc cctgcgtctc       60
tcctgtgcag cctccggatt caccttaact gtgtatgaga tgaagtgggt ccgccaggct      120
ccagggaagg gtctagagtg ggtctcagcg atttctgctg gggtaagta tacatactac       180 gcagactccg tgaagggccg gttcaccatc tcccgcgaca attccaagaa cacgctgtat      240
ctgcaaatga acagcctgcg tgccgaggac accgcggtat attactgtgc gaaagagatt     300
cggcatcttg ataatgcggt tgagtttgac tactggggtc agggaaccct ggtcaccgtc     360
tcgagc                                                                  366
```

```
<210> SEQ ID NO 95
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 95

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Gly Tyr
            20                  25                  30

Val Met Gly Trp Val Arg Gln Ala Pro Gly Lys Gly Leu Glu Trp Val
        35                  40                  45

Ser Ala Ile Asn Arg Phe Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Leu Arg His Phe Asp Tyr Trp Gly Gln Gly Thr Leu
            100                 105                 110

Val Thr Val Ser Ser
        115
```

```
<210> SEQ ID NO 96
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 96

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asn Tyr
            20                  25                  30
```

```
Ala Met Ala Trp Val Arg Gln Ala Pro Gly Lys Gly Leu Glu Trp Val
        35                  40                  45

Ser Ser Ile Asp Met Val Gly Ile Lys Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Phe Arg Ile Phe Asp Tyr Trp Gly Gln Gly Thr Leu Val
             100                 105                 110

Thr Val Ser Ser
         115
```

<210> SEQ ID NO 97
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 97

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Asp Tyr
             20                  25                  30

Asp Met Thr Trp Val Arg Gln Ala Pro Gly Lys Gly Leu Glu Trp Val
        35                  40                  45

Ser Met Ile Ser Ser Ser Gly Leu Trp Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Phe Arg Leu Phe Pro Arg Thr Phe Asp Tyr Trp Gly Gln
             100                 105                 110

Gly Thr Leu Val Thr Val Ser Ser
         115                 120
```

<210> SEQ ID NO 98
<211> LENGTH: 124
<212> TYPE: PRT
<213> ORGANISM: Artificial Sequence
<220> FEATURE:
<223> OTHER INFORMATION: Derived from a Human germline sequence

<400> SEQUENCE: 98

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Leu Tyr
             20                  25                  30

Arg Met Val Trp Val Arg Gln Ala Pro Gly Lys Gly Leu Glu Trp Val
        35                  40                  45

Ser Met Ile Ser Gln Phe Gly Asn Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

-continued

```
Ala Lys Val Arg Ser Trp Asp Gln Thr Gly Arg Arg Thr Phe Asp
            100                 105                 110
Tyr Trp Gly Gln Gly Thr Leu Val Thr Val Ser Ser
            115                 120

<210> SEQ ID NO 99
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 99

Glu Val Gln Leu Leu Glu Ser Gly Gly Gly Leu Val Gln Pro Gly Gly
  1               5                   10                  15
Ser Leu Arg Leu Ser Cys Ala Ala Ser Gly Phe Thr Phe Asn His Tyr
             20                  25                  30
Thr Met Gly Trp Val Arg Gln Ala Pro Gly Lys Gly Leu Glu Trp Val
         35                  40                  45
Ser Leu Ile His Pro Ser Gly Thr Val Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Trp Ser Ser Arg Ala Phe Asp Tyr Trp Gly Gln Gly Thr Leu
            100                 105                 110
Val Thr Val Ser Ser
            115

<210> SEQ ID NO 100
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 100

Glu Val Gln Leu Leu Glu Ser Gly Gly Gly Leu Val Gln Pro Gly Gly
  1               5                   10                  15
Ser Leu Arg Leu Ser Cys Ala Ala Ser Gly Phe Thr Phe Asp Asn Asn
             20                  25                  30
Ala Met Gly Trp Val Arg Gln Ala Pro Gly Lys Gly Leu Glu Trp Val
         35                  40                  45
Ser Thr Ile Ser Ala Asn Gly Asn Ala Thr Tyr Tyr Ala Asp Ser Val
     50                  55                  60
Lys Gly Arg Phe Thr Ile Ser Arg Asp Asn Ser Lys Asp Thr Leu Tyr
 65                  70                  75                  80
Leu Gln Met Asn Ser Leu Arg Ala Glu Asp Thr Ala Val Tyr Tyr Cys
                 85                  90                  95
Ala Lys Gly Phe Arg Arg Phe Asp Tyr Trp Gly Gln Gly Thr Leu Val
            100                 105                 110
Thr Val Ser Ser
            115

<210> SEQ ID NO 101
<211> LENGTH: 118
<212> TYPE: PRT
<213> ORGANISM: Artificial Sequence
<220> FEATURE:
```

<223> OTHER INFORMATION: Derived from a Human germline sequence

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Arg His Tyr
            20                  25                  30

Arg Met Gly Trp Val Arg Gln Ala Pro Gly Lys Gly Leu Glu Trp Val
        35                  40                  45

Ser Trp Ile Arg Pro Asp Gly Thr Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Met Gly Asp Arg Phe Asp Tyr Trp Gly Gln Gly Thr
            100                 105                 110

Leu Val Thr Val Ser Ser
            115

<210> SEQ ID NO 102
<211> LENGTH: 122
<212> TYPE: PRT
<213> ORGANISM: Artificial Sequence
<220> FEATURE:
<223> OTHER INFORMATION: Derived from a Human germline sequence

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Pro Met Thr Trp Val Arg Gln Ala Pro Gly Lys Gly Leu Glu Trp Val
        35                  40                  45

Ser Thr Ile Ser Tyr Gly Gly Leu Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Ala Ile Asn Gly Val Arg Pro Arg Arg Phe Asp Tyr Trp
            100                 105                 110

Gly Gln Gly Thr Leu Val Thr Val Ser Ser
            115                 120

<210> SEQ ID NO 103
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 103

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Ala Tyr
            20                  25                  30

Gln Met Ala Trp Val Arg Gln Ala Pro Gly Lys Gly Leu Glu Trp Val
        35                  40                  45

```
Ser Thr Ile His Gln Thr Gly Phe Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Arg Ser Met Arg Pro Tyr Lys Phe Asp Tyr Trp Gly Gln
            100                 105                 110

Gly Thr Leu Val Thr Val Ser Ser
            115                 120

<210> SEQ ID NO 104
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 104

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Asp Lys
                 20                  25                  30

Ala Met Gly Trp Val Arg Gln Ala Pro Gly Lys Gly Leu Glu Trp Val
             35                  40                  45

Ser Thr Ile Ser Ala Pro Gly Asn Arg Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Phe Arg Asn Phe Asp Tyr Trp Gln Gly Thr Leu Val
            100                 105                 110

Thr Val Ser Ser
        115

<210> SEQ ID NO 105
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 105

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asp Gly Met
                 20                  25                  30

Arg Met Gly Trp Val Arg Gln Ala Pro Gly Lys Gly Leu Glu Trp Val
             35                  40                  45

Ser Ala Ile Glu Val Asn Gly Gln His Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Met Ala His Pro Gln Ser Gly Val Ala Phe Asp Tyr Trp Gly
            100                 105                 110
```

```
Gln Gly Thr Leu Val Thr Val Ser Ser
        115                 120
```

<210> SEQ ID NO 106
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 106

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Thr Pro Asp
            20                  25                  30

Ala Met Ala Trp Val Arg Gln Ala Pro Gly Lys Gly Leu Glu Trp Val
        35                  40                  45

Ser Ser Ile Gly Val Asn Gly Ser Pro Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Ala His Pro Gln Ser Gly Val Ala Phe Asp Tyr Trp Gly
            100                 105                 110

Gln Gly Thr Leu Val Thr Val Ser Ser
        115                 120
```

<210> SEQ ID NO 107
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 107

```
Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Tyr Gln Ser
            20                  25                  30

Asp Met Ser Trp Val Arg Gln Ala Pro Gly Lys Gly Leu Glu Trp Val
        35                  40                  45

Ser Ser Ile Ser Ser Gln Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Ala His Pro Gln Ser Gly Val Ala Phe Asp Tyr Trp Gly
            100                 105                 110

Gln Gly Thr Leu Val Thr Val Ser Ser
        115                 120
```

<210> SEQ ID NO 108
<211> LENGTH: 121
<212> TYPE: PRT
<213> ORGANISM: Artificial Sequence
<220> FEATURE:
<223> OTHER INFORMATION: Derived from a Human germline sequence

```
<400> SEQUENCE: 108

Glu Val Gln Leu Leu Glu Ser Gly Gly Gly Leu Val Gln Pro Gly Gly
 1               5                  10                  15

Ser Leu Arg Leu Ser Cys Thr Ala Ser Gly Phe Thr Phe Ala Ala Arg
            20                  25                  30

Asp Met Ser Trp Val Arg Gln Ala Pro Gly Lys Gly Leu Glu Trp Val
        35                  40                  45

Ser Ser Ile Ser Ala Gln Gly Ala His Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
        115                 120

<210> SEQ ID NO 109
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 109

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Asn Gly
            20                  25                  30

Asp Met Val Trp Val Arg Gln Ala Pro Gly Lys Gly Leu Glu Trp Val
        35                  40                  45

Ser Gly Ile Ala His Asn Gly Arg Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Gly Gln Gly Phe Asp Tyr Trp Gly Gln Gly Thr Leu
            100                 105                 110

Val Thr Val Ser Ser
        115

<210> SEQ ID NO 110
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 110

Glu Val Gln Leu Leu Glu Ser Gly Gly Gly Leu Val Gln Pro Gly Gly
 1               5                  10                  15

Ser Leu Arg Leu Thr Cys Ala Ala Ser Gly Phe Thr Leu Asn Gly Thr
            20                  25                  30

Ser Met Gly Trp Val Arg Gln Ala Pro Gly Lys Asp Leu Glu Trp Val
        35                  40                  45

Ser Ser Ile Met Pro Val Gly Ser His Thr Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Met Ala His Pro Gln Ser Gly Val Ala Phe Asp Tyr Trp Gly
                    100                 105                 110

Gln Gly Thr Leu Val Thr Val Ser Ser
                    115                 120

<210> SEQ ID NO 111
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 111

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asp His Ala
                 20                  25                  30

Pro Met Lys Trp Ala Arg Gln Ala Pro Gly Lys Gly Leu Glu Trp Val
             35                  40                  45

Ser Tyr Ile Gly Ser Ala Gly Asn Met Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Asp Glu Gly Pro Phe Asp Tyr Trp Gly Gln Gly Thr Leu Val
                    100                 105                 110

Thr Val Ser Ser
                    115

<210> SEQ ID NO 112
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 112

Glu Val Gln Leu Leu Glu Ser Gly Gly Gly Leu Val Gln Pro Gly Gly
  1               5                  10                  15

Ser Leu Arg Leu Ser Cys Thr Ala Ser Gly Phe Thr Phe Asp Gly Met
                 20                  25                  30

Asp Met Ser Trp Val Arg Gln Ala Pro Gly Lys Gly Leu Glu Trp Val
             35                  40                  45

Ser Ser Ile Ser Thr Thr Gly Gly Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Pro Arg His Pro Gln Gly Gly Val Thr Phe Asp Tyr Trp Gly
                    100                 105                 110

Gln Gly Thr Leu Val Thr Val Ser Ser
```

-continued

<210> SEQ ID NO 113
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 113

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Ala Glu
            20                  25                  30

Thr Met Ala Trp Val Arg Gln Ala Pro Gly Lys Gly Leu Glu Trp Val
        35                  40                  45

Ser Thr Ile His Ser Glu Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
        115                 120

<210> SEQ ID NO 114
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 114

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
        115                 120

<210> SEQ ID NO 115
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 115

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Ser Ala
            20                  25                  30

Asp Met Val Trp Val Arg Gln Ala Pro Gly Lys Gly Leu Glu Trp Val
        35                  40                  45

Ser Arg Ile Ser Pro Glu Gly Asn His Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Arg Pro Pro Ser Asp Tyr Val Ser Phe Asp Tyr Trp Gly Gln
            100                 105                 110

Gly Thr Leu Val Thr Val Ser Ser
            115                 120

<210> SEQ ID NO 116
<211> LENGTH: 119
<212> TYPE: PRT
<213> ORGANISM: Artificial Sequence
<220> FEATURE:
<223> OTHER INFORMATION: Derived from a Human germline sequence

<400> SEQUENCE: 116

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asn Ala
            20                  25                  30

Thr Met Ser Trp Val Arg Gln Ala Pro Gly Lys Gly Leu Glu Trp Val
        35                  40                  45

Ser Asp Ile Asp Gln Val Gly His Ala Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Ser Trp His Pro Asp Leu Phe Asp Tyr Trp Gly Gln Gly
            100                 105                 110

Thr Leu Val Thr Val Ser Ser
            115

<210> SEQ ID NO 117
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 117

Glu Val Arg Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asp Tyr
            20                  25                  30

Gly Met Asn Trp Val Arg Gln Ala Pro Gly Lys Gly Leu Glu Trp Val
        35                  40                  45

Ser Arg Ile Ser Arg Asn Gly Thr Val Thr Tyr Tyr Ala Asp Ser Val
        50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Ala Ala Pro Val Arg Gln Lys Gly Met Asp Phe Asp Tyr
            100                 105                 110

Trp Gly Gln Gly Thr Leu Val Thr Val Ser Ser
        115                 120
```

```
<210> SEQ ID NO 118
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 118

Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Glu Trp Tyr
             20                  25                  30

Asn Met Ser Trp Val Arg Gln Ala Pro Gly Lys Asp Leu Glu Trp Val
             35                  40                  45

Ser Ser Ile Ser His Asp Gly Trp Asn Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Met Ile Gly Phe Asp Tyr Trp Gly Gln Gly Thr Leu Val
            100                 105                 110

Thr Val Ser Ser
        115
```

```
<210> SEQ ID NO 119
<211> LENGTH: 119
<212> TYPE: PRT
<213> ORGANISM: Artificial Sequence
<220> FEATURE:
<223> OTHER INFORMATION: Derived from a Human germline sequence

<400> SEQUENCE: 119

Val Gln Leu Leu Glu Ser Gly Gly Gly Leu Val Gln Pro Gly Gly Ser
 1                5                  10                  15

Leu Arg Leu Ser Cys Ala Ala Ser Gly Phe Thr Phe Asp Ile Tyr Thr
             20                  25                  30

Met His Trp Val Arg Gln Ala Pro Gly Lys Gly Leu Glu Trp Val Ser
             35                  40                  45

Thr Ile Val Pro Gln Gly Thr Pro Thr Tyr Tyr Ala Asp Ser Val Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ser Lys Arg Arg Phe Leu Lys Arg Phe Asp Tyr Trp Gly Gln Gly
            100                 105                 110

Thr Leu Val Thr Val Ser Ser
        115
```

<210> SEQ ID NO 120
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
            20                  25                  30

Asp Met Gln Trp Val Arg Gln Ala Pro Gly Lys Gly Leu Glu Trp Val
        35                  40                  45

Ser Ser Ile Lys Ser Asn Gly Met Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Ser Met Trp Thr Phe Asp Tyr Trp Gly Gln Gly Thr Leu
            100                 105                 110

Val Thr Val Ser Asn
        115

<210> SEQ ID NO 121
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 121

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Leu Tyr
            20                  25                  30

His Met Gly Trp Val Arg Gln Ala Pro Gly Lys Gly Leu Glu Trp Val
        35                  40                  45

Ser Ala Ile Thr Gly Gly Tyr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Leu Arg Gly Val Leu Trp Arg Arg Arg Phe Asp Tyr
            100                 105                 110

Trp Gly Gln Gly Thr Leu Val Thr Val Ser Ser
        115                 120

<210> SEQ ID NO 122
<211> LENGTH: 122
<212> TYPE: PRT
<213> ORGANISM: Artificial Sequence
<220> FEATURE:
<223> OTHER INFORMATION: Derived from a Human germline sequence

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ala Tyr
            20                  25                  30

Ser Met Met Trp Val Arg Gln Ala Pro Gly Lys Gly Leu Glu Trp Val
        35                  40                  45

Ser Arg Ile Ser Arg Asn Gly Thr Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Arg Trp Asn Thr Ala Gln Val Pro Val Phe Asp Tyr Trp
            100                 105                 110

Gly Gln Gly Thr Leu Val Thr Val Ser Ser
            115                 120

<210> SEQ ID NO 123
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Pro Tyr
            20                  25                  30

Trp Met Ala Trp Val Arg Gln Ala Pro Gly Lys Gly Leu Glu Trp Val
        35                  40                  45

Ser Thr Ile Thr Pro Ser Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Pro Arg Val Gly Leu Trp Arg Ser Gly Phe Asp Tyr
            100                 105                 110

Trp Gly Gln Gly Thr Leu Val Thr Val Ser Ser
            115                 120

<210> SEQ ID NO 124
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gln Tyr
            20                  25                  30

Ala Met Gln Trp Val Arg Gln Ala Pro Gly Lys Gly Leu Glu Trp Val
        35                  40                  45

Ser Ser Ile Asn Ile Thr Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Lys Gly Phe Arg Ser Phe Asp Tyr Trp Gly Gln Gly Thr Leu Val
                100                 105                 110

Thr Val Ser Ser
        115

<210> SEQ ID NO 125
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 125

Val Gln Leu Leu Glu Ser Gly Gly Gly Leu Val Gln Pro Gly Gly Ser
 1               5                  10                  15

Leu Arg Leu Ser Cys Ala Ala Ser Gly Phe Thr Phe Ala Gly Tyr Thr
            20                  25                  30

Met Ser Trp Val Arg Gln Ala Pro Gly Lys Gly Leu Glu Trp Val Ser
        35                  40                  45

Thr Ile Ser Gly Phe Gly Trp Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Arg Leu Gly Met Arg Phe Asp Tyr Trp Gly Gln Gly Thr Leu Val
            100                 105                 110

Thr Val Ser Ser
        115

<210> SEQ ID NO 126
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 126

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Pro Tyr
                20                  25                  30

Ser Met Gly Trp Val Arg Gln Ala Pro Gly Lys Gly Leu Glu Trp Val
            35                  40                  45

Ser Phe Ile His Ser Asp Gly Arg His Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Thr Pro Tyr Arg Phe Asp Tyr Trp Gly Gln Gly Thr Leu
            100                 105                 110

Val Thr Val Ser Ser
        115

<210> SEQ ID NO 127

```
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 127

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Gln Tyr
            20                  25                  30

Ala Met Gln Trp Val Arg Gln Ala Pro Gly Lys Gly Leu Glu Trp Val
        35                  40                  45

Ser Ser Ile Asn Ile Thr Gly Ser Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Phe Arg Ser Phe Asp Tyr Trp Gly Gln Gly Thr Leu Val
            100                 105                 110

Thr Val Ser Ser
        115

<210> SEQ ID NO 128
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 128

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Arg Tyr
            20                  25                  30

Ala Met Ser Trp Val Arg Gln Ala Pro Gly Lys Gly Leu Glu Trp Val
        35                  40                  45

Ser Thr Ile Ser Pro Tyr Gly Pro Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Tyr Tyr Gly Gly Phe Asp Tyr Trp Gly Gln Gly Thr Leu
            100                 105                 110

Val Thr Val Ser Ser
        115

<210> SEQ ID NO 129
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 129

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ala Tyr
```

-continued

```
                    20                  25                  30
Ala Met Gly Trp Val Arg Gln Ala Pro Gly Lys Gly Leu Glu Trp Val
        35                  40                  45

Ser Lys Ile Asp Ser Pro Gly Trp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Ala Arg Met Arg Ser Arg His Phe Asp Tyr Trp Gly Gln
            100                 105                 110

Gly Thr Leu Val Thr Val Ser Ser
            115                 120

<210> SEQ ID NO 130
<211> LENGTH: 122
<212> TYPE: PRT
<213> ORGANISM: Artificial Sequence
<220> FEATURE:
<223> OTHER INFORMATION: Derived from a Human germline sequence

<400> SEQUENCE: 130

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Asp Tyr
                20                  25                  30

Gly Met Asn Trp Val Arg Gln Ala Pro Gly Lys Gly Leu Glu Trp Val
            35                  40                  45

Ser Arg Ile Ser Arg Asn Gly Thr Val Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Arg Trp Asn Thr Ala Gln Val Pro Val Phe Asp Tyr Trp
            100                 105                 110

Gly Gln Gly Thr Leu Val Thr Val Ser Ser
            115                 120

<210> SEQ ID NO 131
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 131

Glu Val Gln Leu Leu Glu Ser Gly Gly Gly Leu Val Gln Pro Gly Gly
 1               5                  10                  15

Ser Leu Arg Leu Ser Cys Ala Thr Ser Gly Phe Thr Phe Pro Ser Tyr
                20                  25                  30

Thr Met Gly Trp Val Arg Gln Ala Pro Gly Lys Gly Leu Glu Trp Val
            35                  40                  45

Ser Arg Ile Ser Arg Thr Gly Asn Tyr Thr Tyr Tyr Ala Asp Ser Val
                50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

Ala Lys Pro Met Tyr Asn Arg Gly Ser Ser Tyr Phe Asp Tyr Trp Gly
                100                 105                 110

Gln Gly Thr Leu Val Thr Val Ser Ser
        115                 120

<210> SEQ ID NO 132
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gln Tyr
            20                  25                  30

Gln Met Ser Trp Val Arg Gln Ala Pro Gly Lys Gly Leu Glu Trp Val
        35                  40                  45

Ser Ser Ile Ser Pro Thr Gly Ile Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Leu Ile Gly Met Pro Tyr Val Gly Asp Thr Phe Asp Tyr
                100                 105                 110

Trp Gly Gln Gly Thr Leu Val Thr Val Ser Ser
        115                 120

<210> SEQ ID NO 133
<211> LENGTH: 124
<212> TYPE: PRT
<213> ORGANISM: Artificial Sequence
<220> FEATURE:
<223> OTHER INFORMATION: Derived from a Human germline sequence

<400> SEQUENCE: 133

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Met Glu Tyr
            20                  25                  30

Glu Met Glu Trp Val Arg Gln Ala Pro Gly Lys Gly Leu Glu Trp Val
        35                  40                  45

Ser Gly Ile Thr Asn Ser Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Met Gln His Pro Gln Ala Thr Gly Gly Arg Val Gly Phe Asp
                100                 105                 110

Tyr Trp Gly Gln Gly Thr Leu Val Thr Val Ser Ser
        115                 120

<210> SEQ ID NO 134
<211> LENGTH: 117
<212> TYPE: PRT

<213> ORGANISM: Artificial Sequence
<220> FEATURE:
<223> OTHER INFORMATION: Derived from a Human germline sequence

<400> SEQUENCE: 134

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Pro Arg Tyr
             20                  25                  30

Thr Met Lys Trp Val Arg Gln Ala Pro Gly Lys Gly Leu Glu Trp Val
         35                  40                  45

Ser Ser Ile Asp Arg Thr Gly Arg Lys Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Glu Ser Leu Val Ser Phe Asp Tyr Trp Gly Gln Gly Thr Leu
            100                 105                 110

Val Thr Val Ser Ser
        115
```

<210> SEQ ID NO 135
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 135

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Gly Tyr
             20                  25                  30

Thr Met Pro Trp Val Arg Gln Ala Pro Gly Lys Gly Leu Glu Trp Val
         35                  40                  45

Ser Thr Ile Ser Arg Asp Gly Asn Tyr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Asp Ile Gly Met Gly Phe Asp Tyr Gly Gly Arg Gly Thr Leu
            100                 105                 110

Val Thr Val Ser Ser
        115
```

<210> SEQ ID NO 136
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 136

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Ile Tyr
             20                  25                  30
```

```
Ala Met His Trp Val Arg Gln Ala Pro Gly Lys Gly Leu Glu Trp Val
        35                  40                  45

Ser Thr Ile Ser Ser Gly Gly Lys Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Arg Thr Met Tyr Phe Arg Val Arg Glu Ala Phe Asp Tyr
             100                 105                 110

Trp Gly Gln Gly Thr Leu Val Thr Val Ser Ser
             115                 120
```

<210> SEQ ID NO 137
<211> LENGTH: 124
<212> TYPE: PRT
<213> ORGANISM: Artificial Sequence
<220> FEATURE:
<223> OTHER INFORMATION: Derived from a Human germline sequence

<400> SEQUENCE: 137

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Ala Tyr
             20                  25                  30

Arg Met Met Trp Val Arg Gln Ala Pro Gly Lys Gly Leu Glu Trp Val
        35                  40                  45

Ser Ser Ile Asp Pro Asp Gly Ala Val Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu His Phe Asp Leu Ala Met Pro Asn Pro Asn Ala Lys Phe Asp
             100                 105                 110

Tyr Trp Gly Gln Gly Thr Leu Val Thr Val Ser Ser
             115                 120
```

<210> SEQ ID NO 138
<211> LENGTH: 122
<212> TYPE: PRT
<213> ORGANISM: Artificial Sequence
<220> FEATURE:
<223> OTHER INFORMATION: Derived from a Human germline sequence

<400> SEQUENCE: 138

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
             20                  25                  30

Gln Met Ser Trp Val Arg Gln Ala Pro Gly Lys Gly Leu Glu Trp Val
        35                  40                  45

Ser Ser Ile Lys Ser Asn Gly Ser Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Lys Pro Ser Arg Gln Ser Phe Gln Tyr Pro Ser Phe Asp Tyr Trp
            100                 105                 110

Gly Gln Gly Thr Leu Val Thr Val Ser Ser
            115                 120

<210> SEQ ID NO 139
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 139

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Arg Tyr
            20                  25                  30

Lys Met Gly Trp Val Arg Gln Ala Pro Gly Lys Gly Leu Glu Trp Val
        35                  40                  45

Ser Ser Ile Ser Pro Thr Gly Ser Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Gly Tyr Val Met Val Glu His Phe Asp Tyr Trp Gly Gln
            100                 105                 110

Gly Thr Leu Val Thr Val Ser Ser
            115                 120

<210> SEQ ID NO 140
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 140

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Pro Met Lys Trp Val Arg Gln Ala Pro Gly Lys Gly Leu Glu Trp Val
        35                  40                  45

Ser Thr Ile Asn Ser Ser Gly Thr Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Leu Leu Pro Phe Asp Tyr Trp Gly Gln Gly Thr Leu Val
            100                 105                 110

Thr Val Ser Ser
        115

<210> SEQ ID NO 141
<211> LENGTH: 123
<212> TYPE: PRT
<213> ORGANISM: Artificial Sequence
<220> FEATURE:

<223> OTHER INFORMATION: Derived from a Human germline sequence

<400> SEQUENCE: 141

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Arg Tyr
             20                  25                  30

Arg Met Cys Trp Val Arg Gln Ala Pro Gly Lys Gly Leu Glu Trp Val
         35                  40                  45

Ser Cys Ile Arg Asp Pro Gly Phe Pro Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Cys Ser Pro Ser Ser Thr Gln Cys Thr Gly Leu Phe Asp Tyr
            100                 105                 110

Trp Gly Gln Gly Thr Leu Val Thr Val Ser Ser
            115                 120
```

<210> SEQ ID NO 142
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 142

```
Val Gln Leu Leu Glu Ser Gly Gly Gly Leu Val Gln Pro Gly Gly Ser
  1               5                  10                  15

Leu Arg Leu Ser Cys Ala Ala Ser Gly Phe Thr Phe Arg Phe Tyr Gly
             20                  25                  30

Met Ala Trp Val Arg Gln Ala Pro Gly Lys Gly Leu Glu Trp Val Ser
         35                  40                  45

Leu Ile Asp Pro Pro Gly Gly Ala Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Lys Met Glu Arg Arg His Leu Leu Ser Gly His Lys Gly Phe Asp Tyr
            100                 105                 110

Trp Gly Gln Gly Thr Leu Val Thr Val Ser Ser
            115                 120
```

<210> SEQ ID NO 143
<211> LENGTH: 122
<212> TYPE: PRT
<213> ORGANISM: Artificial Sequence
<220> FEATURE:
<223> OTHER INFORMATION: Derived from a Human germline sequence

<400> SEQUENCE: 143

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Glu Tyr
             20                  25                  30

Asp Met Met Trp Val Arg Gln Ala Pro Gly Lys Gly Leu Glu Trp Val
         35                  40                  45
```

```
Ser Ser Ile Ser His Arg Gly Glu Lys Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Lys Arg Tyr Arg Gly Ser Gln His Tyr Phe Asp Tyr Trp
            100                 105                 110

Gly Gln Gly Thr Leu Val Thr Val Ser Ser
            115                 120

<210> SEQ ID NO 144
<211> LENGTH: 115
<212> TYPE: PRT
<213> ORGANISM: Artificial Sequence
<220> FEATURE:
<223> OTHER INFORMATION: Derived from a Human germline sequence

<400> SEQUENCE: 144

Val Gln Leu Leu Glu Ser Gly Gly Gly Leu Val Gln Pro Gly Gly Ser
 1               5                  10                  15

Leu Arg Leu Ser Cys Ala Ala Ser Gly Phe Thr Phe Arg Ser Tyr Asp
                20                  25                  30

Met Gly Trp Ala Arg Gln Ala Pro Gly Lys Gly Leu Glu Trp Val Ser
            35                  40                  45

Thr Ile Gly Ser Asn Gly Ala Asn Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Lys Leu Met Gly Met Phe Asp Tyr Trp Gly Gln Gly Thr Leu Val Thr
            100                 105                 110

Val Ser Ser
    115

<210> SEQ ID NO 145
<211> LENGTH: 118
<212> TYPE: PRT
<213> ORGANISM: Artificial Sequence
<220> FEATURE:
<223> OTHER INFORMATION: Derived from a Human germline sequence

<400> SEQUENCE: 145

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Arg Tyr
                20                  25                  30

Ser Met Arg Trp Val Arg Gln Ala Pro Gly Lys Gly Leu Glu Trp Val
            35                  40                  45

Ser Thr Ile Gly Ser Thr Gly Lys Trp Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Arg Gly Leu Val Ser Phe Asp Tyr Trp Gly Gln Gly Thr
            100                 105                 110
```

Leu Val Thr Val Ser Ser
        115

<210> SEQ ID NO 146
<211> LENGTH: 124
<212> TYPE: PRT
<213> ORGANISM: Artificial Sequence
<220> FEATURE:
<223> OTHER INFORMATION: Derived from a Human germline sequence

<400> SEQUENCE: 146

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Arg Tyr
            20                  25                  30

Ser Met Ser Trp Val Arg Gln Ala Pro Gly Lys Gly Leu Glu Trp Val
        35                  40                  45

Ser Ser Ile Asp Arg Ser Gly Arg Met Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Arg Leu Ser Ser Thr Gly Ser Glu Gly His Asn Phe Asp
            100                 105                 110

Tyr Trp Gly Gln Gly Thr Leu Val Thr Val Ser Ser
        115                 120

<210> SEQ ID NO 147
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 147

Val Gln Leu Leu Glu Ser Gly Gly Gly Leu Val Gln Pro Gly Gly Ser
 1               5                  10                  15

Leu Arg Leu Ser Cys Ala Ala Ser Gly Phe Thr Phe Lys Trp Tyr Pro
            20                  25                  30

Met Lys Trp Val Arg Gln Ala Pro Gly Lys Gly Leu Glu Trp Val Ser
        35                  40                  45

Thr Ile Ala Tyr Asp Gly Val Gln Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Leu Gly Pro Thr Ser Arg Val Phe Ala Ala Thr Asp Phe Asp Tyr
            100                 105                 110

Trp Gly Gln Gly Thr Leu Val Thr Val Ser Ser
        115                 120

<210> SEQ ID NO 148
<211> LENGTH: 122
<212> TYPE: PRT
<213> ORGANISM: Artificial Sequence
<220> FEATURE:
<223> OTHER INFORMATION: Derived from a Human germline sequence -continued

<400> SEQUENCE: 148

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Asn Tyr
            20                  25                  30

Ala Met Lys Trp Gly Arg Gln Ala Pro Gly Lys Gly Leu Glu Trp Val
        35                  40                  45

Ser Thr Ile Asp Thr Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr His Pro Met Ala Pro Arg Pro Ala Phe Asp Tyr Trp
            100                 105                 110

Gly Gln Gly Thr Leu Val Thr Val Ser Ser
            115                 120

<210> SEQ ID NO 149
<211> LENGTH: 122
<212> TYPE: PRT
<213> ORGANISM: Artificial Sequence
<220> FEATURE:
<223> OTHER INFORMATION: Derived from a Human germline sequence

<400> SEQUENCE: 149

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Leu Thr
            20                  25                  30

Glu Met Glu Trp Val Arg Gln Ala Pro Gly Lys Gly Leu Glu Trp Val
        35                  40                  45

Ser Ser Ile Gly Pro Trp Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser His Pro Gln Ala Met Tyr His Thr Phe Asp Tyr Trp
            100                 105                 110

Gly Gln Gly Thr Leu Val Thr Val Ser Ser
            115                 120

<210> SEQ ID NO 150
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 150

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala His Gln
            20                  25                  30

Asp Met Thr Trp Val Arg Gln Ala Pro Gly Lys Gly Leu Glu Trp Val
        35                  40                  45

Ser Asp Ile Asp His Ser Gly Ser Tyr Thr Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Trp Trp His Pro Gln Gly Gly Thr Phe Asp Tyr Trp Gly Gln
                100                 105                 110

Gly Thr Leu Val Thr Val Ser Ser
            115                 120

<210> SEQ ID NO 151
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 151

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Ser Lys
                 20                  25                  30

Asp Met Ser Trp Val Arg Gln Ala Pro Gly Lys Gly Leu Glu Trp Val
             35                  40                  45

Ser Thr Ile Gly Ala Asn Gly Lys Ala Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Ala Gly His Pro Gln Ala Pro Ser Phe Lys Ser Phe Asp Tyr
                100                 105                 110

Trp Gly Gln Gly Thr Leu Val Thr Val Ser Ser
            115                 120

<210> SEQ ID NO 152
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 152

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Asn Ala
                 20                  25                  30

Glu Met Ser Trp Val Arg Gln Ala Pro Gly Lys Gly Leu Glu Trp Val
             35                  40                  45

Ser Thr Ile Asp Arg Asp Gly Ala Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Pro Pro Met Ser Pro Lys Lys Phe Asp Tyr Trp Gly
                100                 105                 110

Gln Gly Thr Leu Val Thr Val Ser Ser
```

<210> SEQ ID NO 153
<211> LENGTH: 119
<212> TYPE: PRT
<213> ORGANISM: Artificial Sequence
<220> FEATURE:
<223> OTHER INFORMATION: Derived from a Human germline sequence

<400> SEQUENCE: 153

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Arg Glu
            20                  25                  30

Gly Met Met Trp Val Arg Gln Ala Pro Gly Lys Gly Leu Glu Trp Val
        35                  40                  45

Ser Thr Ile Asp Arg Met Gly Arg Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Asp Ser His Pro Met Gly Phe Asp Tyr Arg Gly Gln Gly
            100                 105                 110

Thr Leu Val Thr Val Ser Ser
        115

<210> SEQ ID NO 154
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 154

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Asn Glu
            20                  25                  30

Lys Met Ser Trp Val Arg Gln Ala Pro Gly Lys Gly Leu Glu Trp Val
        35                  40                  45

Ser Ser Ile Gly Pro Thr Gly Ser Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Pro His Pro Gln Val Ser Ser Phe Asp Tyr Trp Gly Gln
            100                 105                 110

Gly Thr Leu Val Thr Val Ser Ser
        115                 120

<210> SEQ ID NO 155
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 155

```
Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Glu Ile Asp
             20                  25                  30
His Met Gly Trp Val Arg Gln Ala Pro Gly Lys Gly Leu Glu Trp Val
         35                  40                  45
Ser Glu Ile Ala Pro Ser Gly Asp Arg Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Val Ile Cys Gln Asn Gln Cys Leu Phe Asp Tyr Trp Gly Gln
            100                 105                 110
Gly Thr Leu Val Thr Val Ser Ser
            115                 120

<210> SEQ ID NO 156
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 156

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Arg Asp Ser
             20                  25                  30
Glu Met Ser Trp Val Arg Gln Ala Pro Gly Lys Gly Leu Glu Trp Val
         35                  40                  45
Ser Phe Ile Thr Ser Asp Gly Arg Asp Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Pro Ser Leu Pro His Val Thr Ala Phe Asp Tyr Trp Gly Gln
            100                 105                 110
Gly Thr Leu Val Thr Val Ser Ser
            115                 120

<210> SEQ ID NO 157
<211> LENGTH: 122
<212> TYPE: PRT
<213> ORGANISM: Artificial Sequence
<220> FEATURE:
<223> OTHER INFORMATION: Derived from a Human germline sequence

<400> SEQUENCE: 157

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Glu Asp Glu
             20                  25                  30
Thr Met Ser Trp Ala Arg Gln Ala Pro Gly Lys Gly Leu Glu Trp Val
         35                  40                  45
Ser Ser Ile Gly Asp Ala Gly Met Pro Thr Tyr Tyr Ala Asp Ser Val
     50                  55                  60
```

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Pro Ile Tyr Val His Thr Thr His Phe Asp Tyr Trp
        100                 105                 110

Gly Gln Gly Thr Leu Val Thr Val Ser Ser
        115                 120

<210> SEQ ID NO 158
<211> LENGTH: 119
<212> TYPE: PRT
<213> ORGANISM: Artificial Sequence
<220> FEATURE:
<223> OTHER INFORMATION: Derived from a Human germline sequence

<400> SEQUENCE: 158

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Pro His Gly
            20                  25                  30

Lys Met Gly Trp Val Arg Gln Ala Pro Gly Lys Gly Leu Glu Trp Val
        35                  40                  45

Ser Trp Ile Ala Gly Ser Gly Asp Met Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Leu Gly His Pro Gln Arg Gly Phe Asp Tyr Trp Gly Gln Gly
        100                 105                 110

Thr Leu Val Thr Val Ser Ser
        115

<210> SEQ ID NO 159
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 159

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Gly Thr Ser
            20                  25                  30

Asp Met Ser Trp Val Arg Gln Ala Pro Gly Lys Gly Leu Glu Trp Val
        35                  40                  45

Ser Thr Ile Asp Ser Gly Gly Ser Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Pro Arg His Pro Gln Gly Val Thr Phe Asp Tyr Trp Gly
        100                 105                 110

Gln Gly Thr Leu Val Thr Val Ser Ser
        115                 120

<210> SEQ ID NO 160
<211> LENGTH: 119
<212> TYPE: PRT
<213> ORGANISM: Artificial Sequence
<220> FEATURE:
<223> OTHER INFORMATION: Derived from a Human germline sequence

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu His Val
            20                  25                  30

Pro Met Ala Trp Val Arg Gln Ala Pro Gly Lys Gly Leu Glu Trp Val
        35                  40                  45

Ser Arg Ile Ser Glu Gln Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gln His Pro Met Ser Phe Phe Asp Tyr Trp Gly Gln Gly
            100                 105                 110

Thr Leu Val Thr Val Ser Ser
        115

<210> SEQ ID NO 161
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 161

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Gln Gly
            20                  25                  30

Met Met Ser Trp Val Arg Gln Ala Pro Gly Lys Gly Leu Glu Trp Val
        35                  40                  45

Ser Ser Ile Asn Pro Gly Gly Gln Phe Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Asp Leu Gly Pro Gly Phe Asp Tyr Trp Gly Gln Gly Thr Leu
            100                 105                 110

Val Thr Val Ser Ser
        115

<210> SEQ ID NO 162
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 162

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Glu Arg Trp
            20                  25                  30

Pro Met Ser Trp Val Arg Gln Ala Pro Gly Lys Gly Leu Glu Trp Val
        35                  40                  45

Ser Thr Ile Asp Arg Ser Gly Asn Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu His Pro Gln Ala Gly Ser Ala Phe Asp Tyr Trp Gly
            100                 105                 110

Gln Gly Thr Leu Val Thr Val Ser Ser
            115                 120
```

<210> SEQ ID NO 163
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 163

```
Glu Val Gln Leu Leu Glu Ser Gly Gly Gly Ser Val Gln Pro Gly Gly
1               5                   10                  15

Ser Leu Arg Leu Ser Cys Ala Ala Ser Gly Phe Thr Phe Gly Gly Ser
            20                  25                  30

Asp Met Gly Trp Val Arg Gln Ala Pro Gly Lys Gly Leu Glu Trp Val
        35                  40                  45

Ser Tyr Ile Asp Asn Gln Gly Tyr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Lys Leu Leu Gly Pro Ser Thr Glu Phe Asp Tyr Trp Gly
            100                 105                 110

Gln Gly Thr Leu Val Thr Val Ser Ser
            115                 120
```

<210> SEQ ID NO 164
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 164

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Val Met Ser Trp Val Arg Gln Ala Pro Gly Lys Gly Leu Glu Trp Val
        35                  40                  45

Ser Ser Ile Thr Arg Ser Gly Met Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Tyr Ala His Pro Gln Ser Ala Val Glu Phe Asp Tyr Trp Gly
            100                 105                 110

Gln Gly Thr Leu Val Thr Val Ser Ser
            115                 120
```

<210> SEQ ID NO 165
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 165

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Asn Glu
             20                  25                  30

Pro Met Ser Trp Val Arg Gln Ala Pro Val Lys Gly Leu Glu Trp Val
         35                  40                  45

Ser Thr Ile Ser Pro Asp Gly Ser Gly Thr Tyr Tyr Ala Asp Ser Val
 50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Gly His Pro Gln Gly Ala Arg Phe Asp Tyr Trp Gly Gln
            100                 105                 110

Gly Thr Leu Val Thr Val Ser Ser
            115                 120
```

<210> SEQ ID NO 166
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 166

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Leu Asn Ser
             20                  25                  30

Glu Met Ser Trp Val Arg Gln Ala Pro Gly Lys Gly Leu Glu Trp Val
         35                  40                  45

Ser Thr Ile Gly Tyr Ala Gly Thr Pro Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
            115                 120
```

<210> SEQ ID NO 167

```
<211> LENGTH: 118
<212> TYPE: PRT
<213> ORGANISM: Artificial Sequence
<220> FEATURE:
<223> OTHER INFORMATION: Derived from a Human germline sequence

<400> SEQUENCE: 167

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Pro Met
            20                  25                  30

Ser Trp Val Arg Gln Ala Pro Gly Lys Gly Leu Glu Trp Val Ser Thr
        35                  40                  45

Ile Thr Asn Asp Gly Thr Ser Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Glu
                85                  90                  95

Pro Pro His Ser Gly Arg Pro Met Phe Asp Tyr Trp Gly Gln Gly Thr
            100                 105                 110

Leu Val Thr Val Ser Ser
        115

<210> SEQ ID NO 168
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 168

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gln Arg Thr
            20                  25                  30

Ala Met Ser Trp Val Arg Gln Ala Pro Gly Lys Gly Leu Glu Trp Val
        35                  40                  45

Ser Ser Ile Glu Ala Ser Gly Arg Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Ser His Pro Gln Asn Gly Arg Phe Asp Tyr Trp Gly Gln
            100                 105                 110

Gly Thr Leu Val Thr Val Ser Ser
        115                 120

<210> SEQ ID NO 169
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 169

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ala Ser
```

```
                    20                  25                  30
Glu Met Ala Trp Val Arg Gln Ala Pro Gly Lys Gly Leu Glu Trp Val
            35                  40                  45

Ser Ser Ile Thr Val Tyr Gly Asp Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
            115                 120

<210> SEQ ID NO 170
<211> LENGTH: 119
<212> TYPE: PRT
<213> ORGANISM: Artificial Sequence
<220> FEATURE:
<223> OTHER INFORMATION: Derived from a Human germline sequence

<400> SEQUENCE: 170

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Asp Ser
            20                  25                  30

His Met Ala Trp Val Arg Gln Ala Pro Gly Lys Gly Leu Glu Trp Val
            35                  40                  45

Ser Arg Ile Ser Arg Glu Gly Lys Ala Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Ala Pro Asn Asp Gln Ser Ala Ala Phe Asp Tyr Trp Gly Gln Gly
            100                 105                 110

Thr Leu Val Thr Val Ser Ser
            115

<210> SEQ ID NO 171
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 171

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Met Ser
            20                  25                  30

Glu Met Ser Trp Val Arg Gln Ala Pro Gly Lys Gly Leu Glu Trp Val
            35                  40                  45

Ser Ala Ile Thr Ser Asp Gly Ser Ser Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                    85                  90                  95
Ala Lys Pro Ser Leu Pro His Val Thr Ala Phe Asp Tyr Trp Gly Gln
            100                 105                 110

Gly Thr Leu Val Thr Val Ser Ser
        115                 120

<210> SEQ ID NO 172
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 172

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Arg Ser
            20                  25                  30

Thr Met His Trp Val Arg Gln Ala Pro Gly Lys Gly Leu Glu Trp Val
        35                  40                  45

Ser Glu Ile Asp Ala Leu Gly Thr Asp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ser Ser Asp His Pro Gln Asn Ser Phe Asp Tyr Trp Gly Gln
            100                 105                 110

Gly Thr Leu Val Thr Val Ser Ser
        115                 120

<210> SEQ ID NO 173
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 173

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Pro Arg
            20                  25                  30

Glu Met Tyr Trp Ala Arg Gln Ala Pro Gly Lys Gly Leu Glu Trp Val
        35                  40                  45

Ala Arg Ile Gly Trp Asp Gly His Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gln Leu Gly Gln Phe Asp Tyr Trp Gly Gln Gly Thr Leu Val
            100                 105                 110

Thr Val Ser Ser
        115

<210> SEQ ID NO 174
<211> LENGTH: 124
<212> TYPE: PRT
```

```
<213> ORGANISM: Artificial Sequence
<220> FEATURE:
<223> OTHER INFORMATION: Derived from a Human germline sequence

<400> SEQUENCE: 174

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ala Tyr
            20                  25                  30

Ser Met Met Trp Val Arg Gln Ala Pro Gly Lys Gly Leu Glu Trp Val
        35                  40                  45

Ser Thr Ile Gly Arg Trp Gly Glu Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Arg Tyr Ile Gly Pro Tyr Met Leu Ser Gly Arg Phe Asp
            100                 105                 110

Tyr Trp Gly Gln Gly Thr Leu Val Thr Val Ser Ser
        115                 120

<210> SEQ ID NO 175
<211> LENGTH: 124
<212> TYPE: PRT
<213> ORGANISM: Artificial Sequence
<220> FEATURE:
<223> OTHER INFORMATION: Derived from a Human germline sequence

<400> SEQUENCE: 175

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Met Arg Tyr
            20                  25                  30

Pro Met Val Trp Val Arg Gln Ala Pro Gly Arg Gly Leu Glu Trp Val
        35                  40                  45

Ser Ser Ile Ser Pro Ala Gly Tyr Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly His Glu Ile Ser Arg Phe Ser Arg Trp Ser Ser Phe Asp
            100                 105                 110

Tyr Trp Gly Gln Gly Thr Leu Val Thr Val Ser Ser
        115                 120

<210> SEQ ID NO 176
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 176

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Lys Tyr
            20                  25                  30
```

Arg Met Ser Trp Val Arg Gln Ala Pro Gly Lys Gly Leu Glu Trp Val
                35                  40                  45

Ser Ser Ile Ala Arg Asn Gly Arg Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Thr Ser Gly Phe Asp Tyr Trp Gly Gln Gly Thr Leu Val
            100                 105                 110

Thr Val Ser Ser
        115

<210> SEQ ID NO 177
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 177

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Lys Lys
            20                  25                  30

Glu Met Gly Trp Val Arg Gln Ala Pro Gly Lys Gly Leu Glu Trp Val
        35                  40                  45

Ser Ser Ile Asp Val Ser Gly Asn Val Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Ala His Pro Gln Ser Gly Val Ala Phe Asp Tyr Trp Gly
            100                 105                 110

Gln Gly Thr Leu Val Thr Val Ser Ser
            115                 120

<210> SEQ ID NO 178
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 178

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Met Tyr
            20                  25                  30

Asp Met Ala Trp Val Arg Gln Ala Pro Gly Lys Gly Leu Lys Trp Val
        35                  40                  45

Ser Thr Ile Leu Ser Ser Gly Lys Gly Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Leu Ala His Pro Gln Lys Gly Ser Ile Phe Asp Tyr Arg Gly
            100                 105                 110

Gln Gly Thr Leu Val Thr Val Ser Ser
            115                 120
```

<210> SEQ ID NO 179
<211> LENGTH: 121
<212> TYPE: PRT
<213> ORGANISM: Artificial Sequence
<220> FEATURE:
<223> OTHER INFORMATION: Derived from a Human germline sequence

<400> SEQUENCE: 179

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe His Gln Gly
             20                  25                  30

Pro Met Gly Trp Val Arg Gln Ala Pro Gly Lys Gly Leu Glu Trp Val
         35                  40                  45

Ser Trp Ile Gln Ala Thr Gly Gly Ala Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Met His Pro Gln Ser Gly Thr Leu Phe Asp Tyr Trp Gly
            100                 105                 110

Gln Gly Thr Leu Val Thr Val Ser Ser
            115                 120
```

<210> SEQ ID NO 180
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 180

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asp Val Ala
             20                  25                  30

Asp Met Asp Trp Val Arg Gln Ala Pro Gly Lys Gly Leu Glu Trp Val
         35                  40                  45

Ser Gly Ile Ser Ser Ser Gly Gly Tyr Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Gly Gln Gly Phe Asp Tyr Trp Gly Gln Gly Thr Leu
            100                 105                 110

Val Thr Val Ser Ser
            115
```

<210> SEQ ID NO 181
<211> LENGTH: 119
<212> TYPE: PRT
<213> ORGANISM: Artificial Sequence
<220> FEATURE:

<223> OTHER INFORMATION: Derived from a Human germline sequence

<400> SEQUENCE: 181

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Phe Thr His Gly Lys Phe Asp Tyr Trp Gly Gln Gly
            100                 105                 110

Thr Leu Val Thr Val Ser Ser
        115
```

<210> SEQ ID NO 182
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 182

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Asn Tyr
            20                  25                  30

Thr Met Gly Trp Val Arg Gln Ala Pro Gly Lys Gly Leu Glu Trp Val
        35                  40                  45

Ser Leu Ile His Thr Ser Gly Thr Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ser Arg Ala Phe Asp Tyr Trp Gly Gln Gly Thr Leu
            100                 105                 110

Val Thr Val Ser Ser
        115
```

<210> SEQ ID NO 183
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 183

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asn Tyr
            20                  25                  30

Arg Met Thr Trp Val Arg Gln Ala Pro Gly Lys Gly Leu Glu Trp Val
        35                  40                  45
```

Ser Thr Ile Ser Pro Leu Gly Thr Tyr Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Gly Arg Trp Ser Ile Phe Asp Tyr Trp Gly Gln Gly Thr Leu
            100                 105                 110

Val Thr Val Ser Ser
        115

<210> SEQ ID NO 184
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 184

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Ser Tyr
                20                  25                  30

Pro Met Gly Trp Val Arg Gln Ala Pro Gly Lys Gly Leu Glu Trp Val
            35                  40                  45

Ser Trp Ile Arg Gly Arg Gly Leu Ala Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Tyr Phe His Gly Lys Phe Asp Tyr Trp Gly Gln Gly Thr Leu
            100                 105                 110

Val Thr Val Ser Ser
        115

<210> SEQ ID NO 185
<211> LENGTH: 116
<212> TYPE: PRT
<213> ORGANISM: Artificial Sequence
<220> FEATURE:
<223> OTHER INFORMATION: Derived from a Human germline sequence

<400> SEQUENCE: 185

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
                20                  25                  30

Val Met Gly Trp Val Arg Gln Ala Pro Gly Lys Gly Leu Glu Trp Val
            35                  40                  45

Ser Ser Ile Arg Met Pro Gly Tyr Leu Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Arg Thr Pro Phe Phe Asp Tyr Trp Gly Gln Gly Thr Leu Val
            100                 105                 110

```
Thr Val Ser Ser
        115

<210> SEQ ID NO 186
<211> LENGTH: 123
<212> TYPE: PRT
<213> ORGANISM: Artificial Sequence
<220> FEATURE:
<223> OTHER INFORMATION: Derived from a Human germline sequence

<400> SEQUENCE: 186

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu His Tyr
            20                  25                  30

Ser Met Gly Trp Val Arg Gln Ala Pro Gly Lys Gly Leu Glu Trp Val
        35                  40                  45

Ser Glu Ile Asp Pro Asp Gly Ile Met Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Gly Val Leu Glu Met Trp Ile Thr His Phe Asp Tyr
            100                 105                 110

Trp Gly Gln Gly Thr Leu Val Thr Val Ser Ser
        115                 120

<210> SEQ ID NO 187
<211> LENGTH: 120
<212> TYPE: PRT
<213> ORGANISM: Artificial Sequence
<220> FEATURE:
<223> OTHER INFORMATION: Derived from a Human germline sequence

<400> SEQUENCE: 187

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg His Tyr
            20                  25                  30

Val Met Gly Trp Val Arg Gln Ala Pro Gly Lys Gly Leu Glu Trp Val
        35                  40                  45

Ser Ala Ile Ser Ala His Gly Asn Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Ser Leu Ala Leu Thr Pro Phe Asp Tyr Trp Gly Gln
            100                 105                 110

Gly Thr Leu Val Thr Val Ser Ser
        115                 120

<210> SEQ ID NO 188
<211> LENGTH: 122
<212> TYPE: PRT
<213> ORGANISM: Artificial Sequence
<220> FEATURE:
<223> OTHER INFORMATION: Derived from a Human germline sequence
```

<400> SEQUENCE: 188

| Glu | Val | Gln | Leu | Leu | Glu | Ser | Gly | Gly | Gly | Leu | Val | Gln | Pro | Gly | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Leu | Arg | Leu | Ser | Cys | Ala | Ala | Ser | Gly | Phe | Thr | Phe | Thr | Val | Tyr |
|     |     |     | 20  |     |     |     |     | 25  |     |     |     |     | 30  |     |     |

| Glu | Met | Lys | Trp | Val | Arg | Gln | Ala | Pro | Gly | Lys | Gly | Leu | Glu | Trp | Val |
|     |     | 35  |     |     |     |     | 40  |     |     |     |     | 45  |     |     |     |

| Ser | Ala | Ile | Ser | Ala | Gly | Gly | Lys | Tyr | Thr | Tyr | Tyr | Ala | Asp | Ser | Val |
| 50  |     |     |     |     | 55  |     |     |     |     | 60  |     |     |     |     |     |

| Lys | Gly | Arg | Phe | Thr | Ile | Ser | Arg | Asp | Asn | Ser | Lys | Asn | Thr | Leu | Tyr |
| 65  |     |     |     |     | 70  |     |     |     |     | 75  |     |     |     |     | 80  |

| Leu | Gln | Met | Asn | Ser | Leu | Arg | Ala | Glu | Asp | Thr | Ala | Val | Tyr | Tyr | Cys |
|     |     |     |     | 85  |     |     |     |     | 90  |     |     |     |     | 95  |     |

| Ala | Lys | Glu | Ile | Arg | His | Leu | Asp | Asn | Ala | Val | Glu | Phe | Asp | Tyr | Trp |
|     |     |     | 100 |     |     |     |     | 105 |     |     |     |     | 110 |     |     |

| Gly | Gln | Gly | Thr | Leu | Val | Thr | Val | Ser | Ser |
|     |     |     | 115 |     |     |     |     | 120 |     |

<210> SEQ ID NO 189
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 189

```
gaggtgcaac tgttggagtc tgggggaggc ttggtacagc ctggggggtc cctgcgtctc      60
tcctgtgcag cctccggatt cacctttaat cattatacga tgggttgggt ccgccaggct     120
ccagggaagg gtctagagtg gtctcattg attcatccga gtggtacggt gatatactac     180
gcagactccg tgaagggccg gttcaccatc tcccgcgaca attccaagaa cacgctgtat     240
ctgcaaatga acagcctgcg tgccgaggac accgcggtat attactgtgc gaaatggagt     300
tcgagggcat ttgactactg gggtcaggga accctggtca ccgtctctag c              351
```

<210> SEQ ID NO 190
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 190

```
gaggtgcagc tgttggagtc tgggggaggc ttggtacagc ctggggggtc cctgcgtctc      60
tcctgtgcag cctccggatt cacctttaat cattatacga tggggtgggt ccgccaggct     120
ccagggaagg gtcgagagtg gtctcattg attcatccga gtggtacggt gacatactac     180
gcagactccg tgaagggccg gttcaccatc tcccgcgaca attccaagaa cacgctgtat     240
ctgcaaatga acagcctgcg tgccgaggac accgcggtat attactgtgc gaaatggagt     300
tcgagggcgt ttgactactg gggtcaggga accctggtca ccgtctcgag c              351
```

<210> SEQ ID NO 191
<211> LENGTH: 351
<212> TYPE: DNA
<213> ORGANISM: Artificial Sequence
<220> FEATURE:
<223> OTHER INFORMATION: Derived from a Human germline sequence

<400> SEQUENCE: 191

```
gaggtgcaac tgttggagtc tggggaggc ttggtacagc ctgggggtc cctgcgtctc      60 tcctgtgcag cctccggatt cacctttaat cattatacga tgggttgggt ccgccaggct    120
ccagggaagg gtctagagtg gtctcattg attcatccga gtggtacggt gatatactac     180
gcagactccg tgaagggccg gttcaccatc tcccgcgaca attccaagaa cacgctgtat    240
ctgcaaatga acagcctgcg tgccgaggac accgcggtat attactgtgc gagatggagt   300
tcgagggcgt ttgactactg gggtcagggg accctggtca ccgtctcgag c            351
```

<210> SEQ ID NO 192
<211> LENGTH: 357
<212> TYPE: DNA
<213> ORGANISM: Artificial Sequence
<220> FEATURE:
<223> OTHER INFORMATION: Derived from a Human germline sequence

<400> SEQUENCE: 192

```
gaggtgcagc tgttggagtc tggggaggc ttggtacagc ctgggggtc cctgcgtctc      60 tcctgtgcag cctccggatt cacctttgat acgagtagta tgttgtgggt ccgccaggct   120
ccagggaagg gtctagagtg gtctcagtt attcatcaga gtggtacgcc tacatactac    180
gcagactccg tgaagggccg gttcaccatc tcccgcgaca attccaagaa cacgctgtat   240
ctgcaaatga acagcctgcg tgccgaggac accgcggtat attactgtgc gaaatttccg   300
tctactcatg gtaagtttga ctactgggt cagggaaccc tggtcaccgt ctcgagc      357
```

<210> SEQ ID NO 193
<211> LENGTH: 348
<212> TYPE: DNA
<213> ORGANISM: Artificial Sequence
<220> FEATURE:
<223> OTHER INFORMATION: Derived from a Human germline sequence

<400> SEQUENCE: 193

```
gaggtgcagc tgttggagtc tggggaggc ttggtacagc ctgggggtc cctgcgtctc      60 tcctgtgcag cctccggatt cacctttggt aattatgcga tggcgtgggt ccgccaggct   120
ccagggaagg gtctagagtg gtctcatcg attgatatgg ttggtattaa gacatactac    180
gcagactccg tgaagggccg gttcaccaat tcccgcgaca attccaagaa cacgctgtat   240
ctgcaaatga acagcctgcg tgccgaggac accgcggtat attactgtgc gagaggtttt   300
cgtatttttg actactgggg tcagggaacc ctggtcaccg tctcgagc                348
```

<210> SEQ ID NO 194
<211> LENGTH: 354
<212> TYPE: DNA
<213> ORGANISM: Artificial Sequence
<220> FEATURE:
<223> OTHER INFORMATION: Derived from a Human germline sequence

<400> SEQUENCE: 194

```
gaggtgcagc tgttggagtc tggggaggc ttggtacagc ctgggggtc cctgcgtctc      60 tcctgtacag cctccggatt cacctttagg cattatcgta tgggttgggt ccgccaggct   120
ccagggaagg gtctagagtg gtctcatgg attcgtccgg atggtacgtt tacatactac    180
gcagactccg tgaagggccg gttcaccatc tcccgcgaca attccaagaa cacgctgtat   240
ctgcaaatga acagcctgcg tgccgaggac accgcggtat attactgtgc gaaatcttat   300
atggctgata ggtttgacta ctggggtcag ggaaccctgg tcaccgtctc gagc         354
```

<210> SEQ ID NO 195

```
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 195

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn His Tyr
            20                  25                  30

Thr Met Gly Trp Val Arg Gln Ala Pro Gly Lys Gly Leu Glu Trp Val
        35                  40                  45

Ser Leu Ile His Pro Ser Gly Thr Val Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ser Arg Ala Phe Asp Tyr Trp Gly Gln Gly Thr Leu
            100                 105                 110

Val Thr Val Ser Ser
        115

<210> SEQ ID NO 196
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 196

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn His Tyr
            20                  25                  30

Thr Met Gly Trp Val Arg Gln Ala Pro Gly Lys Gly Arg Glu Trp Val
        35                  40                  45

Ser Leu Ile His Pro Ser Gly Thr Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ser Ser Arg Ala Phe Asp Tyr Trp Gly Gln Gly Thr Leu
            100                 105                 110

Val Thr Val Ser Ser
        115

<210> SEQ ID NO 197
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 197

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn His Tyr
```

-continued

```
                    20                  25                  30
Thr Met Gly Trp Val Arg Gln Ala Pro Gly Lys Gly Leu Glu Trp Val
                35                  40                  45

Ser Leu Ile His Pro Ser Gly Thr Val Ile Tyr Tyr Ala Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Trp Ser Ser Arg Ala Phe Asp Tyr Trp Gly Gln Gly Thr Leu
                100                 105                 110

Val Thr Val Ser Ser
            115

<210> SEQ ID NO 198
<211> LENGTH: 119
<212> TYPE: PRT
<213> ORGANISM: Artificial Sequence
<220> FEATURE:
<223> OTHER INFORMATION: Derived from a Human germline sequence

<400> SEQUENCE: 198

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Thr Ser
                20                  25                  30

Ser Met Leu Trp Val Arg Gln Ala Pro Gly Lys Gly Leu Glu Trp Val
                35                  40                  45

Ser Val Ile His Gln Ser Gly Thr Pro Thr Tyr Tyr Ala Asp Ser Val
            50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Phe Pro Ser Thr His Gly Lys Phe Asp Tyr Trp Gly Gln Gly
                100                 105                 110

Thr Leu Val Thr Val Ser Ser
            115

<210> SEQ ID NO 199
<211> LENGTH: 114
<212> TYPE: PRT
<213> ORGANISM: Artificial Sequence
<220> FEATURE:
<223> OTHER INFORMATION: Derived from a Human germline sequence

<400> SEQUENCE: 199

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asn Tyr
                20                  25                  30

Ala Met Ala Trp Val Arg Gln Ala Pro Gly Lys Gly Leu Glu Trp Val
                35                  40                  45

Ser Ser Ile Asp Met Val Gly Ile Lys Thr Tyr Tyr Ala Asp Ser Val
            50                  55                  60

Lys Gly Arg Phe Thr Asn Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
```

-continued

```
                        85                  90                  95
Arg Phe Arg Ile Phe Asp Tyr Trp Gly Gln Gly Thr Leu Val Thr Val
                100                 105                 110
Ser Ser

<210> SEQ ID NO 200
<211> LENGTH: 117
<212> TYPE: PRT
<213> ORGANISM: Artificial Sequence
<220> FEATURE:
<223> OTHER INFORMATION: Derived from a Human germline sequence

<400> SEQUENCE: 200

Glu Val Gln Leu Leu Glu Ser Gly Gly Leu Val Gln Pro Gly Gly
 1               5                  10                  15

Ser Leu Arg Leu Ser Cys Thr Ala Ser Gly Phe Thr Phe Arg His Tyr
                20                  25                  30

Arg Met Gly Trp Val Arg Gln Ala Pro Gly Lys Gly Leu Glu Trp Val
            35                  40                  45

Ser Trp Arg Pro Asp Gly Thr Phe Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Ser Tyr Met Ala Asp Arg Phe Asp Tyr Trp Gly Gln Gly Thr Leu
                100                 105                 110

Val Thr Val Ser Ser
            115
```

ANTI-SERUM ALBUMIN SINGLE VARIABLE DOMAINS

This application is a 371 of International Application No. PCT/EP2010/060112, filed 14 Jul. 2010, which claims the benefit of U.S. Provisional Application Nos. 61/226,028, filed 16 Jul. 2009 and 61/307,554 filed 24 Feb. 2010, which are incorporated by reference in their entireties.

The invention relates to improved anti-serum albumin immunoglobulin single variable domains, as well as ligands and drug conjugates comprising such domains, compositions, nucleic acids, vectors and hosts.

BACKGROUND OF THE INVENTION

WO04003019 and WO2008/096158 disclose anti-serum albumin (SA) binding moieties, such as anti-SA immunoglobulin single variable domains (dAbs), which have therapeutically-useful half-lives. These documents disclose monomer anti-SA dAbs as well as multi-specific ligands comprising such dAbs, eg, ligands comprising an anti-SA dAb and a dAb that specifically binds a target antigen, such as TNFR1. Binding moieties are disclosed that specifically bind serum albumins from more than one species, eg human/mouse cross-reactive anti-SA dAbs.

WO05118642 and WO2006/059106 disclose the concept of conjugating or associating an anti-SA binding moiety, such as an anti-SA immunoglobulin single variable domain, to a drug, in order to increase the half-life of the drug. Protein, peptide and NCE (chemical entity) drugs are disclosed and exemplified. WO2006/059106 discloses the use of this concept to increase the half-life of insulintropic agents, eg, incretin hormones such as glucagon-like peptide (GLP)-1.

Reference is also made to Holt et al, "Anti-Serum albumin domain antibodies for extending the half-lives of short lived drugs", Protein Engineering, Design & Selection, vol 21, no 5, pp 283-288, 2008.

It would be desirable to provide improved heavy chain variable domain dAbs that specifically bind serum albumin, preferably albumins from human and non-human species, which would provide utility in animal models of disease as well as for human therapy and/or diagnosis. It would also be desirable to provide for the choice between relatively modest- and high-affinity anti-SA binding moieties (dAbs). Such moieties could be linked to drugs, the anti-SA binding moiety being chosen according to the contemplated end-application. This would allow the drug to be better tailored to treating and/or preventing chronic or acute indications, depending upon the choice of anti-SA binding moiety. It would also be desirable to provide anti-SA dAbs that are monomeric or substantially so in solution. This would especially be advantageous when the anti-SA dAb is linked to a binding moiety, eg, a dAb, that specifically binds a cell-surface receptor, such as TNFR1, with the aim of antagonizing the receptor. The monomeric state of the anti-SA dAb is useful in reducing the chance of receptor cross-linking, since multimers are less likely to form which could bind and cross-link receptors (eg, TNFR1) on the cell surface, thus increasing the likelihood of receptor agonism and detrimental receptor signaling. It would also be desirable to provide anti-SA dAbs that have relatively high melting temperatures. This is useful for providing stable formulations, eg, storage-stable formulations and variable domains that have a good shelf-life.

SUMMARY OF THE INVENTION

Aspects of the present invention solve these problems.

In one aspect the invention, therefore, there is provided an anti-serum albumin (SA) immunoglobulin single variable domain comprising an amino acid sequence that is at least 80% identical to an amino acid sequence selected from SEQ ID NOs: 95 to 188 and 195 to 200.

An aspect of the invention provides an anti-serum albumin (SA) immunoglobulin single variable domain comprising an amino acid sequence having up to 4 amino acid changes compared to an amino acid sequence selected from SEQ ID NOs: 95 to 188 and 195 to 200.

An aspect of the invention provides an anti-serum albumin (SA) immunoglobulin single variable domain comprising an amino acid sequence that is encoded by a nucleotide sequence which is at least 80% identical to a sequence selected from SEQ ID NOs 1 to 94 and 189 to 197.

An aspect of the invention provides a multispecific ligand comprising an anti-SA variable domain of the invention and a binding moiety that specifically binds a target antigen other than SA.

An aspect of the invention provides an anti-SA single variable domain of the invention, wherein the variable domain is conjugated to a drug (optionally an NCE drug).

An aspect of the invention provides a fusion product, eg, a fusion protein or fusion with a peptide or NCE (new chemical entity) drug, comprising a polypeptide, protein, peptide or NCE drug fused or conjugated (for an NCE) to any anti-SA variable domain of the invention. For example, the variable domain comprises or consists of the amino acid sequence of any one of SEQ ID NOs: 95 to 101 and 195 to 200 (or an amino acid sequence that is at least 95, 96, 97, 98 or 99% identical to the amino acid sequence of any one of SEQ ID NOs: 95 to 101 and 195 to 200).

An aspect of the invention provides a composition comprising a variable domain, fusion protein or ligand of the invention and a pharmaceutically acceptable diluent, carrier, excipient or vehicle.

An aspect of the invention provides a nucleic acid comprising a nucleotide sequence encoding a variable domain, or a multispecific ligand or fusion protein of the invention.

An aspect of the invention provides a nucleic acid comprising a nucleotide sequence that is at least 80% identical to a sequence selected from SEQ ID NOs 1 to 94 and 189-194.

An aspect of the invention provides a vector comprising the nucleic acid of the invention.

An aspect of the invention provides an isolated host cell comprising the vector of the invention.

An aspect of the invention provides a method of treating or preventing a disease or disorder in a patient, comprising administering at least one dose of a variable domain, or a multispecific ligand or fusion protein of the invention to said patient.

Embodiments of any aspect of the invention provide anti-serum albumin single variable domains of good anti-serum albumin affinities. The choice of variable domain can allow for tailoring of half-life according to the desired therapeutic and/or prophylactic setting. For example, in one embodiment, the affinity of the variable domain for serum albumin is relatively high, such that the variable domain would be useful for inclusion in products that find utility in treating and/or preventing chronic or persistent diseases, conditions, toxicity or other chronic indications. In one embodiment, the affinity of the variable domain for serum albumin is relatively modest, such that the variable domain would be useful for inclusion in products that find utility in treating and/or preventing acute diseases, conditions, toxicity or other acute indications. In one embodiment, the affinity of the variable domain for serum albumin is intermediate, such that the variable domain would be useful for inclusion in products that find utility in treating and/or preventing acute or chronic diseases, conditions, toxicity or other acute or chronic indications.

It is conceivable that a molecule with an appropriately high affinity and specificity for serum albumin would stay in circulation long enough to have the desired therapeutic effect. (Tomlinson, *Nature Biotechnology* 22, 521-522 (2004)). Here, a high affinity anti-SA variable domain would stay in serum circulation matching that of the species' serum albumin (WO2008096158). Once in circulation, any fused therapeutic agent to the AlbudAb variable domain, be it NCE, peptide or protein, consequently would be able to act longer on its target and exhibit a longer lasting therapeutic effect. This would allow for targeting chronic or persistent diseases without the need of frequent dosing.

A variable domain with moderate affinity, (but specificity to SA) would only stay in serum circulation for a short time (eg, for a few hours or a few days) allowing for the specific targeting of therapeutic targets involved in acute diseases by the fused therapeutic agent.

This way it is possible to tailor the anti-SA-containing product to the therapeutic disease area by choosing an anti-SA variable domain with the appropriate albumin binding affinity and/or serum half-life.

DETAILED DESCRIPTION OF THE INVENTION

Within this specification the invention has been described, with reference to embodiments, in a way which enables a clear and concise specification to be written. It is intended and should be appreciated that embodiments may be variously combined or separated without parting from the invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods.

As used herein, the term "antagonist of Tumor Necrosis Factor Receptor 1 (TNFR1)" or "anti-TNFR1 antagonist" or the like refers to an agent (e.g., a molecule, a compound) which binds TNFR1 and can inhibit a (i.e., one or more) function of TNFR1. For example, an antagonist of TNFR1 can inhibit the binding of TNFα to TNFR1 and/or inhibit signal transduction mediated through TNFR1. Accordingly, TNFR1-mediated processes and cellular responses (e.g., TNFα-induced cell death in a standard L929 cytotoxicity assay) can be inhibited with an antagonist of TNFR1.

A "patient" is any animal, eg, a mammal, eg, a non-human primate (such as a baboon, rhesus monkey or Cynomolgus monkey), mouse, human, rabbit, rat, dog, cat or pig. In one embodiment, the patient is a human.

As used herein, "peptide" refers to about two to about 50 amino acids that are joined together via peptide bonds.

As used herein, "polypeptide" refers to at least about 50 amino acids that are joined together by peptide bonds. Polypeptides generally comprise tertiary structure and fold into functional domains.

As used herein an antibody refers to IgG, IgM, IgA, IgD or IgE or a fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

As used herein, "antibody format" refers to any suitable polypeptide structure in which one or more antibody variable domains can be incorporated so as to confer binding specificity for antigen on the structure. A variety of suitable antibody formats are known in the art, such as, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single antibody variable domain (e.g., a dAb, $V_H$, $V_{HH}$, $V_L$), and modified versions of any of the foregoing (e.g., modified by the covalent attachment of polyethylene glycol or other suitable polymer or a humanized $V_{HH}$).

The phrase "immunoglobulin single variable domain" refers to an antibody variable domain ($V_H$, $V_{HH}$, $V_L$) that specifically binds an antigen or epitope independently of different V regions or domains. An immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" as the term is used herein. A "single immunoglobulin variable domain" is the same as an "immunoglobulin single variable domain" as the term is used herein. A "single antibody variable domain" or an "antibody single variable domain" is the same as an "immunoglobulin single variable domain" as the term is used herein. An immunoglobulin single variable domain is in one embodiment a human antibody variable domain, but also includes single antibody variable domains from other species such as rodent (for example, as disclosed in WO 00/29004, the contents of which are incorporated herein by reference in their entirety), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. The $V_{HH}$ may be humanized.

A "domain" is a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

In the instant application, the term "prevention" and "preventing" involves administration of the protective composition prior to the induction of the disease or condition. "Treatment" and "treating" involves administration of the protective composition after disease or condition symptoms become manifest. "Suppression" or "suppressing" refers to administration of the composition after an inductive event, but prior to the clinical appearance of the disease or condition.

As used herein, the term "dose" refers to the quantity of ligand administered to a subject all at one time (unit dose), or in two or more administrations over a defined time interval. For example, dose can refer to the quantity of ligand (e.g., ligand comprising an immunoglobulin single variable domain that binds target antigen) administered to a subject over the course of one day (24 hours) (daily dose), two days, one week, two weeks, three weeks or one or more months (e.g., by a single administration, or by two or more administrations). The interval between doses can be any desired amount of time. The term "pharmaceutically effective" when referring to a dose means sufficient amount of the ligand, domain or pharmaceutically active agent to provide the desired effect. The amount that is "effective" will vary from subject to subject, depending on the age and general condition of the individual, the particular drug or pharmaceutically active agent and the like. Thus, it is not always possible to specify an exact "effective" amount applicable for all patients. However, an appropriate "effective" dose in any individual case may be determined by one of ordinary skill in the art using routine experimentation.

Methods for pharmacokinetic analysis and determination of ligand (eg, single variable domain, fusion protein or multispecific ligand) half-life will be familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC). Optionally, all pharmacokinetic parameters and values quoted herein are to be read as being values in a human. Optionally, all pharmacokinetic parameters and values quoted herein are to be read as being values in a mouse or rat or Cynomolgus monkey.

Half lives (t½ alpha and t½ beta) and AUC can be determined from a curve of serum concentration of ligand against time. The WinNonlin analysis package, eg version 5.1 (available from Pharsight Corp., Mountain View, Calif. 94040, USA) can be used, for example, to model the curve. When two-compartment modeling is used, in a first phase (the alpha phase) the ligand is undergoing mainly distribution in the patient, with some elimination. A second phase (beta phase) is the phase when the ligand has been distributed and the serum concentration is decreasing as the ligand is cleared from the patient. The t alpha half life is the half life of the first phase and the t beta half life is the half life of the second phase. Thus, in one embodiment, in the context of the present invention, the variable domain, fusion protein or ligand has a tα half-life in the range of (or of about) 15 minutes or more. In one embodiment, the lower end of the range is (or is about) 30 minutes, 45 minutes, 1 hour, 2 hours, 3 hours, 4 hours, 5 hours, 6 hours, 7 hours, 10 hours, 11 hours or 12 hours. In addition, or alternatively, the variable domain, fusion protein or ligand according to the invention will have a tα half life in the range of up to and including 12 hours (or about 12 hours). In one embodiment, the upper end of the range is (or is about) 11, 10, 9, 8, 7, 6 or 5 hours. An example of a suitable range is (or is about) 1 to 6 hours, 2 to 5 hours or 3 to 4 hours.

In one embodiment, the present invention provides the variable domain, fusion protein or ligand according to the invention has a tβ half-life in the range of (or of about) 2.5 hours or more. In one embodiment, the lower end of the range is (or is about) 3 hours, 4 hours, 5 hours, 6 hours, 7 hours, 10 hours, 11 hours, or 12 hours. In addition, or alternatively, the tβ half-life is (or is about) up to and including 21 or 25 days. In one embodiment, the upper end of the range is (or is about) 12 hours, 24 hours, 2 days, 3 days, 5 days, 10 days, 15 days, 19 days 20 days, 21 days or 22 days. For example, the variable domain, fusion protein or ligand according to the invention will have a tβ half life in the range 12 to 60 hours (or about 12 to 60 hours). In a further embodiment, it will be in the range 12 to 48 hours (or about 12 to 48 hours). In a further embodiment still, it will be in the range 12 to 26 hours (or about 12 to 26 hours).

As an alternative to using two-compartment modeling, the skilled person will be familiar with the use of non-compartmental modeling, which can be used to determine terminal half-lives (in this respect, the term "terminal half-life" as used herein means a terminal half-life determined using non-compartmental modeling). The WinNonlin analysis package, eg version 5.1 (available from Pharsight Corp., Mountain View, Calif. 94040, USA) can be used, for example, to model the curve in this way. In this instance, in one embodiment the single variable domain, fusion protein or ligand has a terminal half life of at least (or at least about) 8 hours, 10 hours, 12 hours, 15 hours, 28 hours, 20 hours, 1 day, 2 days, 3 days, 7 days, 14 days, 15 days, 16 days, 17 days, 18 days, 19 days, 20 days, 21 days, 22 days, 23 days, 24 days or 25 days. In one embodiment, the upper end of this range is (or is about) 24 hours, 48 hours, 60 hours or 72 hours or 120 hours. For example, the terminal half-life is (or is about) from 8 hours to 60 hours, or 8 hours to 48 hours or 12 to 120 hours, eg, in man.

In addition, or alternatively to the above criteria, the variable domain, fusion protein or ligand according to the invention has an AUC value (area under the curve) in the range of (or of about) 1 mg·min/ml or more. In one embodiment, the lower end of the range is (or is about) 5, 10, 15, 20, 30, 100, 200 or 300 mg·min/ml. In addition, or alternatively, the variable domain, fusion protein or ligand according to the invention has an AUC in the range of (or of about) up to 600 mg·min/ml. In one embodiment, the upper end of the range is (or is about) 500, 400, 300, 200, 150, 100, 75 or 50 mg·min/ml. Advantageously the variable domain, fusion protein or ligand will have an AUC in (or about in) the range selected from the group consisting of the following: 15 to 150 mg·min/ml, 15 to 100 mg·min/ml, 15 to 75 mg·min/ml, and 15 to 50 mg·min/ml.

"Surface Plasmon Resonance": Competition assays can be used to determine if a specific antigen or epitope, such as human serum albumin, competes with another antigen or epitope, such as cynomolgus serum albumin, for binding to a serum albumin binding ligand described herein, such as a specific dAb. Similarly competition assays can be used to determine if a first ligand such as dAb, competes with a second ligand such as a dAb for binding to a target antigen or epitope. The term "competes" as used herein refers to substance, such as a molecule, compound, preferably a protein, which is able to interfere to any extent with the specific binding interaction between two or more molecules. The phrase "does not competitively inhibit" means that substance, such as a molecule, compound, preferably a protein, does not interfere to any measurable or significant extent with the specific binding interaction between two or more molecules.

The specific binding interaction between two or more molecules preferably includes the specific binding interaction between a single variable domain and its cognate partner or target. The interfering or competing molecule can be another single variable domain or it can be a molecule that that is structurally and/or functionally similar to a cognate partner or target.

The term "binding moiety" refers to a domain that specifically binds an antigen or epitope independently of a different epitope or antigen binding domain. A binding moiety may be a domain antibody (dAb) or may be a domain which is a derivative of a non-immunoglobulin protein scaffold, eg, a scaffold selected from the group consisting of CTLA-4, lipocalin, SpA, an adnectin, affibody, an avimer, GroEl, transferrin, GroES and fibronectin, which binds to a ligand other than the natural ligand (in the case of the present invention, the moiety binds serum albumin). See WO2008/096158, which discloses examples of protein scaffolds and methods for selecting antigen or epitope-specific binding domains from repertoires (see Examples 17 to 25). These specific disclosures of WO2008/096158 are expressly incorporated herein by reference as though explicitly written herein and for use with the present invention, and it is contemplated that any part of such disclosure can be incorporated into one or more claims herein).

In one embodiment, a variable domain of the invention comprises one or more of the following kinetic characteristics:

(a) The variable domain comprises a binding site that specifically binds human SA with a dissociation constant (KD) from (or from about) 0.1 to (or to about) 10000 nM, optionally from (or from about) 1 to (or to about) 6000 nM, as determined by surface plasmon resonance;

(b) The variable domain comprises a binding site that specifically binds human SA with an off-rate constant ($K_d$) from (or from about) $1.5 \times 10^{-4}$ to (or to about) $0.1 \text{ sec}^{-1}$, optionally from (or from about) $3 \times 10^{-4}$ to (or to about) $0.1 \text{ sec}^{-1}$ as determined by surface plasmon resonance;

(c) The variable domain comprises a binding site that specifically binds human SA with an on-rate constant ($K_a$) from (or from about) $2 \times 10^6$ to (or to about) $1 \times 10^4 \text{M}^{-1} \text{sec}^{-1}$, optionally from (or from about) $1 \times 10^6$ to (or to about) $2 \times 10^4 \text{M}^{-1} \text{sec}^{-1}$ as determined by surface plasmon resonance;

(d) The variable domain comprises a binding site that specifically binds Cynomolgus monkey SA with a dissociation constant (KD) from (or from about) 0.1 to (or to about) 10000 nM, optionally from (or from about) 1 to (or to about) 6000 nM, as determined by surface plasmon resonance;

(e) The variable domain of any preceding claim, wherein the variable domain comprises a binding site that specifically binds Cynomolgus monkey SA with an off-rate constant ($K_d$) from (or from about) $1.5 \times 10^{-4}$ to (or to about) $0.1 \text{ sec}^{-1}$, optionally from (or from about) $3 \times 10^{-4}$ to (or to about) $0.1 \text{ sec}^{-1}$ as determined by surface plasmon resonance;

(f) The variable domain of any preceding claim, wherein the variable domain comprises a binding site that specifically binds Cynomolgus monkey SA with an on-rate constant ($K_a$) from (or from about) $2 \times 10^6$ to (or to about) $1 \times 10^4 \text{M}^{-1} \text{sec}^{-1}$, optionally from (or from about) $1 \times 10^6$ to (or to about) $5 \times 10^3 \text{ M}^{-1} \text{sec}^{-1}$ as determined by surface plasmon resonance;

(g) The variable domain comprises a binding site that specifically binds rat SA with a dissociation constant (KD) from (or from about) 1 to (or to about) 10000 nM, optionally from (or from about) 20 to (or to about) 6000 nM, as determined by surface plasmon resonance;

(h) The variable domain comprises a binding site that specifically binds rat SA with an off-rate constant ($K_d$) from (or from about) $2 \times 10^{-3}$ to (or to about) $0.15 \text{ sec}^{-1}$, optionally from (or from about) $9 \times 10^{-3}$ to (or to about) $0.14 \text{ sec}^{-1}$ as determined by surface plasmon resonance;

(i) The variable domain comprises a binding site that specifically binds rat SA with an on-rate constant ($K_a$) from (or from about) $2 \times 10^6$ to (or to about) $1 \times 10^4 \text{M}^{-1} \text{sec}^{-1}$, optionally from (or from about) $1 \times 10^6$ to (or to about) $3 \times 10^4 \text{M}^{-1} \text{sec}^{-1}$ as determined by surface plasmon resonance;

(j) The variable domain comprises a binding site that specifically binds mouse SA with a dissociation constant (KD) from (or from about) 1 to (or to about) 10000 nM as determined by surface plasmon resonance;

(k) The variable domain comprises a binding site that specifically binds mouse SA with an off-rate constant ($K_d$) from (or from about) $2 \times 10^{-3}$ to (or to about) $0.15 \text{ sec}^{-1}$ as determined by surface plasmon resonance; and/or (l) The variable domain comprises a binding site that specifically binds mouse SA with an on-rate constant ($K_a$) from (or from about) $2 \times 10^6$ to (or to about) $1 \times 10^4 \text{M}^{-1} \text{sec}^{-1}$, optionally from (or from about) $2 \times 10^6$ to (or to about) $1.5 \times 10^4 \text{ M}^{-1} \text{sec}^{-1}$ as determined by surface plasmon resonance.

Optionally, the variable domain has

I: a KD according to (a) and (d), a $K_d$ according to (b) and (e), and a $K_a$ according to (c) and (f); or II: a KD according to (a) and (g), a $K_d$ according to (b) and (h), and a $K_a$ according to (c) and (i); or III: a KD according to (a) and (j), a $K_d$ according to (b) and (k), and a $K_a$ according to (c) and (l); or IV: kinetics according to I and II; or V: kinetics according to I and III; or VI: kinetics according to I, II and III.

The invention also provides a ligand comprising a variable domain of any preceding aspect or embodiment of the invention. For example, the ligand can be a dual-specific ligand (see WO04003019 for examples of dual-specific ligands). In one aspect, the invention provides a multispecific ligand comprising an anti-SA variable domain of any preceding aspect or embodiment of the invention and a binding moiety that specifically binds a target antigen other than SA. The binding moiety can be any binding moiety that specifically binds a target, eg, the moiety is an antibody, antibody fragment, scFv, Fab, dAb or a binding moiety comprising a non-immunoglobulin protein scaffold. Such moieties are disclosed in detail in WO2008/096158 (see examples 17 to 25, which disclosure is incorporated herein by reference). Examples of non-immunoglobulin scaffolds are CTLA-4, lipocallin, staphylococcal protein A (spA), Affibody™, Avimers™, adnectins, GroEL and fibronectin.

In one embodiment, a linker is provided between the anti-target binding moiety and the anti-SA variable domain, the linker comprising the amino acid sequence AST, optionally ASTSGPS. Alternative linkers are described in WO2007085814 (incorporated herein by reference) and WO2008/096158 (see the passage at page 135, line 12 to page 140, line 14, which disclosure and all sequences of linkers are expressly incorporated herein by reference as though explicitly written herein and for use with the present invention, and it is contemplated that any part of such disclosure can be incorporated into one or more claims herein).

In one embodiment of the multispecific ligand, the target antigen may be, or be part of, polypeptides, proteins or nucleic acids, which may be naturally occurring or synthetic. In this respect, the ligand of the invention may bind the target antigen and act as an antagonist or agonist (e.g., EPO receptor agonist). One skilled in the art will appreciate that the choice is large and varied. They may be for instance, human or animal proteins, cytokines, cytokine receptors, where cytokine receptors include receptors for cytokines, enzymes, cofactors for enzymes or DNA binding proteins. Suitable cytokines and growth factors include, but are preferably not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-131, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3a, MIP-313, MIP-4, myeloid progenitor inhibitor factor-1 (MPIF-1), NAP-2, Neurturin, Nerve growth factor, 13-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4, CD4, human chemokine receptors CXCR4 or CCR5, non-structural protein type 3 (NS3) from the hepatitis C virus, TNF-alpha, IgE, IFN-gamma, MMP-12, CEA, *H. pylori*, TB, influenza, Hepatitis E, MMP-12, internalizing receptors that are over-expressed on certain cells, such as the epidermal growth factor receptor (EGFR), ErBb2 receptor on tumor cells, an internalising cellular receptor, LDL receptor, FGF2 receptor, ErbB2 receptor, transferrin receptor, PDGF receptor, VEGF receptor, PsmAr, an extracellular matrix protein, elastin, fibronectin, laminin, a 1-antitrypsin, tissue factor protease inhibitor, PDK1, GSK1, Bad, caspase-9, Forkhead, an antigen of *Helicobacter pylori*, an antigen of *Mycobacterium tuberculosis*, and an antigen of influenza virus. It will be appreciated that this list is by no means exhaustive.

In one embodiment, the multispecific ligand comprises an anti-SA dAb variable domain of the invention and an anti-TNFR1 binding moiety, eg, an anti-TNFR1 dAb. Optionally, the ligand has only one anti-TNFR1 binding moiety (eg, dAb) to reduce the chance of receptor cross-linking. In one embodiment, the anti-SA dAb comprises or consists of the amino acid sequence of any one of SEQ ID NOs: 95 to 101 and 195 to 200 (or an amino acid sequence that is at least 95, 96, 97, 98 or 99% identical to the amino acid sequence of any one of SEQ ID NOs: 95 to 101 and 195 to 200).

In one embodiment, the anti-TNFR1 binding moiety is DOM1h-131-206 disclosed in WO2008149148 (the amino acid sequence of which and the nucleotide sequence of which, as disclosed in that PCT application, are expressly incorporated herein by reference as though explicitly written herein and for use with the present invention, and it is contemplated that any part of such disclosure can be incorporated into one or more claims herein). In one embodiment, the multispecific ligand comprises or consists of the amino acid sequence of DOM1h-131-206 and the amino acid sequence of any one of SEQ ID NOs: 95 to 101 and 195 to 200 (or an amino acid sequence that is at least 95, 96, 97, 98 or 99% identical to the amino acid sequence of any one of SEQ ID NOs: 95 to 101 and 195 to 200).

In one embodiment, the anti-TNFR1 binding moiety or dAb is any such moiety or dAb disclosed in co-pending application U.S. Ser. No. 61/153,746, the disclosure of which is incorporated herein by reference. In one embodiment, the anti-TNFR1 binding moiety comprises an amino acid sequence that is at least 95% identical to the amino acid sequence of DOM1h-574-156, DOM1h-574-72, DOM1h-574-109, DOM1h-574-138, DOM1h-574-162 or DOM1h-574-180 or the amino acid sequence of any anti-TNFR1 dAb disclosed herein. In one embodiment, the multispecific ligand comprises or consists of the amino acid sequence of DOM1h-574-156 and the amino acid sequence of any one of SEQ ID NOs: 95 to 101 and 195 to 200 (or an amino acid sequence that is at least 95, 96, 97, 98 or 99% identical to the amino acid sequence of any one of SEQ ID NOs: 95 to 101 and 195 to 200).

In one embodiment, the ligand of the invention is a fusion protein comprising a variable domain of the invention fused directly or indirectly to one or more polypeptides. For example, the fusion protein can be a "drug fusion" as disclosed in WO2005/118642 (the disclosure of which is incorporated herein by reference), comprising a variable domain of the invention and a polypeptide drug as defined in that PCT application.

As used herein, "drug" refers to any compound (e.g., small organic molecule, nucleic acid, polypeptide) that can be administered to an individual to produce a beneficial, therapeutic or diagnostic effect through binding to and/or altering the function of a biological target molecule in the individual. The target molecule can be an endogenous target molecule encoded by the individual's genome (e.g. an enzyme, receptor, growth factor, cytokine encoded by the individual's genome) or an exogenous target molecule encoded by the genome of a pathogen (e.g. an enzyme encoded by the genome of a virus, bacterium, fungus, nematode or other pathogen). Suitable drugs for use in fusion proteins and conjugates comprising an anti-SA dAb domain of the invention are disclosed in WO2005/118642 and WO2006/059106 (the entire disclosures of which are incorporated herein by reference, and including the entire list of specific drugs as though this list were expressly written herein, and it is contemplated that such incorporation provides disclosure of specific drugs for inclusion in claims herein). For example, the drug can be glucagon-like peptide 1 (GLP-1) or a variant, interferon alpha 2b or a variant or exendin-4 or a variant.

In one embodiment, the invention provides a drug conjugate as defined and disclosed in WO2005/118642 and WO2006/059106, wherein the conjugate comprises a variable domain of the invention. In one example, the drug is covalently linked to the variable domain (eg, the variable domain and the drug are expressed as part of a single polypeptide). Alternatively, in an example, the drug is non-covalently bonded or associated with the variable domain. The drug can be covalently or noncovalently bonded to the variable domain directly or indirectly (e.g., through a suitable linker and/or noncovalent binding of complementary binding partners (e.g., biotin and avidin)). When complementary binding partners are employed, one of the binding partners can be covalently bonded to the drug directly or through a suitable linker moiety, and the complementary binding partner can be covalently bonded to the variable domain directly or through a suitable linker moiety. When the drug is a polypeptide or peptide, the drug composition can be a fusion protein, wherein the polypeptide or peptide, drug and the polypeptide binding moiety are discrete parts (moieties) of a continuous polypeptide chain. As described herein, the polypeptide binding moieties and polypeptide drug moieties can be directly bonded to each other through a peptide bond, or linked through a suitable amino acid, or peptide or polypeptide linker.

A ligand which contains one single variable domain (eg, monomer) of the invention or more than one single variable domain (multimer, fusion protein, conjugate, and dual specific ligand as defined herein) which specifically binds to serum albumin, can further comprise one or more entities selected from, but preferably not limited to a label, a tag, an additional single variable domain, a dAb, an antibody, and antibody fragment, a marker and a drug. One or more of these entities can be located at either the COOH terminus or at the N terminus or at both the N terminus and the COOH terminus of the ligand comprising the single variable domain, (either immunoglobulin or non-immunoglobulin single variable domain). One or more of these entities can be located at either the COOH terminus, or the N terminus, or both the N terminus and the COOH terminus of the single variable domain which specifically binds serum albumin of the ligand which contains one single variable domain (monomer) or more than one single variable domains (multimer, fusion protein, conjugate, and dual specific ligand as defined herein). Non-limiting examples of tags which can be positioned at one or both of these termini include a HA, his or a myc tag. The entities, including one or more tags, labels and drugs, can be bound to the ligand which contains one single variable domain (monomer) or more than one single variable domain (multimer, fusion protein, conjugate, and dual specific ligand as defined herein), which binds serum albumin, either directly or through linkers as described above.

An aspect of the invention provides a fusion product, eg, a fusion protein or fusion with a peptide or conjugate with an NCE (new chemical entity) drug, comprising a polypeptide drug fused or conjugated (for an NCE) to any variable domain as described above, optionally wherein the variable domain comprises or consists of the amino acid sequence of any one of SEQ ID NOs: 95 to 101 and 195 to 200 (or an amino acid sequence that is at least 95, 96, 97, 98 or 99% identical to the amino acid sequence of any one of SEQ ID NOs: 95 to 101 and 195 to 200).

The invention provides a composition comprising a variable domain, fusion protein, conjugate or ligand of any aspect of the invention and a pharmaceutically acceptable diluent, carrier, exipient or vehicle.

Also encompassed herein is an isolated nucleic acid encoding any of the variable domain, fusion proteins, conjugates or ligands described herein, e.g., a ligand which contains one single variable domain (eg, monomer) of the invention or more than one single variable domain (e.g., multimer, fusion protein, conjugate, and dual specific ligand as defined herein) which specifically binds to serum albumin, or which specifically binds both human serum albumin and at least one non-human serum albumin, or functionally active fragments thereof. Also encompassed herein is a vector and/or an expression vector, a host cell (eg, a non-human host cell or a host cell that is not isolated from a human or human embryo) comprising the vector, e.g., a plant or animal cell and/or cell line transformed with a vector, a method of expressing and/or producing one or more variable domains, fusion proteins or ligands which contains one single variable domain (monomer) or more than one single variable domains (e.g., multimer, fusion protein, conjugate, and dual specific ligand as defined herein) which specifically binds to serum albumin, or fragment(s) thereof encoded by said vectors, including in some instances culturing the host cell so that the one or more variable domains, fusion proteins or ligands or fragments thereof are expressed and optionally recovering the ligand which contains one single variable domain (monomer) or more than one single variable domain (e.g., multimer, fusion protein, conjugate, and dual specific ligand as defined herein) which specifically binds to serum albumin, from the host cell culture medium. Also encompassed are methods of contacting a ligand described herein with serum albumin, including serum albumin and/or non-human serum albumin(s), and/or one or more targets other than serum albumin, where the targets include biologically active molecules, and include animal proteins, cytokines as listed above, and include methods where the contacting is in vitro as well as administering any of the variable domains, fusion proteins or ligands described herein to an individual host animal or cell in vivo and/or ex vivo. Preferably, administering ligands described herein which comprises a single variable domain (immunoglobulin or non-immunoglobulin) directed to serum albumin and/or non-human serum albumin(s), and one or more domains directed to one or more targets other than serum albumin, will increase the half life, including the T beta and/or terminal half life, of the anti-target ligand. Nucleic acid molecules encoding the domains, fusion proteins or single domain containing ligands or fragments thereof, including functional fragments thereof, are contemplated herein. Vectors encoding the nucleic acid molecules, including but preferably not limited to expression vectors, are contemplated herein, as are host cells from a cell line or organism containing one or more of these expression vectors. Also contemplated are methods of producing any domain, fusion protein or ligand, including, but preferably not limited to any of the aforementioned nucleic acids, vectors and host cells.

An aspect of the invention provides a nucleic acid comprising a nucleotide sequence encoding a variable domain according to the invention or a multispecific ligand of the invention or fusion protein of the invention.

An aspect of the invention provides a nucleic acid comprising the nucleotide sequence selected from any one of SEQ ID NOs: 1 to 94 and 189 to 194, or a nucleotide sequence that is at least 70, 75, 80, 85, 90, 95, 96, 97, 98 or 99% identical to said selected sequence.

An aspect of the invention provides a vector comprising the nucleic acid of the invention. An aspect of the invention provides an isolated host cell comprising the vector.

Reference is made to WO2008/096158 for details of library vector systems, combining single variable domains, characterization of dual specific ligands, structure of dual specific ligands, scaffolds for use in constructing dual specific ligands, uses of anti-serum albumin dAbs and multispecific ligands and half-life-enhanced ligands, and compositions and formulations of comprising anti-serum albumin dAbs. These disclosures are incorporated herein by reference to provide guidance for use with the present invention, including for domains, ligands, fusion proteins, conjugates, nucleic acids, vectors, hosts and compositions of the present invention.

Sequences of Anti-Serum Albumin VH Single Variable Domains

All variable domains bind at least one species of serum albumin as determined by SPR.

Nucleotide Sequences:

DOM7h-112
SEQ ID NO: 1
GAGGTGCAGCTGTTGGAGTCTGGGGGAGGCTTGGTACAGCCTGGGGG
GTCCCTGCGTCTCTCCTGTGCAGCCTCCGGATTCACCTTTGGGGGGT
ATGTGATGGGTTGGGTCCGCCAGGCTCCAGGGAAGGGTCTAGAGTGG
GTCTCAGCTATTAATAGGTTTGGTTCGTCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGTAGTTTGCGGCATTTTGACTACTGGGGTCAGGG
AACCCTGGTCACCGTCTCGAGC

DOM7h-98
SEQ ID NO: 2
GAGGTGCAGCTGTTGGAGTCTGGGGGAGGCTTGGTACAGCCTGGGGG
GTCCCTGCGTCTCTCCTGTGCAGCCTCCGGATTCACCTTTGGTAATT
ATGCGATGGCGTGGGTCCGCCAGGCTCCAGGGAAGGGTCTAGAGTGG
GTCTCATCGATTGATATGGTTGGTATTAAGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGTTTTCGTATTTTTGACTACTGGGGTCAGGGAAC
CCTGGTCACCGTCTCGAGC

DOM7r-29
SEQ ID NO: 3
GAGGTGCAGCTGTTGGAGTCTGGGGGAGGCTTGGTACAGCCTGGGGG
GTCCCTGCGTCTCTCCTGTGCAGCCTCCGGATTCACCTTTAAGGATT
ATGATATGACTTGGGTCCGCCAGGCTCCAGGGAAGGGTCTAGAGTGG
GTCTCAATGATTTCTTCGTCGGGTCTTTGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGTTTAGGCTGTTTCCTCGGACTTTTGACTACTG
GGGTCAGGGAACCCTGGTCACCGTCTCGAGCG

DOM7r-35
SEQ ID NO: 4
GAGGTGCAGCTGTTGGAGTCTGGGGGAGGCTTGGTACAGCCTGGGGG
GTCCCTGCGTCTCTCCTGTGCAGCCTCCGGATTCACCTTTTCGCTGT
ATAGGATGGTGTGGGTCCGCCAGGCTCCAGGGAAGGGTCTAGAGTGG
GTCTCAATGATTTCTCAGTTTGGTAATCAGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGTTAGGTCTTGGGATCAGACTGGTGGTCGTCGTAC
TTTTGACTACTGGGGTCAGGGAACCCTGGTCACCGTCTCGAGC

DOM7r-36
SEQ ID NO: 5
GAGGTGCAGCTGTTGGAGTCTGGGGGAGGCTTGGTACAGCCTGGGGG
GTCCCTGCGTCTCTCCTGTGCAGCCTCCGGATTCACCTTTAATCATT
ATACGATGGGGTGGGTCCGCCAGGCTCCAGGGAAGGGTCTAGAGTGG
GTCTCATTGATTCATCCGAGTGGTACGGTGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATGGAGTTCGAGGGCGTTTGACTACTGGGGTCAGGG
AACCCTGGTCACCGTCTCGAGC

DOM7r-38
SEQ ID NO: 6
GAGGTGCAGCTGTTGGAGTCTGGGGGAGGCTTGGTACAGCCTGGGGG
GTCCCTGCGTCTCTCCTGTGCAGCCTCCGGATTCACCTTTGATAATA
ATGCGATGGGGTGGGTCCGCCAGGCTCCAGGGAAGGGTCTAGAGTGG
GTCTCAACTATTAGTGCGAATGGTAATGACATACTACGCAGACTC
CGTGAAGGGCCGGTTCACCATCTCCCGCGACAATTCCAAGGACACGC
TGTATCTGCAAATGAACAGCCTGCGTGCCGAGGACACCGCGGTATAT
TACTGTGCGAAAGGTTTTCGTCGGTTTGACTACTGGGGTCAGGGAAC
CCTGGTCACCGTCTCGAGC

DOM7r31
SEQ ID NO: 7
GAGGTGCAGCTGTTGGAGTCTGGGGGAGGCTTGGTACAGCCTGGGGG
GTCCCTGCGTCTCTCCTGTACAGCCTCCGGATTCACCTTTAGGCATT
ATCGTATGGGTTGGGTCCGCCAGGCTCCAGGGAAGGGTCTAGAGTGG
GTCTCATGGATTCGTCCGGATGGTACGTTTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATCTTATATGGGTGATAGGTTTGACTACTGGGGTCA
GGGAACCCTGGTCACCGTCTCGAGCG

DOM7h-32
SEQ ID NO: 8
GAGGTGCAGCTGTTGGAGTCTGGGGGAGGCTTGGTACAGCCTGGGGG
GTCCCTGCGTCTCTCCTGCGCAGCCTCCGGATTCACCTTTGGTAATT
ATCCGATGACGTGGGTCCGCCAGGCTCCAGGGAAGGGTCTGGAGTGG
GTCTCAACTATTAGTTATGGTGGTCTTGCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATGGCGATTAATGGTGTTAGGCCTAGGCGGTTTGA
CTACTGGGGTCAGGGAACCCTGGTCACCGTCTCGAGC

DOM7h-33
SEQ ID NO: 9
GAGGTGCAGCTGTTGGAGTCTGGGGGAGGCTTGGTACAGCCTGGGGG
GTCCCTGCGTCTCTCCTGTGCAGCCTCCGGATTCACCTTTATGGCGT
ATCAGATGGCTTGGGTCCGCCAGGCTCCAGGGAAGGGTCTAGAGTGG
GTCTCAACTATTCATCAGACGGGTTTTTCTACATACTACGCAGACTC
CGTGAAGGGCCGGTTCACCATCTCCCGCGACAATTCCAAGAACACGC
TGTATCGGCAAATGAACAGCCTGCGTGCCGAGGATACCGCGGTATAT
TACTGTGCGAAAGTGCGTTCTATGCGTCCTTATAAGTTTGACTACTG
GGGTCAGGGAACCCTGGTCACCGTCTCGAGC

DOM7h-34
SEQ ID NO: 10
GAGGTGCAGCTGTTGGAGTCTGGGGGAGGCTTGGTACAGCCTGGGGG
GTCCCTGCGTCTCTCCTGTGCAGCCTCCGGATTCACCTTTGGTGATA
AGGCAATGGGGTGGGTCCGCCAGGCTCCAGGGAAGGGTCTAGAGTGG
GTCTCAACGATTAGTGCTCCTGGTAACCGTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGTTTTCGGAATTTTGACTACTGGGGTCAGGGAAC
CCTGGTCACCGTCTCGAGC

DOM7h-83
SEQ ID NO: 11
GAGGTGCAGCTGTTGGAGTCTGGGGGAGGCTTGGTACAGCCTGGGGG
GTCCCTGCGTCTCTCCTGTGCAGCCTCCGGATTCACCTTTGATGGGA
TGCGTATGGGTTGGGTCCGCCAGGCTCCAGGGAAGGGTCTAGAGTGG
GTCTCAGCTATTGAGGTGAATGGTCAGCATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATGGCTCATCCTCAGTCGGGGGTGGCTTTTGACTA
CTGGGGTCAGGGAACCCTGGTCACCGTCTCGAGC

DOM7h-84
SEQ ID NO: 12
GAGGTGCAGCTGTTGGAGTCTGGGGGAGGCTTGGTACAGCCTGGGGG
GTCCCTGCGTCTCTCCTGTGCAGCCTCCGGATTCACCTTTACGCCTG
ATGCTATGGCGTGGGTCCGCCAGGCTCCAGGGAAGGGTCTAGAGTGG
GTCTCATCGATTGGTGTGAATGGTTCTCCGACATACTACGCAGACTC
CGTGAAGGGCCGGTTCACCATCTCCCGCGACAATTCCAGGAACACGC
TGTATCTGCAAATGAACAGCCTGCGTGCCGAGGACACCGCGGTATAT
TACTGTGCGAAAATGGCTCATCCTCAGTCGGGGGTGGCTTTTGACTA
CTGGGGTCAGGGAACCCTGGTCACCGTCTCGAGC

DOM7h-85
SEQ ID NO: 13
GAGGTGCAGCTGTTGGAGTCTGGGGGAGGCTTGGTACAGCCTGGGGG
GTCCCTGCGTCTCTCCTGTGCAGCCTCCGGATTCACCTTTTATCAGT
CGGATATGTCTTGGGTCCGCCAGGCTCCAGGGAAGGGTCTAGAGTGG
GTCTCATCTATTTCTTCCAGGGTCGTTCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATGGCTCATCCTCAGTCGGGGGTGGCTTTTGACTA
CTGGGGTCAGGGAACCCTGGTCACCGTCTCGAGC

DOM7h-86
SEQ ID NO: 14
GAGGTGCAGCTGTTGGAGTCTGGGGGAGGCTTGGTACAGCCTGGGGG
GTCCCTGCGTCTCTCCTGTACAGCCTCCGGATTCACCTTTGCGGCGA
GGGATATGAGTTGGGTCCGCCAGGCTCCAGGGAAGGGTCTGGAGTGG
GTCTCAAGTATTTCTGCTCAGGGTGCTCATACATACTACGCAGACTC
CGTGAAGGGCCGGTTCACCATCTCCCGCGACGATTCCAAGAACACGC
TGTATCTGCAAATGAACAGCCTGCGTGCCGAGGATACCGCGGTATAT
TACTGTGCGAAACCTCGGCATCCTCAGGGGGGGTTACTTTTGACTA
CTGGGGTCAGGGAACCCTGGTCACCGTCTCGAGC

DOM7h-87
SEQ ID NO: 15
GAGGTGCAGCTGTTGGAGTCTGGGGGAGGCTTGGTACAGCCTGGGGG
GTCCCTGCGTCTCTCCTGTGCAGCCTCCGGATTCACCTTTGATAATG
GGGATATGGTTTGGGTCCGCCAGGCTCCAGGGAAGGGTCTAGAGTGG
GTCTCAGGGATTGCGCATAATGGTCGTAATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAAATTTGGGTCAGGGTTTTGACTACTGGGGTCAGGG
AACCCTGGTCACCGTCTCGAGC

DOM7h-88
SEQ ID NO: 16
GAGGTGCAGCTGTTGGAGTCTGGGGGAGGCTTGGTACAGCCTGGGGG
GTCCCTGCGTCTCACCTGTGCAGCCTCCGGATTCACCTTGAATGGTA
CGTCGATGGGTGGGTCCGCCAGGCTCCAGGGAAGGATCTAGAGTGG
GTCTCATCTATTATGCCTGTGGGTTCTCATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATGGCTCATCCTCAGTCGGGGGTGGCTTTTGACTA
CTGGGGTCAGGGAACCCTGGTCACCGTCTCGAGC

DOM7h-89
SEQ ID NO: 17
GAGGTGCAGCTGTTGGAGTCTGGGGGAGGCTTGGTACAGCCTGGGGG
GTCCCTGCGTCTCTCCTGTGCAGCCTCCGGATTCACCTTTGATCATG
CGCCTATGAAGTGGGCCCGCCAGGCTCCAGGGAAGGGTCTAGAGTGG
GTCTCATATATTGGGTCGGCGGGTAATATGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGATGAGGGGCCGTTTGACTACTGGGGTCAGGGAAC
CCTGGTCACCGTCTCGAGC

DOM7h-90
SEQ ID NO: 18
GAGGTGCAGCTGTTGGAGTCTGGGGGAGGCTTGGTACAGCCTGGGGG
GTCCCTGCGTCTCTCCTGTACAGCCTCCGGATTCACCTTTGATGGGA
TGGATATGAGTTGGGTCCGCCAGGCTCCAGGGAAGGGTCTAGAGTGG
GTCTCAAGTATTTCTACGACTGGTGGGACTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTCGGCATCCTCAGGGGGGGTTACTTTTGACTA
CTGGGGTCAGGGAACCCTGGTCACCGTCTCGAGC

DOM7h-91
SEQ ID NO: 19
GAGGTGCAGCTGTTGGAGTCTGGGGGAGGCTTGGTACAGCCTGGGGG
GTCCCTGCGTCTCTCCTGTGCAGCCTCCGGATTCACCTTTGAGGCGG
AGACGATGGCTTGGGTCCGCCAGGCTCCAGGGAAGGGTCTAGAGTGG
GTCTCAACTATTCATTCGGAGGGTTCTCGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTCGGCATCCTCAGGGGGGGTTACTTTTGACTA
CTGGGGTCAGGGAACCCTGGTCACCGTCTCGAGC

DOM7h-92
SEQ ID NO: 20
GAGGTGCAGCTGTTGGAGTCTGGGGGAGGCTTGGTACAGCCTGGGGG
GTCCCTGCGTCTCTCCTGTGCAGCCTCCGGATTCACCTTTAGTACTG
GGGAGATGGCTTGGGTCCGCCAGGCTCCAGGGAAGGGTCTAGAGTGG
GTCTCATCTATTAGTTCGAGTGGTGCTACACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTCGGCATCCTCAGGGGGGGTTACTTTTGACTA
CTGGGGTCAGGGAACCCTGGTCACCGTCTCGAGC

DOM7h-93
SEQ ID NO: 21
GAGGTGCAGCTGTTGGAGTCTGGGGGAGGCTTGGTACAGCCTGGGGG
GTCCCTGCGTCTCTCCTGTGCAGCCTCCGGATTCACCTTTCCTAGTG
CTGATATGGTTTGGGTCCGCCAGGCTCCAGGGAAGGGTCTAGAGTGG
GTCTCACGTATTTCGCCTGAGGGTAATCATACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAACGGCTCCTTCGGATTATGTTTCTTTTGACTACTG
GGGTCAGGGAACCCTGGTCACCGTCTCGAGC

DOM7h-94
SEQ ID NO: 22
GAGGTGCAGCTGTTGGAGTCTGGGGGAGGCTTGGTACAGCCTGGGGG
GTCCCTGCGTCTCTCCTGTGCAGCCTCCGGATTCACCTTTGCGAATG
CGACTATGTCGTGGGTCCGCCAGGCTCCAGGGAAGGGTCTAGAGTGG
GTCTCAGATATTGATCAGGTGGGTCATGCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATATTCGTGGCATCCGGATCTGTTTGACTACTGGGG
TCAGGGAACCCTGGTCACCGTCTCGAGC

DOM7h-95
SEQ ID NO: 23
GAGGTGCGGCTGTTGGAGTCTGGGGGAGGCTTGGTACAGCCTGGGGG
GTCCCTGCGTCTCTCCTGTGCAGCCTCCGGATTCACCTTTAAGGATT
ATGGGATGAATTGGGTCCGCCAGGCTCCAGGGAAGGGTCTAGAGTGG
GTCTCACGGATTAGTAGGAATGGTACTGTTACATACTACGCAGACTC
CGTGAAGGGCCGGTTCACCATCTCCCGCGACAACTCCAAGAACACGC
TGTATCTGCAAATGAACAGCCTGCGTGCCGAGGACACCGCGGTATAT
TACTGTGCGAAATTGGCTGCTCCGGTTCGTCAGAAGGGGATGGATTT
TGACTACTGGGGTCAGGGAACCCTGGTCACCGTCTCGAGC

DOM7h-96
SEQ ID NO: 24
GAGGTGCAGCTGTTGGAGTCTGGGGGAGGCTTGGTACAGCCTGGGGG
GTCCCTGCGTCTCTCCTGTGCAGCCTCCGGATTCACCTTTGAGTGGT
ATAATATGTCGTGGGTCCGCCAGGCTCCAGGGAAGGATCTGGAGTGG
GTCTCATCGATTTCTCATGATGGTTGGAATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGGATGATTGGTTTTGACTACTGGGGTCAGGGAAC
CCTGGTCACCGTCTCGAGC

DOM7h-97
SEQ ID NO: 25
GAGGTGCAGCTGTTGGAGTCTGGGGGAGGCTTGGTACAGCCTGGGGG
GTCCCTGCGTCTCTCCTGTGCAGCCTCCGGATTCACCTTTGATATTT
ATACGATGCATTGGGTCCGCCAGGCTCCAGGGAAGGGTCTAGAGTGG
GTCTCAACTATTGTTCCGCAGGGTACTCCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATCAAGCGTAGGTTTCTTAAGAGGTTTGACTACTG
GGGTCAGGGAACCCTGGTCACCGTCTCGAGC

DOM7h-99
SEQ ID NO: 26
GAGGTGCAGCTGTTGGAGTCTGGGGGAGGCTTGGTACAGCCTGGGGG
GTCCCTGCGTCTCTCCTGTGCAGCCTCCGGATTCACCTTTGCTAGGT
ATGATATGCAGTGGGTCCGCCAGGCTCCAGGGAAGGGTCTAGAGTGG
GTCTCATCGATTAAGAGTAATGGTATGAAGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGCTAGTATGTGGACGTTTGACTACTGGGGTCAGGG
AACCCTGGTCACCGTCTCGAAC

DOM7h-100
SEQ ID NO: 27
GAGGTGCAGCTGTTGGAGTCTGGGGGAGGCTTGGTACAGCCTGGGGG
GTCCCTGCGTCTCTCCTGTGCAGCCTCCGGATTCACCTTTATGTTGT
ATCATATGGGTTCCGCCAGGCTCCAGGGAAGGGTCTAGAGTGG
GTCTCAGCTATTACCGGGGGGTTATCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACTGGGCTTCGGGTGTGCTGTGGCGGAGGAGGTT
TGACTACTGGGGTCAGGGAACCCTGGTCACCGTCTCGAGC

DOM7h-101
SEQ ID NO: 28
GAGGTGCAGCTGTTGGAGTCTGGGGGAGGCTTGGTACAGCCTGGGGG
GTCCCTGCGTCTCTCCTGTGCAGCCTCCGGATTCACCTTTGGTGCTT
ATTCTATGATGTGGGTCCGCCAGGCTCCAGGGAAGGGTCTAGAGTGG
GTCTCACGGATTAGTAGGAATGGTACTGTTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATTAGGTGGAATACTGCTCAGGTGCCTGTGTTTGA
CTACTGGGGTCAGGGAACTCTGGTCACCGTCTCGAGC

DOM7h-102
SEQ ID NO: 29
GAGGTGCAGCTGTTGGAGTCTGGGGGAGGCTTGGTACAGCCTGGGGG
GTCCCTGCGTCTCTCCTGTGCAGCCTCCGGATTCACCTTTGGTCCGT
ATTGGATGGCTTGGGTCCGCCAGGCTCCAGGGAAGGGTCTAGAGTGG
GTCTCAACGATTACGCCTTCGGTCGTGGGACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAAGGGCGTCCTCGTGTTGGTTTGTGGAGGTCGGGGTT
TGACTACTGGGGTCAGGGAACCCTGGTCACCGTCTCGAGC

DOM7h-103
SEQ ID NO: 30
GAGGTGCAGCTGTTGGAGTCTGGGGGAGGCTTGGTACAGCCTGGGGG
GTCCCTGCGTCTCTCCTGTGCAGCCTCCGGATTCACCTTTGGGCAGT
ATGCTATGCAGTGGGTCCGCCAGGCTCCAGGGAAGGGTCTAGAGTGG
GTCTCATCTATTAATATTACTGGTTCTACTACATACTACGCAGACTC
CGTGAAGGGCCGGTTCACCATCTCCCGCGACAATTCCAAGAACACGC
TGTATCTGCAGATGAACAGCCTGCGTGCCGAGGACACCGCGGTATAT
TACTGTGCGAAAGGTTTTAGGTCTTTTGACTACTGGGGTCAGGGAAC
CCTGGTCACCGTCTCGAGC

DOM7h-106
SEQ ID NO: 31
GAGGTGCAGCTGTTGGAGTCTGGGGGAGGCTTGGTACAGCCTGGGGG
GTCCCTGCGTCTCTCCTGTGCAGCCTCCGGATTCACCTTTGCTGGTT
ATACGATGTCGTGGGTCCGCCAGGCTCCAGGGAAGGGTCTAGAGTGG
GTCTCAACGATTTCGGGTTTTGGTTGGACTACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAAAGGCTGGGGATGCGTTTTGACTACTGGGGTCAGGG
AACCCTGGTCACCGTCTCGAGC

DOM7h-109
SEQ ID NO: 32
GAGGTGCAGCTGTTGGAGTCTGGGGGAGGCTTGGTACAGCCTGGGGG
GTCCCTGCGTCTCTCCTGTGCAGCCTCCGGATTCACCTTTGGTCCGT
ATTCGATGGGGTGGGTCCGCCAGGCTCCAGGGAAGGGTCTAGAGTGG
GTCTCATTTATTCATTCTGATGGTCGTCATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAAGACGCCTTATAGGTTTGACTACTGGGGTCAGGG
AACCCTGGTCACCGTCTCGAGC

DOM7h-111
SEQ ID NO: 33
GAGGTGCAGCTGTTGGAGTCTGGGGGAGGCTTGGTACAGCCTGGGGG
GTCCCTGCGTCTCTCCTGTGCAGCCTCCGGATTCACCTTTGGGCAGT
ATGCTATGCAGTGGGTCCGCCAGGCTCCAGGGAAGGGTCTAGAGTGG
GTCTCATCTATTAATATTACTGGTTCTACTACATACTACGCAGACTC
CGTGAAGGGCCGGTTCACCATCTCCCGCGACAATTCCAAGAACACGC
TGTATCTGCAGATGAACAGCCTGCGTGCCGAGGACACCGCGGTATAT
TACTGTGCGAAAGGTTTTAGGTCTTTTGACTACTGGGGTCAGGGAAC
CCTGGTCACCGTCTCGAGC

DOM7h-114
SEQ ID NO: 34
GAGGTGCAGCTGTTGGAGTCTGGGGGAGGCTTGGTACAGCCTGGGGG
GTCCCTGCGTCTCTCCTGTGCAGCCTCCGGATTCACCTTTAGGCGGT
ATGCGATGTCTTGGGTCCGCCAGGCTCCAGGGAAGGGTCTAGAGTGG
GTCTCAACGATTTCGCCTTATGGTCCTACATACTACGCAGACTC
CGTGAAGGGCCGGTTCACCATCTCCCGCGACAATTCCAAGAACACGC
TGTATCTGCAAATGAATAGCCTGCGTGCCGAGGACACCGCGGTATAT
TACTGTGCGAAAGCTTATTATGGTGGGTTTGACTACTGGGGTCAGGG
AACCCTGGTCACCGTCTCGAGC

DOM7r-34
SEQ ID NO: 35
GAGGTGCAGCTGTTGGAGTCTGGGGGAGGCTTGGTACAGCCTGGGGG
GTCCCTGCGTCTCTCCTGTGCAGCCTCCGGATTCACCTTTGATGCTT
ATGCTATGGGTTGGGTCCGCCAGGCTCCAGGGAAGGGTCTAGAGTGG
GTCTCAAAGATTGATTCTCCTGGTTGGAGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATCGGCTCGGATGCGTTCTCGGCATTTTGACTACTG
GGGTCAGGGAACCCTGGTCACCGTCTCGAGC

DOM7r-37
SEQ ID NO: 36
GAGGTGCAGCTGTTGGAGTCTGGGGGAGGCTTGGTACAGCCTGGGGG
GTCCCTGCGTCTCTCCTGTGCAGCCTCCGGATTCACCTTTAAGGATT
ATGGGATGAATTGGGTCCGCCAGGCTCCAGGGAAGGGTCTAGAGTGG
GTCTCACGATTAGTAGGAATGGTACTGTTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATTAGGTGGAATACTGCTCAGGTGCCTGTGTTTGA
CTACTGGGGTCAGGGAACTCTGGTCACCGTCTCGAGC

DOM7r-39
SEQ ID NO: 37
GAGGTGCAGCTGTTGGAGTCTGGGGGAGGCTTGGTACAGCCTGGGGG
GTCCCTGCGTCTCTCCTGTGCAACCTCCGGATTCACCTTTCCGTCTT
ATACGATGGGTTGGGTCCGCCAGGCTCCAGGGAAGGGTCTAGAGTGG
GTCTCACGTATTTCTCGTACTGGGAATTATACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAACCTATGTATAATAGGGGGTCTTCGTATTTTGACTA
CTGGGGTCAGGGAACCCTGGTCACCGTCTCGAGC

DOM7r-40
SEQ ID NO: 38
GAGGTGCAGCTGTTGGAGTCTGGGGGAGGCTTGGTACAGCCTGGGGG
GTCCCTGCGTCTCTCCTGTGCAGCCTCCGGATTCACCTTTTCGCAGT
ATCAGATGTCGTGGGTCCGCCAGGCTCCAGGGAAGGGTCTAGAGTGG
GTCTCATCGATTTCGCCTACGGGTATTCAGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAAGGCTTATTGGGATGCCGTATGTTGAGGATACTTT
TGACTACTGGGGTCAGGGAACCCTGGTCACCGTCTCGAGC

DOM7r-41
SEQ ID NO: 39
GAGGTGCAGCTGTTGGAGTCTGGGGGAGGCTTGGTACAGCCTGGGGG
GTCCCTGCGTCTCTCCTGTGCAGCCTCCGGATTCACCTTTATGGAGT
ATGAGATGGAGTGGGTCCGCCAGGCTCCAGGGAAGGGTCTAGAGTGG
GTCTCAGGTATTACTAATTCTTGGTTCTGGGACATACTACGCAGACTC
CGTGAAGGGCCGGTTCACCATCTCCCGCGACAACTCCAAGAACACGC
TGTATCTGCAAATGAACAGCCTGCGTGCCGAGGACACCGCGGTATAT
TACTGTGCGATAATGCAGCATCCTCAGGCGACTGGGGGAGGGTTGG
GTTTGACTACTGGGGTCAGGGAACCCTGGTCACCGTCTCGAGC

DOM7r-42
SEQ ID NO: 40
GAGGTGCAGCTGTTGGAGTCTGGGGGAGGCTTGGTACAGCCTGGGGG
GTCCCTGCGTCTCTCCTGTGCAGCCTCCGGATTCACCTTTCCGAGGT
ATACTATGAAGTGGGTCCGCCAGGCTCCAGGGAAGGGTCTAGAGTGG
GTCTCATCGATTGATAGGACGGGTCGTAAGACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAAGAGTCGTTGGTTTCGTTTGACTACTGGGGTCAGGG
AACCCTGGTCACCGTCTCGAGC

DOM7r-43
SEQ ID NO: 41
GAGGTGCAGCTGTTGGAGTCTGGGGGAGGCTTGGTACAGCCTGGGGG
GTCCCTGCGTCTCTCCTGTGCAGCCTCCGGATTCACCTTTGGTGGTT
ATACGATTTTCTCGTGATGGTAATTATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGATATTGGTATGGGTTTTGACTACGGGGGCGGGG
AACCCTGGTCACCGTCTCGAGC

DOM7r-44
SEQ ID NO: 42
GAGGTGCAGCTGTTGGAGTCTGGGGGAGGCTTGGTACAGCCTGGGGG
GTCCCTGCGTCTCTCCTGTGCAGCCTCCGGATTCACCTTTGAGATTT
ATGGATGCATTGGGTCCGCCAGGCTCCAGGGAAGGGTCTAGAGTGG
GTCTCAACGATTAGTTCGGGTGGTAAGGGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATCGCGTACTATGTATTTTCGTGTTAGGGAGGCTTT
TGACTACTGGGGTCAGGGAACCCTGGTCACCGTCTCGAGC

DOM7r-45

SEQ ID NO: 43

GAGGTGCAGCTGTTGGAGTCTGGGGGAGGCTTGGTACAGCCTGGGGG
GTCCCTGCGTCTCCTGTGCAGCCTCCGGATTCACCTTTCGTGCTT
ATAGGATGATGTGGGTCCGCCAGGCTCCAGGGAAGGGTCTGGAGTGG
GTCTCATCTATTGATCCTGATGGTGCGGTTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGGAACATTTTGATCTTGCGATGCCGAATCCGAATGCGAA
GTTTGACTACTGGGGTCAGGGAACCCTGGTCACCGTCTCGAGC

DOM7r-46

SEQ ID NO: 44

GAGGTGCAGCTGTTGGAGTCTGGGGGAGGCTTGGTACAGCCTGGGGG
GTCCCTGCGCCTCTCCTGTGCAGCCTCCGGATTCACCTTTTCTCGTT
ATCAGATGTCTTGGGTCCGCCAGGCTCCAGGGAAGGGTCTGGAGTGG
GTCTCATCTATTAAGTCGAATGGTTCTTGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTAGTCGGCAGAGTTTTCAGTATCCGAGTTTTGA
CTACTGGGGTCAGGGAACCCTGGTCACCGTCTCGAGC

DOM7r-47

SEQ ID NO: 45

GAGGTGCAGCTGTTGGAGTCTGGGGGAGGCTTGGTACAGCCTGGGGG
GTCCCTGCGTCTCTCCTGTGCAGCCTCCGGATTCACCTTTGGGCGTT
ATAAGATGGGTTGGGTCCGCCAGGCTCCAGGGAAGGGTCTAGAGTGG
GTCTCATCTATTTCGCCTACGGGTTCGTCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAACTGGGTATGTTATGGTTGAGCATTTTGACTACTG
GGGTCAGGGAACCCTGGTCACCGTCTCGAGC

DOM7r-48

SEQ ID NO: 46

GAGGTGCAGCTGTTGGAGTCTGGGGGAGGCTTGGTACAGCCTGGGGG
GTCCCTGCGTCTCTCCTGTGCAGCCTCCGGATTCACCTTTAGTGATT
ATCCGATGAAGTGGGTCCGCCAGGCTCCAGGGAAGGGTCTGGAGTGG
GTCTCAACTATTAATTCTTCGGGTACGATTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCGTTGTTGCCGTTTGACTACTGGGGTCAGGGAAC
CCTGGTCACCGTCTCGAGC

DOM7r-49

SEQ ID NO: 47

GAGGTGCAGCTGTTGGAGTCTGGGGGAGGCTTGGTACAGCCTGGGGG
GTCCCTGCGTCTCTCCTGTGCAGCCTCCGGATTCACCTTTGCTAGGT
ATAGGATGTGTTGGGTCCGCCAGGCTCCAGGGAAGGGTCTAGAGTGG
GTCTCATGTATTCGGGATCCGGGTTTTCCGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATGTTCGCCGTCTTCTACGCAGTGTACGGGCTTTT
TGACTACTGGGGTCAGGGAACCCTGGTCACCGTCTCGAGC

DOM7r-50

SEQ ID NO: 48

GAGGTGCAGCTGTTGGAGTCTGGGGGAGGCTTGGTACAGCCTGGGGG
GTCCCTGCGTCTCTCCTGTGCAGCCTCCGGATTCACCTTTAGGTTTT
ATGGGATGGCGTGGGTCCGCCAGGCTCCAGGGAAGGGTCTAGAGTGG
GTCTCACTTATTGATCCTCCTGGTGGGGCACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATGGAGAGGCGGCATCTTAAGAGTGGTCATAAGGG
GTTTGACTACTGGGGTCAGGGAACCCTGGTCACCGTCTCGAGC

DOM7r-51

SEQ ID NO: 49

GAGGTGCAGCTGTTGGAGTCTGGGGGAGGCTTGGTACAGCCTGGGGG
GTCCCTGCGTCTCTCCTGTGCAGCCTCCGGATTCACCTTTACGGAGT
ATGATATGATGTGGGTCCGCCAGGCTCCAGGGAAGGGTCTAGAGTGG
GTCTCATCTATTAGTCATAGGGGTGAGAAGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGATAAGCGTTATCGGGGTCTCAGCATTATTTGA
CTACTGGGGTCAGGGAACCCTGGTCACCGTCTCGAGC

DOM7r-52

SEQ ID NO: 50

GAGGTGCAGCTGTTGGAGTCTGGGGGAGGCTTGGTACAGCCTGGGGG
GTCCCTGCGTCTCTCCTGTGCAGCCTCCGGATTCACCTTTCGGAGTT
ATGATATGGGTTGGGCCCGCCAGGCTCCAGGGAAGGGTCTAGAGTGG
GTCTCAACTATTGGGTCGAATGGTGCTAATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACTTATGGGTATGTTGACTACTGGGGTCAGGGAAC
CCTGGTCACCGTCTCGAGC

DOM7r-53

SEQ ID NO: 51

GAGGTGCAGCTGTTGGAGTCTGGGGGAGGCTTGGTACAGCCTGGGGG
GTCCCTGCGTCTCTCCTGTGCAGCCTCCGGATTCACCTTTGAGCGTT
ATTCTATGAGGTGGGTCCGCCAGGCTCCAGGGAAGGGTCTAGAGTGG
GTCTCAACGATTGGTTCGACGGGTAAGTGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGGCGTGGGTTGGTTTCTTTTGACTACTGGGGTCA
GGGAACCCTGGTCACCGTCTCGAGC

DOM7r-54

SEQ ID NO: 52

GAGGTGCAGCTGTTGGAGTCTGGGGGAGGCTTGGTACAGCCTGGGGG
GTCCCTGCGTCTCTCCTGTGCAGCCTCCGGATTCACCTTTAGGCGTT
ATTCGATGTCTTGGGTCCGCCAGGCTCCAGGGAAGGGTCTAGAGTGG
GTCTCATCTATTGATCGGTCTGGTAGGATGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATCTCGGCTGTCTTGACGGGTTCTGAGGGTCATAA
TTTTGACTACTGGGGTCAGGGAACCCTGGTCACCGTCTCGAGC

DOM7r-55

SEQ ID NO: 53

GAGGTGCAGCTGTTGGAGTCTGGGGGAGGCTTGGTACAGCCTGGGGG
GTCCCTGCGTCTCTCCTGTGCAGCCTCCGGATTCACCTTTAAGTGGT
ATCCGATGAAGTGGGTCCGCCAGGCTCCAGGGAAGGGTCTAGAGTGG
GTCTCAACTATTGCTTATGATGGTGTTCAGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATTGGGTCCGACTAGTCGTGTGTTTGCTGCTACTGA
TTTTGACTACTGGGGTCAGGGAACCCTGGTCACCGTCTCGAGC

DOM7r-56

SEQ ID NO: 54

GAGGTGCAGCTGTTGGAGTCTGGGGGAGGCTTGGTACAGCCTGGGGG
GTCCCTGCGTCTCTCCTGTGCAGCCTCCGGATTCACCTTTCCGAATT
ATGCGATGAAGTGGGCCCGCCAGGCTCCAGGGAAGGGTCTAGAGTGG
GTCTCAACTATTGATACGAGTGGTAGTACTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACTTACTCATCCTATGGCGCCGCGTCCGGCTTTTGA
CTACTGGGGTCAGGGAACCCTGGTCACCGTCTCGAGC

DOM7r-57

SEQ ID NO: 55

GAGGTGCAGCTGTTGGAGTCTGGGGGAGGCTTGGTACAGCCTGGGGG
GTCCCTGCGTCTCTCCTGTGCAGCCTCCGGATTCACCTTTGATCTTA
CGGAGATGGCGTGGGTCCGCCAGGCTCCAGGGAAGGGTCTGGAGTGG
GTCTCATCGATTGGGCCTTGGGGTACTCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATTTCGCATCCTCAGGCGATGTATCATACGTTTGA
CTACTGGGGTCAGGGAACCCTGGTCACCGTCTCGAGC

DOM7r-58

SEQ ID NO: 56

GAGGTGCAGCTGTTGGAGTCTGGGGGAGGCTTGGTACAGCCTGGGGG
GTCCCTGCGTCTCTCCTGTGCAGCCTCCGGATTCACCTTTGCGCATC
AGGATATGACGTGGGTCCGCCAGGCTCCAGGGAAGGGTCTAGAGTGG
GTCTCAGATATTGATCATTCGGGTTCGTATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATGTGGCATCCGCAGGGGGGACTTTTGACTACTG
GGGTCAGGGAACCCTGGTCACCGTCTCGAGC

DOM7r-59
SEQ ID NO: 57
GAGGTGCAGCTGTTGGAGTCTGGGGGAGGCTTGGTACAGCCTGGGGG
GTCCCTGCGTCTCTCCTGTGCAGCCTCCGGATTCACCTTTGGTTCTA
AGGATATGTCGTGGGTCCGCCAGGCTCCAGGGAAGGGTCTAGAGTGG
GTCTCAACGATTGGGGCGAATGGTAAGGCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGGAAGCGGGTCATCCTCAGGCGCCGTCTTTTAAGAGTTT
TGACTACTGGGGTCAGGGAACCCTGGTCACCGTCTCGAGC

DOM7r-60
SEQ ID NO: 58
GAGGTGCAGCTGTTGGAGTCTGGGGGAGGCTTGGTACAGCCTGGGGG
GTCCCTGCGTCTCTCCTGTGCAGCCTCCGGATTCACCTTTCTGAATG
CGGAGATGAGTTGGGTCCGCCAGGCTCCAGGGAAGGGTCTAGAGTGG
GTCTCAACTATTGATCGGGATGGTGCTAATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACTTCCTCCGCCGATGTCGCCAAGAAGTTTGACTA
CTGGGGTCAGGGAACCCTGGTCACCGTCTCGAGC

DOM7r-61
SEQ ID NO: 59
GAGGTGCAGCTGTTGGAGTCTGGGGGAGGCTTGGTACAGCCTGGGGG
GTCCCTGCGTCTCTCCTGTGCAGCCTCCGGATTCACCTTTGAGAGGG
AGGGTATGATGTGGGTCCGCCAGGCTCCAGGGAAGGGTCTAGAGTGG
GTTTCAACTATTGATCGTATGGGTAGGTATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAAGGGATTCGCATCCTATGGGGTTTGACTACCGGGG
TCAGGGAACCCTGGTCACCGTCTCGAGC

DOM7r-62
SEQ ID NO: 60
GAGGTGCAGCTGTTGGAGTCTGGGGGAGGCTTGGTACAGCCTGGGGG
GTCCCTGCGTCTCTCCTGTGCAGCCTCCGGGTTCACCTTTGAGAATG
AGAAGATGAGTTGGGTCCGCCAGGCTCCAGGGAAGGGTCTAGAGTGG
GTCTCATCGATTGGTCCTACGGGTAGTGGTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAACTCCTCATCCGCAGGTTTCTAGTTTTGACTACTG
GGGTCAGGGAACCCTGGTCACCGTCTCGAGC

DOM7r-63
SEQ ID NO: 61
GAGGTGCAGCTGTTGGAGTCTGGGGGAGGCTTGGTACAGCCTGGGGG
GTCCCTGCGTCTCTCCTGTGCAGCCTCCGGATTCACCTTTGAGATTG
ATCATATGGGGTGGGTCCGCCAGGCTCCAGGGAAGGGTCTAGAGTGG
GTCTCAGAGATTGCGCTTCGGGTGATCGTACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAAGTGATTTGTCAGAATCAGTGTCTGTTTGACTACTG
GGGTCAGGGAACCCTGGTCACCGTCTCGAGC

DOM7r-64
SEQ ID NO: 62
GAGGTGCAGCTGTTGGAGTCTGGGGGAGGCTTGGTACAGCCTGGGGG
GTCCCTGCGTCTCTCCTGTGCAGCCTCCGGATTCACCTTTAGGGATT
CTGAGATGTCGTGGGTCCGCCAGGCTCCAGGGAAGGGTCTAGAGTGG
GTCTCATTTATTACTTCTGATGGTCGGATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTAGTCTGCCTCATGTTACGGCTTTTGACTACTG
GGGTCAGGGAACCCTGGTCACCGTCTCGAGC

DOM7r-65
SEQ ID NO: 63
GAGGTGCAGCTGTTGGAGTCTGGGGGAGGCTTGGTACAGCCTGGGGG
GTCCTGCGTCTCTCCTGTGCAGCCTCCGGATTCACCTTTAGGGATT
AGACGATGAGTTGGGCCGCCAGGCTCCAGGGAAGGGTCTAGAGTGG
GTCTCATCGATTGGGGATGCTGGTATGCCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGGGAGCCGATTTATGTTCATACGACTCATTTTGA
CTACTGGGGTCAGGGAACCCTGGTCACCGTCTCGAGC

DOM7r-66
SEQ ID NO: 64
GAGGTGCAGCTGTTGGAGTCTGGGGGAGGCTTGGTACAGCCTGGGGG
GTCCCTGCGTCTCTCCTGTGCAGCCTCCGGATTCACCTTTCCGCATG
GTAAGATGGGGTGGGTCCGCCAGGCTCCAGGGAAGGGTCTAGAGTGG
GTCTCATGGATTGCTGGGTCTGGTGATATGACATACTACGCAGACTC
CGTGAAGGGCCGGTTCACCATCTCCCGCGACAATTCCAAGAACACGC
TGTATCTGCAAATGAACAGCCTGCGTCCGAGGACACCGCGGTATAT
TACTGTGCGAAATTGGGTCATCCTCAGCGGGTTTTGACTACTGGGG
TCAGGGAACCCTGGTCACCGTCTCGAGC

DOM7r-67
SEQ ID NO: 65
GAGGTGCAGCTGTTGGAGTCTGGGGGAGGCTTGGTACAGCCTGGGGG
GTCCCTGCGTCTCTCCTGTGCAGCCTCCGGATTCACCTTTGGGACTT
CTGATATGTCGTGGGTCCGCCAGGCCCCAGGGAAGGGTCTAGAGTGG
GTCTCAACTATTGATTCTGGGGGTAGTTTTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTCGGCATCCTCAGGGGGGGGTTACTTTTGACTA
CTGGGGTCAGGGAACCCTGGTCACCGTCTCGAGC

DOM7r-68
SEQ ID NO: 66
GAGGTGCAGCTGTTGGAGTCTGGGGGAGGCTTGGTACAGCCTGGGGG
GTCCCTGCGTCTCTCCTGTGCAGCCTCCGGATTCACCTTTGAGCATG
TTCCTATGGCTTGGGTCCGCCAGGCTCCAGGGAAGGGTCTAGAGTGG
GTCTCACGGATTAGTGAGCAGGGTAGTAATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGTGCAGCATCCTATGTCTCCGCATGAGTTTGACTA
CTGGGGTCAGGGAACCCTGGTCACCGTCTCGAGC

DOM7r-69
SEQ ID NO: 67
GAGGTGCAGCTGTTGGAGTCTGGGGGAGGCTTGGTACAGCCTGGGGG
GTCCCTGCGTCTCTCCTGTGCAGCCTCCGGATTCACCTTTGAGCAGG
GTATGATGTCGTGGGTCCGCCAGGCTCCAGGGAAGGGTCTAGAGTGG
GTCTCATCGATTAATCTGGTGGTCAGTTTACATACTACGCAGACTC
CGTGAAGGGCCGGTTCACCATCTCCCGCGACAATTCCAGGAACACGC
TGTATCTGCAAATGAACAGCCTGCGTGCCGAGGACACCGCGGTATAT
TACTGTGCGGAAGATCTGGGGCCGGGTTTTGACTACTGGGGTCAGGG
AACCCTGGTCACCGTCTCGAGC

DOM7r-70
SEQ ID NO: 68
GAGGTGCAGCTGTTGGAGTCTGGGGGAGGCTTGGTACAGCCTGGGGG
GTCCCTGCGTCTCTCCTGTGCAGCCTCCGGATTCACCTTTGAGCGTT
GGCTCTATGTCTTGGCCGCCAGGCTCCAGGGAAGGGTCTAGAGTGG
GTCTCAACTATTGATAGGTCTGGTAATACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAAGTTTTGCATCCTCAGGCGGGTCTGCTTTTGACTA
CTGGGGTCAGGGAACCCTGGTCACCGTCTCGAGC

DOM7r-71
SEQ ID NO: 69
GAGGTGCAGCTGTTGGAGTCTGGGGGAGGCTCGGTACAGCCTGGGGG
GTCCCTGCGTCTCTCCTGTGCAGCCTCCGGATTCACCTTTGGGGGTA
GTGATATGGGTTCCGCCAGGCTCCAGGGAAGGGTCTAGAGTGG
GTCTCATATATTGATAATCAGGGTATAATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATATAAGCTTCTGGGTCCGTCTACTGAGTTTGACTA
CTGGGGTCAGGGAACCCTGGTCACCGTCTCGAGC

DOM7r-72
SEQ ID NO: 70
GAGGTGCAGCTGTTGGAGTCAGGGGGAGGCTTGGTACAGCCTGGGGG
GTCCCTGCGTCTCTCCTGTGCAGCCTCCGGATTCACCTTTAGTAGTG
ATGTTATGTCTTGGGTCCGCCAGGCTCCAGGGAAGGGTCTAGAGTGG
GTCTCAAGTATTACGAGGTCGGGTATGCAGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATATGCGCATCCTCAGTCGGCTGTTGAGTTTGACTA
CTGGGGTCAGGGAACCCTGGTCACCGTCTCGAGC

DOM7r-73
SEQ ID NO: 71
GAGGTGCAGCTGTTGGAGTCTGGGGGAGGCTTGGTACAGCCTGGGGG
GTCCCTGCGTCTCTCCTGTGCAGCCTCCGGATTCACCTTTCGTAATG
AGCCGATGAGTTGGGTGCGCCAGGCTCCAGTGAAGGGTCTAGAGTGG
GTCTCAACTATTTCGCTGATGGTAGTGGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACATGGTCATCCTCAGGGGGCTCGTTTTGACTACTG
GGGTCAGGGAACCCTGGTCACCGTCTCGAGC

DOM7r-74
SEQ ID NO: 72
GAGGTGCAGCTGTTGGAGTCTGGGGGAGGCTTGGTACAGCCTGGGGG
GTCCCTGCGTCTCTCCTGTGCAGCCTCCGGATTCACCTTTTTGAATA
GTGAGATGTCGTGGGTCCGCCAGGCTCCAGGGAAGGGTCTGGAGTGG
GTCTCAACTATTGGGTATGCGGGTACTCCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTCGGCATCCTCAGGGGGGGTTACTTTTGACTA
CTGGGGTCAGGGAACCCTGGTCACCGTCTCGAGC

DOM7r-75
SEQ ID NO: 73
GAGGTGCAGCTGTTGGAGTCTGGGGGAGGCTTGGTACAGCCTGGGGG
GTCCCTGCGTCTCTCCTGTGCAGCCTCCGGATTCACCTTTGCTCGGG
GGCCTATGTCTTGGGTCCGCCAGGCTCCAGGGAAGGGTCTAGAGTGG
GTCTCAACTATTACGAATGATGGTACGTCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGGAACCGCCTCATAGTGGTAGGCCTATGTTTGACTACTG
GGGTCAGGGAACCCTGGTCACCGTCTCGAGC

DOM7r-76
SEQ ID NO: 74
GAGGTGCAGCTGTTGGAGTCTGGGGGAGGCTTGGTACAGCCTGGGGG
GTCCCTGCGTCTCTCCTGTGCAGCCTCCGGATTCACCTTTCAGCGGA
CTGCTATGTCTTGGGTCCGCCAGGCTCCAGGGAAGGGTCTTGAGTGG
GTCTCATCTATTGAGGCTTCGGTCGGTATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACAGTCGCATCCTCAGAATGGTCGTTTTGACTACTG
GGGTCAGGGAACCCTGGTCACCGTCTCGAGC

DOM7r-77
SEQ ID NO: 75
GAGGTGCAGCTGTTGGAGTCTGGGGGAGGCTTGGTACAGCCTGGGGG
GTCCCTGCGTCTCTCCTGTGCAGCCTCCGGATTCACCTTTGATGCGT
CGGAGATGGCTTGGGTCCGCCAGGCTCCAGGGAAGGGTCTAGAGTGG
GTCTCAAGTATTACGGTTTATGGTGATAGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTCGGCATCCTCAGGGGGGGGTTACTTTTGACTA
CTGGGGTCAGGGAACCCTGGTCACCGTCTCGAGC

DOM7r-78
SEQ ID NO: 76
GAGGTGCAGCTGTTGGAGTCTGGGGGAGGCTTGGTACAGCCTGGGGG
GTCCCTGCGTCTCTCCTGTGCAGCCTCCGGATTCACCTTTGATGATT
CGCATATGGCTTGGGTCCGCCAGGCTCCAGGGAAGGGTCTAGAGTGG
GTCTCAAGGATTTCGAGGGAGGGTAAGGCACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGGCACCGAATGATCAGTCGGCGGCTTTTGACTACTGGGG
TCAGGGAACCCTGGTCACCGTCTCGAGC

DOM7r-79
SEQ ID NO: 77
GAGGTGCAGCTGTTGGAGTCTGGGGGAGGCTTGGTACAGCCTGGGGG
GTCCCTGCGTCTCTCCTGTGCAGCCTCCGGATTCACCTTTGATATGA
GTGAGATGTCGTGGGTCCGCCAGGCTCCAGGGAAGGGTCTAGAGTGG
GTCTCAGCTATTACTTCGGATGGTAGTTCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACCTAGTCTGCCTCATGTTACGGCTTTTGACTACTG
GGGTCAGGGAACCCTGGTCACCGTCTCGAGC

DOM7r-80
SEQ ID NO: 78
GAGGTGCAGCTGTTGGAGTCTGGGGGAGGCTTGGTACAGCCTGGGGG
GTCCCTGCGTCTCTCCTGTGCAGCCTCCGGATTCACCTTTGAGAGGT
CTACTATGCATTGGGTCCGCCAGGCTCCAGGGAAGGGTCTAGAGTGG
GTCTCAGAGATTGATGCTCTGGGTACGGATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATCGTCTGATCATCCTCAGAATAGTTTTGACTACTG
GGGTCAGGGAACCCTGGTCACCGTCTCGAGC

DOM7r-81
SEQ ID NO: 79
GAGGTGCAGCTGTTGGAGTCTGGGGGAGGCTTGGTACAGCCTGGGGG
GTCCCTGCGTCTCTCCTGTGCAGCCTCCGGATTCACCTTTGAGCCTC
GTGAGATGTATTGGGCCCGCCAGGCTCCAGGGAAGGGTCTAGAGTGG
GTCGCACGGATTGGTTGGGATGGTCATACGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACAGCTGGGTCAGTTTGACTACTGGGGTCAGGGAAC
CCTGGTCACCGTCTCGAGC

DOM7r-82
SEQ ID NO: 80
GAGGTGCAGCTGTTGGAGTCTGGGGGAGGCTTGGTACAGCCTGGGGG
GTCCCTGCGTCTCTCCTGTGCAGCCTCCGGATTCACCTTTGATGCTT
ATAGTATGATGTGGGTCCGCCAGGCTCCAGGGAAGGGTCTAGAGTGG
GTCTCAACTATTGGTAGGTGGGGTGAGATTACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAACGTCGTTATATTGGGCTTATATGCTTTCGGGTCG
TTTTGACTACTGGGGTCAGGGAACCCTGGTCACCGTCTCGAGC

DOM7r-83
SEQ ID NO: 81
GAGGTGCAGCTGTTGGAGTCTGGGGGAGGCTTGGTACAGCCTGGGGG
GTCCCTGCGTCTCTCCTGTGCAGCCTCCGGATTCACCTTTATGCGGT
ATCCTATGGTGTGGGTCCGCCAGGCTCCAGGGAGGGGTCTAGAGTGG
GTCATCTATTTCTCCTGCTGGTTATGGTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGTCATGAGATTAGTCGTTTTCTCGTTGGTCTTC
TTTTGACTACTGGGGTCAGGGAACCCTGGTCACCGTCTCGAGC

DOM7r-84
SEQ ID NO: 82
GAGGTGCAGCTGTTGGAGTCTGGGGGGGCTTGGTACAGCCTGGGGG
GTCCCTGCGTCTCTCCTGTGCAGCCTCCGGATTCACCTTTCGGAAGT
ATAGGATGTCGTGGGTCCGCCAGGCTCCAGGGAAGGGTCTAGAGTGG
GTCTCATCTATTGCGAGGAATGGTCGTTCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAACTACGTCTGGGTTTGACTACTGGGGTCAGGGAAC
CCTGGTCACCGTCTCGAGC

DOM7r-85
SEQ ID NO: 83
GAGGTGCAGCTGTTGGAGTCTGGGGGAGGCTTGGTACAGCCTGGGGG
GTCCCTGCGTCTCTCCTGTGCAGCCTCCGGATTCACCTTTAATAAGA
AGGAGATGGGTCCGCCAGGCTCCAGGGAAGGGTCTAGAGTGG
GTCTCATCTATTGATGTGAGTGGTAATGTTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAATGGCTCATCCTCAGTCGGGGTGGCTTTTGACTA
CTGGGGTCAGGGAACCCTGGTCACCGTCTCGAGC

DOM7r-88
SEQ ID NO: 84
GAGGTGCAGCTGTTGGAGTCTGGGGGAGGCTTGGTACAGCCTGGGGG
GTCCCTGCGTCTCTCCTGTGCAGCCTCCGGATTCACCTTTCGGATGT
ATGATATGCTGGGTCCGCCAGGCTCCAGGGAAGGGTCTAAAGTGG
GTCTCAACTATTCTGTCTTCTGGTAAGGGTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATTGGCTCATCCTCAGAAGGGTAGTATTTTGACTA
CCGGGGTCAGGGAACCCTGGTCACCGTCTCGAGC

DOM7r-89
SEQ ID NO: 85
GAGGTGCAGCTGTTGGAGTCTGGGGGAGGCTTGGTACAGCCTGGGGG
GTCCCTGCGTCTCTCCTGTGCAGCCTCCGGATTCACCTTTCATCAGG
GTCCTATGGGTGGGTCCGCCAGGCTCCAGGGAAGGGTCTAGAGTGG
GTCTCATGGATTCAGGCTACGGTGGTGCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGGATGCATCCTCAGAGTGGTACTCTTTTTGACTA
CTGGGGTCAGGGAACCCTGGTCACCGTCTCGAGC

DOM7r-90
SEQ ID NO: 86
GAGGTGCAGCTGTTGGAGTCTGGGGGAGGCTTGGTACAGCCTGGGGG
GTCCCTGCGTCTCTCCTGTGCAGCCTCCGGATTCACCTTTGATGTTG
CGGATATGGATTGGGTCCGCCAGGCTCCAGGGAAGGGTCTAGAGTGG
GTCTCAGGGATTTCGTCGTCGGGTGGTTATACATACTACGCAGACTC
CGTGAAGGGCCGGTTCACCATCTCCCGCGACAATTCCAAGAACACGC
TGTATCTGCAAATGAACAGCCTGCGTGCCGAGGATACCGCGGTATAT
TACTGTGCGAAAATTTGGGTCAGGGTTTTGACTACTGGGGTCAGGG
AACCCTGGTCACCGTCTCGAGC

DOM7r-92
SEQ ID NO: 87
GAGGTGCAGCTGTTGGAGTCTGGGGGAGGCTTGGTACAGCCTGGGGG
GTCCCTGCGTCTCTCCTGTGCAGCCTCCGGATTCACCTTTGATACGA
GTAGTATGTTGTGGGTCCGCCAGGCTCCAGGGAAGGGTCTAGAGTGG
GTCTCAGTTATTCATCAGAGTGGTACGCCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATTTCCGTTTACTCATGGTAAGTTTGACTACTGGGG
TCAGGGAACCCTGGTCACCGTCTCGAGC

DOM7r-93
SEQ ID NO: 88
GAGGTGCAGCTGTTGGAGTCTGGGGGAGGCTTGGTACAGCCTGGGGG
GTCCCTGCGTCTCTCCTGTGCAGCCTCCGGATTCACCTTTAATAATT
ATACGATGGGGTGGGTCCGCCAGGCTCCAGGGAAGGGTCTAGAGTGG
GTCTCATTGATTCATACGAGTGGTACGGTGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATGGAGTTCGAGGGCGTTTGACTACTGGGGTCAGGG
AACCCTGGTCACCGTCTCGAGC

DOM7r-94
SEQ ID NO: 89
GAGGTGCAGCTGTTGGAGTCTGGGGGAGGCTTGGTACAGCCTGGGGG
GTCCCTGCGTCTCTCCTGTGCAGCCTCCGGATTCACCTTTGGGAATT
ATAGGATGACTTGGGTCCGCCAGGCTCCAGGGAAGGGTCTAGAGTGG
GTCTCAACTATTTCTCCTTTGGGTACGTATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGGGCGTTGGTCGATTTTTGACTACTGGGGTCAGGG
AACCCTGGTCACCGTCTCGAGC

DOM7r-95
SEQ ID NO: 90
GAGGTGCAGCTGTTGGAGTCTGGGGGAGGCTTGGTACAGCCTGGGGG
GTCCCTGCGTCTCTCCTGTGCAGCCTCCGGATTCACCTTTGGTAGTT
ATCCTATGGGTTGGGTCCGCCAGGCTCCAGGGAAGGGTCTGGAGTGG
GTCTCATGGATTCGTGGGAGGGGTCTTGCTACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATATTTTCATGGTAAGTTTGACTACTGGGGTCAGGG
AACCCTGGTCACCGTCTCGAGC

DOM7r-96
SEQ ID NO: 91
GAGGTGCAGCTGTTGGAGTCTGGGGGAGGCTTGGTACAGCCTGGGGG
GTCCCTGCGTCTCTCCTGTGCAGCCTCCGGATTCACCTTTAGTGCTT
ATGTGATGGGTTGGGTACGCCAGGCTCCAGGGAAGGGTCTAGAGTGG
GTCTCATCGATTCGGATGCGGGTTATCTGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAACGTACTCCTTTTTTTGACTACTGGGGTCAGGGAAC
CCTGGTCACCGTCTCGAGC

DOM7r-97
SEQ ID NO: 92
GAGGTGCAGCTGTTGGAGTCTGGGGGAGGCTTGGTACAGCCTGGGGG
GTCCCTGCGTCTCTCCTGTGCAGCCTCCGGATTCACCTTTGAGCATT
ATTCGATGGGTTGGGTCCGCCAGGCTCCAGGGAAGGGTCTAGAGTGG
GTCTCAGAGATTGATCCGGATGGTATTATGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGCGCCGGGGGTTCTTGAGATGTGGATTACGCATTT
TGACTACTGGGGTCAGGGAACCCTGGTCACCGTCTCGAGC

DOM7r-98
SEQ ID NO: 93
GAGGTGCAGCTGTTGGAGTCTGGGGGAGGCTTGGTACAGCCTGGGGG
GTCCCTGCGTCTCTCCTGTGCAGCCTCCGGATTCACCTTTCGTCATT
ATGTGATGGGTTGGGTCCGCCAGGCTCCAGGGAAGGGTCTAGAGTGG
GTCTCATATTTCTGCGCATGGTAATCGGACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAATCTTATAGCCTTGCTCTGACTCCTTTTGACTACTG
GGGTCAGGGAACCCTGGTCACCGTCTCGAGC

DOM7r-99
SEQ ID NO: 94
GAGGTGCAGCTGTTGGAGTCTGGGGGAGGCTTGGTACAGCCTGGGGG
GTCCCTGCGTCTCTCCTGTGCAGCCTCCGGATTCACCTTTACTGTGT
ATGAGATGAAGTGGGTCCGCCAGGCTCCAGGGAAGGGTCTAGAGTGG
GTCTCAGCGATTTCTGCTGGGGGTAAGTATACATACTACGCAGACTC
CGTGAAGGGCCGGTTCACCATCTCCCGCGACAATTCCAAGAACACGC
TGTATCTGCAAATGAACAGCCTGCGTGCCGAGGACACCGCGGTATAT
TACTGTGCGAAAGAGATTCGGCATCTTGATAATGCGGTTGAGTTTGA
CTACTGGGGTCAGGGAACCCTGGTCACCGTCTCGAGC

Amino Acid Sequences:

DOM7h-112
SEQ ID NO: 95
EVQLLESGGGLVQPGGSLRLSCAASGFTFGGYVMGWVRQAPGKGLEWVSAINRFGSSTYYADSVKGRFTI
SRDNSKNTLYLQMNSLRAEDTAVYYCAKGSLRHFDYWGQGTLVTVSS

DOM7h-98
SEQ ID NO: 96
EVQLLESGGGLVQPGGSLRLSCAASGFTFGNYAMAWVRQAPGKGLEWVSSIDMVGIKTYYADSVKGRFTI
SRDNSKNTLYLQMNSLRAEDTAVYYCAKGFRIFDYWGQGTLVTVSS

DOM7r-29
SEQ ID NO: 97
EVQLLESGGGLVQPGGSLRLSCAASGFTFKDYDMTWVRQAPGKGLEWVSMISSSGLWTYYADSVKGRFTI
SRDNSKNTLYLQMNSLRAEDTAVYYCAKGFRLFPRTFDYWGQGTLVTVSS

-continued

DOM7r-35
SEQ ID NO: 98
EVQLLESGGGLVQPGGSLRLSCAASGFTFSLYRMVWVRQAPGKGLEWVSMISQFGNQTYYADSVKGRFTI
SRDNSKNTLYLQMNSLRAEDTAVYYCAKVRSWDQTGGRRTFDYWGQGTLVTVSS

DOM7r-36
SEQ ID NO: 99
EVQLLESGGGLVQPGGSLRLSCAASGFTFNHYTMGWVRQAPGKGLEWVSLIHPSGTVTYYADSVKGRFTI
SRDNSKNTLYLQMNSLRAEDTAVYYCAKWSSRAFDYWGQGTLVTVSS

DOM7r-38
SEQ ID NO: 100
EVQLLESGGGLVQPGGSLRLSCAASGFTFDNNAMGWVRQAPGKGLEWVSTISANGNATYYADSVKGRFTI
SRDNSKDTLYLQMNSLRAEDTAVYYCAKGFRRFDYWGQGTLVTVSS

DOM7r31
SEQ ID NO: 101
EVQLLESGGGLVQPGGSLRLSCTASGFTFRHYRMGWVRQAPGKGLEWVSWIRPDGTFTYYADSVKGRFTI
SRDNSKNTLYLQMNSLRAEDTAVYYCAKSYMGDRFDYWGQGTLVTVSS

DOM7h-32
SEQ ID NO: 102
EVQLLESGGGLVQPGGSLRLSCAASGFTFGNYPMTWVRQAPGKGLEWVSTISYGGLATYYADSVKGRFTI
SRDNSKNTLYLQMNSLRAEDTAVYYCAKMAINGVRPRRFDYWGQGTLVTVSS

DOM7h-33
SEQ ID NO: 103
EVQLLESGGGLVQPGGSLRLSCAASGFTFMAYQMAWVRQAPGKGLEWVSTIHQTGFSTYYADSVKGRFTI
SRDNSKNTLYLQMNSLRAEDTAVYYCAKVRSMRPYKFDYWGQGTLVTVSS

DOM7h-34
SEQ ID NO: 104
EVQLLESGGGLVQPGGSLRLSCAASGFTFGDKAMGWVRQAPGKGLEWVSTISAPGNRTYYADSVKGRFTI
SRDNSKNTLYLQMNSLRAEDTAVYYCAKGFRNFDYWGQGTLVTVSS

DOM7h-83
SEQ ID NO: 105
EVQLLESGGGLVQPGGSLRLSCAASGFTFDGMRMGWVRQAPGKGLEWVSAIEVNGQHTYYADSVKGRFTI
SRDNSKNTLYLQMNSLRAEDTAVYYCAKMAHPQSGVAFDYWGQGTLVTVSS

DOM7h-84
SEQ ID NO: 106
EVQLLESGGGLVQPGGSLRLSCAASGFTFTPDAMAWVRQAPGKGLEWVSSIGVNGSPTYYADSVKGRFTI
SRDNSRNTLYLQMNSLRAEDTAVYYCAKMAHPQSGVAFDYWGQGTLVTVSS

DOM7h-85
SEQ ID NO: 107
EVQLLESGGGLVQPGGSLRLSCAASGFTFYQSDMSWVRQAPGKGLEWVSSISSQGRSTYYADSVKGRFTI
SRDNSKNTLYLQMNSLRAEDTAVYYCAKMAHPQSGVAFDYWGQGTLVTVSS

DOM7h-86
SEQ ID NO: 108
EVQLLESGGGLVQPGGSLRLSCTASGFTFAARDMSWVRQAPGKGLEWVSSISAQGAHTYYADSVKGRFTI
SRDDSKNTLYLQMNSLRAEDTAVYYCAKPRHPQGGVTFDYWGQGTLVTVSS

DOM7h-87
SEQ ID NO: 109
EVQLLESGGGLVQPGGSLRLSCAASGFTFDNGDMVWVRQAPGKGLEWVSGIAHNGRNTYYADSVKGRFTI
SRDNSKNTLYLQMNSLRAEDTAVYYCAKNLGQGFDYWGQGTLVTVSS

DOM7h-88
SEQ ID NO: 110
EVQLLESGGGLVQPGGSLRLTCAASGFTLNGTSMGWVRQAPGKDLEWVSSIMPVGSHTYYADSVKGRFTI
SRDNSKNTLYLQMNSLRAEDTAVYYCAKMAHPQSGVAFDYWGQGTLVTVSS

-continued

DOM7h-89
SEQ ID NO: 111
EVQLLESGGGLVQPGGSLRLSCAASGFTFDHAPMKWARQAPGKGLEWVSYIGSAGNMTYYADSVKGRFTI
SRDNSKNTLYLQMNSLRAEDTAVYYCAKDEGPFDYWGQGTLVTVSS

DOM7h-90
SEQ ID NO: 112
EVQLLESGGGLVQPGGSLRLSCTASGFTFDGMDMSWVRQAPGKGLEWVSSISTTGGTTYYADSVKGRFTI
SRDNSKNTLYLQMNSLRAEDTAVYYCAKPRHPQGGVTFDYWGQGTLVTVSS

DOM7h-91
SEQ ID NO: 113
EVQLLESGGGLVQPGGSLRLSCAASGFTFEAETMAWVRQAPGKGLEWVSTIHSEGSRTYYADSVKGRFTI
SRDNSKNTLYLQMNSLRAEDTAVYYCAKPRHPQGGVTFDYWGQGTLVTVSS

DOM7h-92
SEQ ID NO: 114
EVQLLESGGGLVQPGGSLRLSCAASGFTFSTGEMAWVRQAPGKGLEWVSSISSSGATTYYADSVKGRFTI
SRDNSKNTLYLQMNSLRAEDTAVYYCAKPRHPQGGVTFDYWGQGTLVTVSS

DOM7h-93
SEQ ID NO: 115
EVQLLESGGGLVQPGGSLRLSCAASGFTFPSADMVWVRQAPGKGLEWVSRISPEGNHTYYADSVKGRFTI
SRDNSKNTLYLQMNSLRAEDTAVYYCAERPPSDYVSFDYWGQGTLVTVSS

DOM7h-94
SEQ ID NO: 116
EVQLLESGGGLVQPGGSLRLSCAASGFTFANATMSWVRQAPGKGLEWVSDIDQVGHATYYADSVKGRFTI
SRDNSKNTLYLQMNSLRAEDTAVYYCAKYSWHPDLFDYWGQGTLVTVSS

DOM7h-95
SEQ ID NO: 117
EVRLLESGGGLVQPGGSLRLSCAASGFTFKDYGMNWVRQAPGKGLEWVSRISRNGTVTYYADSVKGRFTI
SRDNSKNTLYLQMNSLRAEDTAVYYCAKLAAPVRQKGMDFDYWGQGTLVTVSS

DOM7h-96
SEQ ID NO: 118
EVQLLESGGGLVQPGGSLRLSCAASGFTFEWYNMSWVRQAPGKDLEWVSSISHDGWNTYYADSVKGRFTI
SRDNSKNTLYLQMNSLRAEDTAVYYCAKGMIGFDYWGQGTLVTVSS

DOM7h-97
SEQ ID NO: 119
VQLLESGGGLVQPGGSLRLSCAASGFTFDIYTMHWVRQAPGKGLEWVSTIVPQGTPTYYADSVKGRFTIS
RDNSKNTLYLQMNSLRAEDTAVYYCAKSKRRFLKRFDYWGQGTLVTVSS

DOM7h-99
SEQ ID NO: 120
EVQLLESGGGLVQPGGSLRLSCAASGFTFARYDMQWVRQAPGKGLEWVSSIKSNGMKTYYADSVKGRFTI
SRDNSKNTLYLQMNSLRAEDTAVYYCAKASMWTFDYWGQGTLVTVSN

DOM7h-100
SEQ ID NO: 121
EVQLLESGGGLVQPGGSLRLSCAASGFTFMLYHMGWVRQAPGKGLEWVSAITGGGYPTYYADSVKGRFTI
SRDNSKNTLYLQMNSLRAEDTAVYYCAKLGLRGVLWRRRFDYWGQGTLVTVSS

DOM7h-101
SEQ ID NO: 122
EVQLLESGGGLVQPGGSLRLSCAASGFTFGAYSMMWVRQAPGKGLEWVSRISRNGTVTYYADSVKGRFTI
SRDNSKNTLYLQMNSLRAEDTAVYYCAKIRWNTAQVPVFDYWGQGTLVTVSS

DOM7h-102
SEQ ID NO: 123
EVQLLESGGGLVQPGGSLRLSCAASGFTFGPYWMAWVRQAPGKGLEWVSTITPSGRGTYYADSVKGRFTI
SRDNSKNTLYLQMNSLRAEDTAVYYCAKGRPRVGLWRSGFDYWGQGTLVTVSS

```
DOM7h-103
                                               SEQ ID NO: 124
EVQLLESGGGLVQPGGSLRLSCAASGFTFGQYAMQWVRQAPGKGLEWVSSINITGSTTYYADSVKGRFTI

SRDNSKNTLYLQMNSLRAEDTAVYYCAKGFRSFDYWGQGTLVTVSS

DOM7h-106
                                               SEQ ID NO: 125
VQLLESGGGLVQPGGSLRLSCAASGFTFAGYTMSWVRQAPGKGLEWVSTISGFGWTTYYADSVKGRFTIS

RDNSKNTLYLQMNSLRAEDTAVYYCAKRLGMRFDYWGQGTLVTVSS

DOM7h-109
                                               SEQ ID NO: 126
EVQLLESGGGLVQPGGSLRLSCAASGFTFGPYSMGWVRQAPGKGLEWVSFIHSDGRHTYYADSVKGRFTI

SRDNSKNTLYLQMNSLRAEDTAVYYCAKKTPYRFDYWGQGTLVTVSS

DOM7h-111
                                               SEQ ID NO: 127
EVQLLESGGGLVQPGGSLRLSCAASGFTFGQYAMQWVRQAPGKGLEWVSSINITGSTTYYADSVKGRFTI

SRDNSKNTLYLQMNSLRAEDTAVYYCAKGFRSFDYWGQGTLVTVSS

DOM7h-114
                                               SEQ ID NO: 128
EVQLLESGGGLVQPGGSLRLSCAASGFTFRRYAMSWVRQAPGKGLEWVSTISPYGPVTYYADSVKGRFTI

SRDNSKNTLYLQMNSLRAEDTAVYYCAKAYYGGFDYWGQGTLVTVSS

DOM7r-34
                                               SEQ ID NO: 129
EVQLLESGGGLVQPGGSLRLSCAASGFTFDAYAMGWVRQAPGKGLEWVSKIDSPGWRTYYADSVKGRFTI

SRDNSKNTLYLQMNSLRAEDTAVYYCAKSARMRSRHFDYWGQGTLVTVSS

DOM7r-37
                                               SEQ ID NO: 130
EVQLLESGGGLVQPGGSLRLSCAASGFTFKDYGMNWVRQAPGKGLEWVSRISRNGTVTYYADSVKGRFTI

SRDNSKNTLYLQMNSLRAEDTAVYYCAKIRWNTAQVPVFDYWGQGTLVTVSS

DOM7r-39
                                               SEQ ID NO: 131
EVQLLESGGGLVQPGGSLRLSCATSGFTFPSYTMGWVRQAPGKGLEWVSRISRTGNYTYYADSVKGRFTI

SRDNSKNTLYLQMNSLRAEDTAVYYCAKPMYNRGSSYFDYWGQGTLVTVSS

DOM7r-40
                                               SEQ ID NO: 132
EVQLLESGGGLVQPGGSLRLSCAASGFTFSQYQMSWVRQAPGKGLEWVSSISPTGIQTYYADSVKGRFTI

SRDNSKNTLYLQMNSLRAEDTAVYYCAKRLIGMPYVEDTFDYWGQGTLVTVSS

DOM7r-41
                                               SEQ ID NO: 133
EVQLLESGGGLVQPGGSLRLSCAASGFTFMEYEMEWVRQAPGKGLEWVSGITNSGSGTYYADSVKGRFTI

SRDNSKNTLYLQMNSLRAEDTAVYYCAIMQHPQATGGRVGFDYWGQGTLVTVSS

DOM7r-42
                                               SEQ ID NO: 134
EVQLLESGGGLVQPGGSLRLSCAASGFTFPRYTMKWVRQAPGKGLEWVSSIDRTGRKTYYADSVKGRFTI

SRDNSKNTLYLQMNSLRAEDTAVYYCAKESLVSFDYWGQGTLVTVSS

DOM7r-43
                                               SEQ ID NO: 135
EVQLLESGGGLVQPGGSLRLSCAASGFTFGGYTMPWVRQAPGKGLEWVSTISRDGNYTYYADSVKGRFTI

SRDNSKNTLYLQMNSLRAEDTAVYYCAKDIGMGFDYGGRGTLVTVSS

DOM7r-44
                                               SEQ ID NO: 136
EVQLLESGGGLVQPGGSLRLSCAASGFTFEIYAMHWVRQAPGKGLEWVSTISSGGKGTYYADSVKGRFTI

SRDNSKNTLYLQMNSLRAEDTAVYYCAKSRTMYFRVREAFDYWGQGTLVTVSS
```

-continued

DOM7r-45
SEQ ID NO: 137
EVQLLESGGGLVQPGGSLRLSCAASGFTFRAYRMMWVRQAPGKGLEWVSSIDPDGAVTYYADSVKGRFTI
SRDNSKNTLYLQMNSLRAEDTAVYYCAEHFDLAMPNPNAKFDYWGQGTLVTVSS

DOM7r-46
SEQ ID NO: 138
EVQLLESGGGLVQPGGSLRLSCAASGFTFSRYQMSWVRQAPGKGLEWVSSIKSNGSSTYYADSVKGRFTI
SRDNSKNTLYLQMNSLRAEDTAVYYCAKPSRQSFQYPSFDYWGQGTLVTVSS

DOM7r-47
SEQ ID NO: 139
EVQLLESGGGLVQPGGSLRLSCAASGFTFGRYKMGWVRQAPGKGLEWVSSISPTGSSTYYADSVKGRFTI
SRDNSKNTLYLQMNSLRAEDTAVYYCAKTGYVMVEHFDYWGQGTLVTVSS

DOM7r-48
SEQ ID NO: 140
EVQLLESGGGLVQPGGSLRLSCAASGFTFSDYPMKWVRQAPGKGLEWVSTINSSGTITYYADSVKGRFTI
SRDNSKNTLYLQMNSLRAEDTAVYYCAKPLLPFDYWGQGTLVTVSS

DOM7r-49
SEQ ID NO: 141
EVQLLESGGGLVQPGGSLRLSCAASGFTFARYRMCWVRQAPGKGLEWVSCIRDPGFPTYYADSVKGRFTI
SRDNSKNTLYLQMNSLRAEDTAVYYCAKCSPSSTQCTGLFDYWGQGTLVTVSS

DOM7r-50
SEQ ID NO: 142
VQLLESGGGLVQPGGSLRLSCAASGFTFRFYGMAWVRQAPGKGLEWVSLIDPPGGATYYADSVKGRFTIS
RDNSKNTLYLQMNSLRAEDTAVYYCAKMERRHLKSGHKGFDYWGQGTLVTVSS

DOM7r-51
SEQ ID NO: 143
EVQLLESGGGLVQPGGSLRLSCAASGFTFTEYDMMWVRQAPGKGLEWVSSISHRGEKTYYADSVKGRFTI
SRDNSKNTLYLQMNSLRAEDTAVYYCAKDKRYRGSQHYFDYWGQGTLVTVSS

DOM7r-52
SEQ ID NO: 144
VQLLESGGGLVQPGGSLRLSCAASGFTFRSYDMGWARQAPGKGLEWVSTIGSNGANTYYADSVKGRFTIS
RDNSKNTLYLQMNSLRAEDTAVYYCAKLMGMFDYWGQGTLVTVSS

DOM7r-53
SEQ ID NO: 145
EVQLLESGGGLVQPGGSLRLSCAASGFTFERYSMRWVRQAPGKGLEWVSTIGSTGKWTYYADSVKGRFTI
SRDNSKNTLYLQMNSLRAEDTAVYYCAKGRGLVSFDYWGQGTLVTVSS

DOM7r-54
SEQ ID NO: 146
EVQLLESGGGLVQPGGSLRLSCAASGFTFRRYSMSWVRQAPGKGLEWVSSIDRSGRMTYYADSVKGRFTI
SRDNSKNTLYLQMNSLRAEDTAVYYCAKSRLSSTGSEGHNFDYWGQGTLVTVSS

DOM7r-55
SEQ ID NO: 147
VQLLESGGGLVQPGGSLRLSCAASGFTFKWYPMKWVRQAPGKGLEWVSTIAYDGVQTYYADSVKGRFTIS
RDNSKNTLYLQMNSLRAEDTAVYYCAKLGPTSRVFAATDFDYWGQGTLVTVSS

DOM7r-56
SEQ ID NO: 148
EVQLLESGGGLVQPGGSLRLSCAASGFTFPNYAMKWGRQAPGKGLEWVSTIDTSGSTTYYADSVKGRFTI
SRDNSKNTLYLQMNSLRAEDTAVYYCAKLTHPMAPRPAFDYWGQGTLVTVSS

DOM7r-57
SEQ ID NO: 149
EVQLLESGGGLVQPGGSLRLSCAASGFTFDLTEMEWVRQAPGKGLEWVSSIGPWGTPTYYADSVKGRFTI
SRDNSKNTLYLQMNSLRAEDTAVYYCAKISHPQAMYHTFDYWGQGTLVTVSS

-continued

DOM7r-58
SEQ ID NO: 150
EVQLLESGGGLVQPGGSLRLSCAASGFTFAHQDMTWVRQAPGKGLEWVSDIDHSGSYTYYADSVKGRFTI
SRDNSKNTLYLQMNSLRAEDTAVYYCAKWWHPQGGTFDYWGQGTLVTVSS

DOM7r-59
SEQ ID NO: 151
EVQLLESGGGLVQPGGSLRLSCAASGFTFGSKDMSWVRQAPGKGLEWVSTIGANGKATYYADSVKGRFTI
SRDNSKNTLYLQMNSLRAEDTAVYYCAEAGHPQAPSFKSFDYWGQGTLVTVSS

DOM7r-60
SEQ ID NO: 152
EVQLLESGGGLVQPGGSLRLSCAASGFTFLNAEMSWVRQAPGKGLEWVSTIDRDGANTYYADSVKGRFTI
SRDNSKNTLYLQMNSLRAEDTAVYYCAKLPPPMSPKKFDYWGQGTLVTVSS

DOM7r-61
SEQ ID NO: 153
EVQLLESGGGLVQPGGSLRLSCAASGFTFEREGMMWVRQAPGKGLEWVSTIDRMGRYTYYADSVKGRFTI
SRDNSKNTLYLQMNSLRAEDTAVYYCAKRDSHPMGFDYRGQGTLVTVSS

DOM7r-62
SEQ ID NO: 154
EVQLLESGGGLVQPGGSLRLSCAASGFTFENEKMSWVRQAPGKGLEWVSSIGPTGSGTYYADSVKGRFTI
SRDNSKNTLYLQMNSLRAEDTAVYYCAKTPHPQVSSFDYWGQGTLVTVSS

DOM7r-63
SEQ ID NO: 155
EVQLLESGGGLVQPGGSLRLSCAASGFTFEIDHMGWVRQAPGKGLEWVSEIAPSGDRTYYADSVKGRFTI
SRDNSKNTLYLQMNSLRAEDTAVYYCAKVICQNQCLFDYWGQGTLVTVSS

DOM7r-64
SEQ ID NO: 156
EVQLLESGGGLVQPGGSLRLSCAASGFTFRDSEMSWVRQAPGKGLEWVSFITSDGRDTYYADSVKGRFTI
SRDNSKNTLYLQMNSLRAEDTAVYYCAKPSLPHVTAFDYWGQGTLVTVSS

DOM7r-65
SEQ ID NO: 157
EVQLLESGGGLVQPGGSLRLSCAASGFTFEDETMSWARQAPGKGLEWVSSIGDAGMPTYYADSVKGRFTI
SRDNSKNTLYLQMNSLRAEDTAVYYCAKGEPIYVHTTHFDYWGQGTLVTVSS

DOM7r-66
SEQ ID NO: 158
EVQLLESGGGLVQPGGSLRLSCAASGFTFPHGKMGWVRQAPGKGLEWVSWIAGSGDMTYYADSVKGRFTI
SRDNSKNTLYLQMNSLRAEDTAVYYCAKLGHPQRGFDYWGQGTLVTVSS

DOM7r-67
SEQ ID NO: 159
EVQLLESGGGLVQPGGSLRLSCAASGFTFGTSDMSWVRQAPGKGLEWVSTIDSGGSFTYYADSVKGRFTI
SRDNSKNTLYLQMNSLRAEDTAVYYCAKPRHPQGGVTFDYWGQGTLVTVSS

DOM7r-68
SEQ ID NO: 160
EVQLLESGGGLVQPGGSLRLSCAASGFTFEHVPMAWVRQAPGKGLEWVSRISEQGSNTYYADSVKGRFTI
SRDNSKNTLYLQMNSLRAEDTAVYYCAKVQHPMSPHEFDYWGQGTLVTVSS

DOM7r-69
SEQ ID NO: 161
EVQLLESGGGLVQPGGSLRLSCAASGFTFEQGMMSWVRQAPGKGLEWVSSINPGGQFTYYADSVKGRFTI
SRDNSRNTLYLQMNSLRAEDTAVYYCAEDLGPGFDYWGQGTLVTVSS

DOM7r-70
SEQ ID NO: 162
EVQLLESGGGLVQPGGSLRLSCAASGFTFERWPMSWVRQAPGKGLEWVSTIDRSGNTTYYADSVKGRFTI
SRDNSKNTLYLQMNSLRAEDTAVYYCAKVLHPQAGSAFDYWGQGTLVTVSS

-continued

DOM7r-71
SEQ ID NO: 163
EVQLLESGGGSVQPGGSLRLSCAASGFTFGGSDMGWVRQAPGKGLEWVSYIDNQGYNTYYADSVKGRFTI
SRDNSKNTLYLQMNSLRAEDTAVYYCAKYKLLGPSTEFDYWGQGTLVTVSS

DOM7r-72
SEQ ID NO: 164
EVQLLESGGGLVQPGGSLRLSCAASGFTFSSDVMSWVRQAPGKGLEWVSSITRSGMQTYYADSVKGRFTI
SRDNSKNTLYLQMNSLRAEDTAVYYCAKYAHPQSAVEFDYWGQGTLVTVSS

DOM7r-73
SEQ ID NO: 165
EVQLLESGGGLVQPGGSLRLSCAASGFTFRNEPMSWVRQAPVKGLEWVSTISPDGSGTYYADSVKGRFTI
SRDNSKNTLYLQMNSLRAEDTAVYYCAKHGHPQGARFDYWGQGTLVTVSS

DOM7r-74
SEQ ID NO: 166
EVQLLESGGGLVQPGGSLRLSCAASGFTFLNSEMSWVRQAPGKGLEWVSTIGYAGTPTYYADSVKGRFTI
SRDNSKNTLYLQMNSLRAEDTAVYYCAKPRHPQGGVTFDYWGQGTLVTVSS

DOM7r-75
SEQ ID NO: 167
EVQLLESGGGLVQPGGSLRLSCAASGFTFARGPMSWVRQAPGKGLEWVSTITNDGTSTYYADSVKGRFTI
SRDNSKNTLYLQMNSLRAEDTAVYYCAEPPHSGRPMFDYWGQGTLVTVSS

DOM7r-76
SEQ ID NO: 168
EVQLLESGGGLVQPGGSLRLSCAASGFTFQRTAMSWVRQAPGKGLEWVSSIEASGRYTYYADSVKGRFTI
SRDNSKNTLYLQMNSLRAEDTAVYYCAKQSHPQNGRFDYWGQGTLVTVSS

DOM7r-77
SEQ ID NO: 169
EVQLLESGGGLVQPGGSLRLSCAASGFTFDASEMAWVRQAPGKGLEWVSSITVYGDRTYYADSVKGRFTI
SRDNSKNTLYLQMNSLRAEDTAVYYCAKPRHPQGGVTFDYWGQGTLVTVSS

DOM7r-78
SEQ ID NO: 170
EVQLLESGGGLVQPGGSLRLSCAASGFTFDDSHMAWVRQAPGKGLEWVSRISREGKATYYADSVKGRFTI
SRDNSKNTLYLQMNSLRAEDTAVYYCAAPNDQSAAFDYWGQGTLVTVSS

DOM7r-79
SEQ ID NO: 171
EVQLLESGGGLVQPGGSLRLSCAASGFTFDMSEMSWVRQAPGKGLEWVSAITSDGSSTYYADSVKGRFTI
SRDNSKNTLYLQMNSLRAEDTAVYYCAKPSLPHVTAFDYWGQGTLVTVSS

DOM7r-80
SEQ ID NO: 172
EVQLLESGGGLVQPGGSLRLSCAASGFTFERSTMHWVRQAPGKGLEWVSEIDALGTDTYYADSVKGRFTI
SRDNSKNTLYLQMNSLRAEDTAVYYCAKSSDHPQNSFDYWGQGTLVTVSS

DOM7r-81
SEQ ID NO: 173
EVQLLESGGGLVQPGGSLRLSCAASGFTFEPREMYWARQAPGKGLEWVARIGWDGHTTYYADSVKGRFTI
SRDNSKNTLYLQMNSLRAEDTAVYYCAKQLGQFDYWGQGTLVTVSS

DOM7r-82
SEQ ID NO: 174
EVQLLESGGGLVQPGGSLRLSCAASGFTFDAYSMMWVRQAPGKGLEWVSTIGRWGEITYYADSVKGRFTI
SRDNSKNTLYLQMNSLRAEDTAVYYCAKRRYIGPYMLSGRFDYWGQGTLVTVSS

DOM7r-83
SEQ ID NO: 175
EVQLLESGGGLVQPGGSLRLSCAASGFTFMRYPMVWVRQAPGRGLEWVSSISPAGYGTYYADSVKGRFTI
SRDNSKNTLYLQMNSLRAEDTAVYYCAKGHEISRFSRWSSFDYWGQGTLVTVSS

```
DOM7r-84
                                                        SEQ ID NO: 176
EVQLLESGGGLVQPGGSLRLSCAASGFTFRKYRMSWVRQAPGKGLEWVSSIARNGRSTYYADSVKGRFTI

SRDNSKNTLYLQMNSLRAEDTAVYYCAKTTSGFDYWGQGTLVTVSS

DOM7r-85
                                                        SEQ ID NO: 177
EVQLLESGGGLVQPGGSLRLSCAASGFTFNKKEMGWVRQAPGKGLEWVSSIDVSGNVTYYADSVKGRFTI

SRDNSKNTLYLQMNSLRAEDTAVYYCAKMAHPQSGVAFDYWGQGTLVTVSS

DOM7r-88
                                                        SEQ ID NO: 178
EVQLLESGGGLVQPGGSLRLSCAASGFTFRMYDMAWVRQAPGKGLKWVSTILSSGKGTYYADSVKGRFTI

SRDNSKNTLYLQMNSLRAEDTAVYYCAKLAHPQKGSIFDYRGQGTLVTVSS

DOM7r-89
                                                        SEQ ID NO: 179
EVQLLESGGGLVQPGGSLRLSCAASGFTFHQGPMGWVRQAPGKGLEWVSWIQATGGATYYADSVKGRFTI

SRDNSKNTLYLQMNSLRAEDTAVYYCAKGMHPQSGTLFDYWGQGTLVTVSS

DOM7r-90
                                                        SEQ ID NO: 180
EVQLLESGGGLVQPGGSLRLSCAASGFTFDVADMDWVRQAPGKGLEWVSGISSSGGYTYYADSVKGRFTI

SRDNSKNTLYLQMNSLRAEDTAVYYCAKNLGQGFDYWGQGTLVTVSS

DOM7r-92
                                                        SEQ ID NO: 181
EVQLLESGGGLVQPGGSLRLSCAASGFTFDTSSMLWVRQAPGKGLEWVSVIHQSGTPTYYADSVKGRFTI

SRDNSKNTLYLQMNSLRAEDTAVYYCAKFPFTHGKFDYWGQGTLVTVSS

DOM7r-93
                                                        SEQ ID NO: 182
EVQLLESGGGLVQPGGSLRLSCAASGFTFNNYTMGWVRQAPGKGLEWVSLIHTSGTVTYYADSVKGRFTI

SRDNSKNTLYLQMNSLRAEDTAVYYCAKWSSRAFDYWGQGTLVTVSS

DOM7r-94
                                                        SEQ ID NO: 183
EVQLLESGGGLVQPGGSLRLSCAASGFTFGNYRMTWVRQAPGKGLEWVSTISPLGTYTYYADSVKGRFTI

SRDNSKNTLYLQMNSLRAEDTAVYYCAKGRWSIFDYWGQGTLVTVSS

DOM7r-95
                                                        SEQ ID NO: 184
EVQLLESGGGLVQPGGSLRLSCAASGFTFGSYPMGWVRQAPGKGLEWVSWIRGRGLATYYADSVKGRFTI

SRDNSKNTLYLQMNSLRAEDTAVYYCAKYFHGKFDYWGQGTLVTVSS

DOM7r-96
                                                        SEQ ID NO: 185
EVQLLESGGGLVQPGGSLRLSCAASGFTFSAYVMGWVRQAPGKGLEWVSSIRMPGYLTYYADSVKGRFTI

SRDNSKNTLYLQMNSLRAEDTAVYYCAKRTPFFDYWGQGTLVTVSS

DOM7r-97
                                                        SEQ ID NO: 186
EVQLLESGGGLVQPGGSLRLSCAASGFTFEHYSMGWVRQAPGKGLEWVSEIDPDGIMTYYADSVKGRFTI

SRDNSKNTLYLQMNSLRAEDTAVYYCAKAPGVLEMWITHFDYWGQGTLVTVSS

DOM7r-98
                                                        SEQ ID NO: 187
EVQLLESGGGLVQPGGSLRLSCAASGFTFRHYVMGWVRQAPGKGLEWVSAISAHGNRTYYADSVKGRFTI

SRDNSKNTLYLQMNSLRAEDTAVYYCAKSYSLALTPFDYWGQGTLVTVSS

DOM7r-99
                                                        SEQ ID NO: 188
EVQLLESGGGLVQPGGSLRLSCAASGFTFTVYEMKWVRQAPGKGLEWVSAISAGGKYTYYADSVKGRFTI

SRDNSKNTLYLQMNSLRAEDTAVYYCAKEIRHLDNAVEFDYWGQGTLVTVSS
```

EXEMPLIFICATION

Example 1

Biophysical Characterisation:

The routine bacterial expression level in 2.5 L shake flasks was determined following culture in Onex media at 30° C. for 48 hrs at 250 rpm. The biophysical characteristics were determined by SEC MALLS and DSC.

SEC MALLS (size exclusion chromatography with multi-angle-LASER-light-scattering) is a non-invasive technique is indicative of varying degrees of self-association or dimer formation (i.e 16 kDa predominately monomeric under the conditions tested whereas 22 kDa indicates a strong propensity to dimerise under MALLS conditions).

DSC results: The concentration of protein in a DSC experiment is much higher at 1 mg/mL in the actual reaction cell compared to MALLS. This higher concentration could explain in part the presence of two appTms for some AlbudAbs as seen in table 1; the first Tm constitutes the dissociation of the dimeric complex, whereas the second Tm represents the unfolding of the actual AlbudAb protein.

TABLE 1

| * | x-reactivity | MALLS | DSC [° C.] | | Expression (*E. coli*) mg/L | Binding to D1/2/3 of HSA |
|---|---|---|---|---|---|---|
| Clone Name | (4AGs) | [kDa] | appTm1 | appTm2 | in shake flasks | SPR |
| DOM7h-112 | no human; yes other 3 antigens | 16 | 62 | 66 | 46.6 | No binding |
| DOM7H-98 | yes | 14.7 | 65 | | 28.3 | D2 |
| DOM7r-29 | yes | 16.9 | 62.5 | | 21 | D2 |
| DOM7r-35 | yes | 21.8 | 58.7 | 61.8 | 33.5 | D2 |
| DOM7r-36 | yes | 98/45/16 | 67.4 | 69.9 | 31.5 | D2 |
| DOM7r-38 | yes | 14.8 | 61.3 | 64.5 | 61.5 | D2 |
| DOM7r-31 | yes | 15 | 67.9 | 74.5 | 25 | D2 |

* precise in-solution affinities of the leads will be determine by ITC, equilibrium dialysis or fluorescence polarisation for the characterizing of macromolecules in solution. Briefly, proteins (at concentration of 1 mg/mL in buffer Dulbecco's PBS) are separated according to their hydrodynamic properties by size exclusion chromatography (column: TSK3000; S200). Following separation, the propensity of the protein to scatter light is measured using a multi-angle-LASER-light-scattering (MALLS) detector. The intensity of the scattered light while protein passes through the detector is measured as a function of angle. This measurement taken together with the protein concentration determined using the refractive index (RI) detector allows calculation of the molar mass using appropriate equations (integral part of the analysis software Astra v.5.3.4.12). The highest concentration at the mid-point of the eluting peak is about 8-10 uM and this consequently is the concentration at which MALLS determines the in-solution state of the protein.

DSC (Differential Scanning calorimetry): briefly, the protein is heated at a constant rate of 180 degrees C./hrs (at 1 mg/mL in PBS) and a detectable heat change associated with thermal denaturation measured. The transition midpoint ($_{app}T_m$) is determined, which is described as the temperature where 50% of the protein is in its native conformation and the other 50% is denatured. Here, DSC determined the apparent transition midpoint (app Tm) as most of the proteins examined do not fully refold. The higher the Tm, the more stable the molecule. The software package used was Origin$^R$ v7.0383.

Characteristics of the VH dAbs are summarised in Table 1 below. Cross-reactivity of the AlbudAbs™ (ie, anti-serum albumin dAbs) was determined against human, Cynomolgus monkey (cyno), rat and mouse serum albumin ("4AGs" in the table) using surface plasmon resonance (SPR). In this case, Biacore™ was used. The epitope mapping to domain 1, 2 and/or 3 (D1,2,3) of human serum albumin (HSA) was performed using SPR and purified individual domains of HSA (in-house) covalently coupled to a CM5 chip (amine coupling). The expression was in 2.5 L baffled glass flasks in a volume of 500 mL in OverNight Express™ at 30 C, 250 rpm.

MALLS results: A single VH AlbudAb is 14 kDa in size. Any value between 14 and 28 kDa as determined by MALLS Apart from DOM7h-112, all above AlbudAbs leads are fully cross-reactive between the four species of serum albumin. All identified AlbudAbs bind Domain2 of HSA and express reasonably well in shake flasks under non-optimised conditions. 5 out of 7 AlbudAbs are monomeric as determined by MALLS, whereas DOM7r-35 shows a significant propensity to dimerise under the MALLS conditions. Monomeric state is advantageous because it avoids dimerisation and the risk of products that may cross-link targets such as cell-surface receptors.

DOM7r-36 shows some degree of aggregate formation (less than 10% when quantified on MALLS). For 5 out of 7 AlbudAbs, 2 appTms can be determined. This is due to the higher experimental concentration in DSC experiments and slightly different in-solution state of the dAb at this elevated concentration (for details, see explanation also above).

Example 2

Determination of Serum Half Life in Rat

AlbudAbs were cloned into the pDOM5 vector. The pDOM5 vector is a pUC119-based expression vector where protein expression is driven by the LacZ promoter. A GAS1 leader sequence (see WO 2005/093074) ensures secretion of isolated, soluble dAbs into the periplasm and culture supernatant of *E. coli*. dAbs are cloned SalI/NotI in this vector, which appends a myc tag at the C-terminus of the dAb. For each AlbudAb, 20-50 mg quantities were expressed in *E. coli* and purified from bacterial culture supernatant using protein A affinity resin and eluted with 100 mM glycine pH2. The proteins were concentrated to greater than 1 mg/ml, buffer exchanged into PBS and endotoxin depleted using Q spin columns (Vivascience). For Rat pharmacokinetic (PK) analysis, AlbudAbs were dosed as single i.v injections at 2.5 mg/kg using 3 rats per compound. Serum samples were taken at 0.16, 1, 4, 12, 24, 48, 72, 96, 120, 168 hrs. Analysis of serum levels was by anti-myc capture followed by anti-VH detection ELISA as per the method described below.

Results are shown in table 2. All tested AlbudAbs show a serum-half life extending ability (negative control HEL4 dAb with T½ of 20 mins in rat) to varying degrees; this trend can also be seen in the calculated AUC being the highest value for the longest t½. The longest serum half-life with 34.5 hrs approximates the serum half-life of rat serum albumin.

The specific affinities of the AlbudAbs to RSA will need to be determined.

TABLE 2

| VH dAb | T ½* [hr] | AUC 0-inf [hr*ug/mL] |
|---|---|---|
| DOM7h-98 | 13.5 | 577.5 |
| DOM7r-29 | 21.9 | 697.6 |
| DOM7r-35 | 34.4 | 1249.6 |
| DOM7r-36 | 26.5 | 910.8 |
| DOM7r-38 | 8.8 | 203.4 |
| DOM7r-31 | 11 | 239 |

*The serum half-life of rat serum albumin is 35 hrs.
T ½ is a measure of the circulation time of the molecule in the subjects.
AUC = area under the curve, which is a PK profile parameter Anti-myc ELISA Method Using MSD The AlbudAb concentration in serum was measured by anti-myc ELISA. Briefly, goat anti-myc polyclonal antibody (1:500; Abcam, catalogue number ab9132) was coated overnight onto Nunc 96-well Maxisorp plates and blocked with 5% BSA/PBS+1% TWEEN™. Serum samples were added at a range of dilutions alongside a standard at known concentrations. Bound myc-tagged AlbudAb was then detected using a rabbit polyclonal anti-VH directly labelled with the MSD sulfo-tag. Each dAb was diluted in assay buffer containing 10% control rat serum (1:1000; in-house reagent) (method DM222). MSD (MesoScaleDiscovery; MesoScale.com) utilizes electrochemiluminescence detection of the sulfo-tag after electrochemical stimulus.

From the raw ELISA data, the concentration of unknown samples was established by interpolation against the standard curve taking into account dilution factors. The mean concentration result from each time point was determined from replicate values and entered into WinNonLin analysis package (eg version 5.1 (available from Pharsight Corp., Mountain View, Calif. 94040, USA). The data was fitted using a non-compartmental model, where PK parameters were estimated by the software to give terminal half-lives. Dosing information and time points were selected to reflect the terminal phase of each PK profile.

Example 3

Affinity Maturation of Naïve VH AlbudAbs™

12 VH AlbudAb leads isolated from naïve selection were taken forward for affinity maturation. Individual error prone libraries (EP) of DOM7r-36, DOM7r-35, DOM7r-31, DOM7h-98, DOM7h-112, DOM7r-38 and DOM7r-29 were made, whereas the following parental clones were pooled and combined in a single EP library and screened together: DOM7r-83, DOM7r-85, DOM7r-92, DOM7r-94 and DOM7r-95. All libraries were greater than $2 \times 10^9$ CFU/mL.

Selections were performed in 4 rounds on soluble antigen (biotin-HSA; biotin-RSA; blocking with 2% Marvel) by cross over-selection with decreasing concentration of antigen: Round1 at 1 µM (HSA or RSA), Round 2 at 1 uM (RSA or HSA), followed by 2 further rounds of selection at 100 nM and 10 nM, respectively, with the same antigen as in Round2. Ca. 3000 samples from both, R3 and R4 outputs were screened by supernatant BIAcore and clones ranked according to their off-rate only. Eight-point dilution kinetic affinity measurements were performed on improved clones (data below).

TABLE 3

| Improved clone | From round |
|---|---|
| DOM7r-31-14 | R4 |
| DOM7r-201 | R3 |
| DOM7r-36-2 | R4 |
| DOM7r-36-8 | R4 |
| DOM7r-92-4 | R4 |
| DOM7h-98-4 | R3 |

TABLE 4

| | Kinetic data: | | | |
|---|---|---|---|---|
| | RSA KD (M) | HSA KD (M) | CSA KD (M) | MSA KD (M) |
| DOM7r-201 | 2.4E−07 | 6.0E−08 | 5.8E−08 | 2.8E−07 |
| DOM7r-36-2 | 1.9E−07 | 1.5E−07 | 1.8E−07 | 5.2E−07 |
| DOM7r-36-8 | 2.1E−07 | 6.7E−08 | 9.2E−08 | 5.2E−07 |
| DOM7r-92-4 | 2.6E−07 | 1.3E−07 | 9.8E−08 | 1.1E−07 |
| DOM7h-98-4 | 5.8E−07 | 2.0E−06 | 3.6E−06 | 8.1E−07 |
| DOM7r-31-14 | 4.6E−08 | 5.8E−08 | 3.1E−05 | 6.0E−09 |

TABLE 5

```
                       Sequence alignment:
              5           15          25          35          45          55
   A   EVQLLESGGG  LVQPGGSLRL  SCAASGFTFS  SYAMSWVRQA  PGKGLEWVSA  ISGSGGSTYY
   B   EVQLLESGGG  LVQPGGSLRL  SCAASGFTFN  HYTMGWVRQA  PGKGLEWVSL  IHPSGTVIYY
   C   EVQLLESGGG  LVQPGGSLRL  SCAASGFTFN  HYTMGWVRQA  PGKGREWVSL  IHPSGTVTYY
   D   EVQLLESGGG  LVQPGGSLRL  SCAASGFTFN  HYTMGWVRQA  PGKGLEWVSL  IHPSGTVIYY
   E   EVQLLESGGG  LVQPGGSLRL  SCAASGFTFD  TSSMLWVRQA  PGKGLEWVSV  IHQSGTPTYY
   F   EVQLLESGGG  LVQPGGSLRL  SCAASGFTFG  NYAMAWVRQA  PGKGLEWVSS  IDMVGIKTYY
   G   EVQLLESGGG  LVQPGGSLRL  SCTASGFTFR  HYRMGWVRQA  PGKGLEWVSW  IRPDGTFTYY 65          75          85          95          105         115
   A   ADSVKGRFTI  SRDNSKNTLY  LQMNSLRAED  TAVYYCAKSY  GA~~~FDYWG  QGTLVTVSS
   B   ADSVKGRFTI  SRDNSKNTLY  LQMNSLRAED  TAVYYCAKWS  SRA~~~FDYWG QGTLVTVSS
```

TABLE 5-continued

Sequence alignment:

```
C   ADSVKGRFTI SRDNSKNTLY LQMNSLRAED TAVYYCAKWS SRA~~FDYWG QGTLVTVSS
D   ADSVKGRFTI SRDNSKNTLY LQMNSLRAED TAVYYCARWS SRA~~FDYWG QGTLVTVSS
E   ADSVKGRFTI SRDNSKNTLY LQMNSLRAED TAVYYCAKFP STHGKFDYWG QGTLVTVSS
F   ADSVKGRFTN SRDNSKNTLY LQMNSLRAED TAVYYCARGF RI~~~FDYWG QGTLVTVSS
G   ADSVKGRFTI SRDNSKNTLY LQMNSLRAED TAVYYCAKSY MADR~FDYWG QGTLVTVSS
```

A = VH dummy
B = DOM7r-201
C = DOM7r-36-2
D = DOM7r-36-8
E = DOM7r-92-4
F = DOM7h-98-4
G = DOM7r-31-1

The CDRs are underlined; sequences are shown N- to C-terminus; "~" denote gaps introduced for alignment Nucleotide Sequences DOM7r-201

SEQ ID NO: 189

GAGGTGCAACTGTTGGAGTCTGGGGGAGGCTTGGTACAGCCTGGGGGTC
CCTGCGTCTCTCCTGTGCAGCCTCCGGATTCACCTTTAATCATTATACGA
TGGGTTGGGTCCGCCAGGCTCCAGGGAAGGGTCTAGAGTGGGTCTCATTG
ATTCATCCGAGTGGTACGGTGATATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGAGT
TCGAGGGCATTTGACTACTGGGGTCAGGGAACCCTGGTCACCGTCTCTAG
C

DOM7r-36-2

SEQ ID NO: 190

GAGGTGCAGCTGTTGGAGTCTGGGGGAGGCTTGGTACAGCCTGGGGGTC
CCTGCGTCTCTCCTGTGCAGCCTCCGGATTCACCTTTAATCATTATACGA
TGGGGTGGGTCCGCCAGGCTCCAGGGAAGGGTCGAGAGTGGGTCTCATTG
ATTCATCCGAGTGGTACGGTGACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATGGAGT
TCGAGGGCGTTTGACTACTGGGGTCAGGGAACCCTGGTCACCGTCTCGAG
C

DOM7r-36-8

SEQ ID NO: 191

GAGGTGCAACTGTTGGAGTCTGGGGGAGGCTTGGTACAGCCTGGGGGTC
CCTGCGTCTCTCCTGTGCAGCCTCCGGATTCACCTTTAATCATTATACGA
TGGGTTGGGTCCGCCAGGCTCCAGGGAAGGGTCTAGAGTGGGTCTCATTG
ATTCATCCGAGTGGTACGGTGATATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAGATGGAGT
TCGAGGGCGTTTGACTACTGGGGTCAGGGGACCCTGGTCACCGTCTCGAG

DOM7r-92-4

SEQ ID NO: 192

GAGGTGCAGCTGTTGGAGTCTGGGGGAGGCTTGGTACAGCCTGGGGGTC
CCTGCGTCTCTCCTGTGCAGCCTCCGGATTCACCTTTGATACGAGTAGTA
TGTTGTGGGTCCGCCAGGCTCCAGGGAAGGGTCTAGAGTGGGTCTCAGTT
ATTCATCAGAGTGGTACGCCTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATTTCCG
TCTACTCATGGTAAGTTTGACTACTGGGGTCAGGGAACCCTGGTCACCGT
CTCGAGC

DOM7h-98-4

SEQ ID NO: 193

GAGGTGCAGCTGTTGGAGTCTGGGGGAGGCTTGGTACAGCCTGGGGGTC
CCTGCGTCTCTCCTGTGCAGCCTCCGGATTCACCTTTGGTAATTATGCGA
TGGCGTGGGTCCGCCAGGCTCCAGGGAAGGGTCTAGAGTGGGTCTCATCG
ATTGATATGGTTGGTATTAAGACATACTACGCAGACTCCGTGAAGGGCCG
GTTCACCAATTCCCGCGACAATTCCAAGAACACGCTGTATCTGCAAATGA
ACAGCCTGCGTGCCGAGGACACCGCGGTATATTACTGTGCGAGAGGTTTT
CGTATTTTTGACTACTGGGGTCAGGGAACCCTGGTCACCGTCTCGAGC

DOM7r-31-14

SEQ ID NO: 194

GAGGTGCAGCTGTTGGAGTCTGGGGGAGGCTTGGTACAGCCTGGGGGTC
CCTGCGTCTCTCCTGTACAGCCTCCGGATTCACCTTTAGGCATTATCGTA
TGGGTTGGGTCCGCCAGGCTCCAGGGAAGGGTCTAGAGTGGGTCTCATGG
ATTCGTCCGGATGGTACGTTTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAATCTTAT
ATGGCTGATAGGTTTGACTACTGGGGTCAGGGAACCCTGGTCACCGTCTC
GAGC

Amino Acid Sequences

DOM7r-201

SEQ ID NO: 195

EVQLLESGGGLVQPGGSLRLSCAASGFTFNHYTMGWVRQAPGKGLEWVSL

IHPSGTVIYYADSVKGRFTISRDNSKNTLYLQMNSLRAEDTAVYYCAKWS

SRAFDYWGQGTLVTVSS

DOM7r-36-2

SEQ ID NO: 196

EVQLLESGGGLVQPGGSLRLSCAASGFTFNHYTMGWVRQAPGKGREWVSL

IHPSGTVTYYADSVKGRFTISRDNSKNTLYLQMNSLRAEDTAVYYCAKWS

SRAFDYWGQGTLVTVSS

DOM7r-36-8

SEQ ID NO: 197

EVQLLESGGGLVQPGGSLRLSCAASGFTFNHYTMGWVRQAPGKGLEWVSL

IHPSGTVIYYADSVKGRFTISRDNSKNTLYLQMNSLRAEDTAVYYCARWS

SRAFDYWGQGTLVTVSS

DOM7r-92-4

SEQ ID NO: 198

EVQLLESGGGLVQPGGSLRLSCAASGFTFDTSSMLWVRQAPGKGLEWVSV

IHQSGTPTYYADSVKGRFTISRDNSKNTLYLQMNSLRAEDTAVYYCAKFP

STHGKFDYWGQGTLVTVSS

DOM7h-98-4

SEQ ID NO: 199

EVQLLESGGGLVQPGGSLRLSCAASGFTFGNYAMAWVRQAPGKGLEWVSS

IDMVGIKTYYADSVKGRFTNSRDNSKNTLYLQMNSLRAEDTAVYYCARGF

RIFDYWGQGTLVTVSS

DOM7r-31-14

SEQ ID NO: 200

EVQLLESGGGLVQPGGSLRLSCTASGFTFRHYRMGWVRQAPGKGLEWVSW

IRPDGTFTYYADSVKGRFTISRDNSKNTLYLQMNSLRAEDTAVYYCAKSY

MADRFDYWGQGTLVTVSS

---

The invention claimed is:

1. An anti-serum albumin (SA) immunoglobulin single variable domain comprising the amino acid sequence of SEQ ID NO: 181.

2. An anti-serum albumin (SA) immunoglobulin single variable domain comprising the amino acid sequence that is encoded by the nucleotide sequence of SEQ ID NO 87.

* * * * *